United States Patent
Sanada et al.

(10) Patent No.: US 12,227,743 B2
(45) Date of Patent: Feb. 18, 2025

(54) PHARMACEUTICAL COMPOSITION FOR TREATMENT OF DISEASES ASSOCIATED WITH UPREGULATED PERIOSTIN EXPRESSION OR PERIOSTIN SPLICE VARIANT SWITCHING

(71) Applicant: Osaka University, Osaka (JP)

(72) Inventors: Fumihiro Sanada, Osaka (JP); Yoshiaki Taniyama, Osaka (JP); Ryuichi Morishita, Osaka (JP)

(73) Assignee: Osaka University, Osaka (JP)

( * ) Notice: Subject to any disclaimer, the term of this patent is extended or adjusted under 35 U.S.C. 154(b) by 1186 days.

(21) Appl. No.: 16/963,476

(22) PCT Filed: Jan. 23, 2019

(86) PCT No.: PCT/JP2019/002015
§ 371 (c)(1),
(2) Date: Jul. 20, 2020

(87) PCT Pub. No.: WO2019/146621
PCT Pub. Date: Aug. 1, 2019

(65) Prior Publication Data
US 2021/0047642 A1    Feb. 18, 2021

(30) Foreign Application Priority Data
Jan. 25, 2018    (JP) .................... 2018-010354

(51) Int. Cl.
| C12N 15/113 | (2010.01) |
| A61K 35/76  | (2015.01) |
| A61K 48/00  | (2006.01) |
| A61P 35/04  | (2006.01) |

(52) U.S. Cl.
CPC ............ *C12N 15/113* (2013.01); *A61K 35/76* (2013.01); *A61K 48/005* (2013.01); *A61P 35/04* (2018.01);
(Continued)

(58) Field of Classification Search
CPC .................... C12N 15/113; C12N 2310/11
See application file for complete search history.

(56) References Cited

U.S. PATENT DOCUMENTS

| 2004/0029827 A1 | 2/2004 | Kawashima et al. |
| 2009/0074788 A1 | 3/2009 | Taniyama et al. |
| (Continued) | | |

FOREIGN PATENT DOCUMENTS

| JP | 6183809 B2 | 8/2017 |
| WO | WO 02/020055 A1 | 3/2002 |
| (Continued) | | |

OTHER PUBLICATIONS

Kim, C.J. et al., (2008). Role of alternative splicing of periostin in human bladder carcinogenesis. International Journal of Oncology, 32, 161-169 (Year: 2008).*

(Continued)

*Primary Examiner* — Ram R Shukla
*Assistant Examiner* — Shabana S Meyering
(74) *Attorney, Agent, or Firm* — Knobbe, Martens, Olson & Bear, LLP

(57) ABSTRACT

Provided is a pharmaceutical composition for the treatment of a disease associated with upregulated periostin expression or periostin splice variant switching, which pharmaceutical composition comprises, as an active ingredient, a nucleic acid capable of inducing skipping of exon 17 in periostin gene transcription and/or a nucleic acid capable of inducing skipping of exon 21 in periostin gene transcription. The pharmaceutical composition of the present invention can treat a disease associated with upregulated periostin expression or periostin splice variant switching, while preventing complete inhibition of the functions of periostin.

5 Claims, 10 Drawing Sheets
Specification includes a Sequence Listing.

(52) U.S. Cl.
CPC .. *C12N 2310/11* (2013.01); *C12N 2310/3233* (2013.01); *C12N 2320/33* (2013.01)

(56) References Cited

U.S. PATENT DOCUMENTS

| | | | |
|---|---|---|---|
| 2012/0058572 | A1 | 3/2012 | Taniyama et al. |
| 2014/0179767 | A1 | 6/2014 | Rozet et al. |
| 2014/0288155 | A1 | 9/2014 | Hovnanian et al. |
| 2014/0308685 | A1 | 10/2014 | Izuhara et al. |
| 2015/0111951 | A1 | 4/2015 | Rozet et al. |
| 2016/0108109 | A1 | 4/2016 | Taniyama et al. |
| 2016/0313351 | A1 | 10/2016 | Izuhara et al. |
| 2017/0044533 | A1 | 2/2017 | Rozet et al. |
| 2018/0016579 | A1 | 1/2018 | Rozet et al. |
| 2018/0216106 | A1 | 8/2018 | Haisma et al. |
| 2018/0362980 | A1 | 12/2018 | Pietri-Rouxel et al. |
| 2019/0106484 | A1 | 4/2019 | Taniyama et al. |

FOREIGN PATENT DOCUMENTS

| | | | |
|---|---|---|---|
| WO | WO 2007/077934 | A1 | 7/2007 |
| WO | WO 2009/001940 | A1 | 12/2008 |
| WO | WO 2012/168435 | A1 | 12/2012 |
| WO | WO 2013/053819 | A1 | 4/2013 |
| WO | WO 2014/136910 | A1 | 9/2014 |
| WO | WO 2016/142538 | A1 | 9/2016 |
| WO | WO 2017/098187 | A1 | 6/2017 |
| WO | WO-2018030451 | A1 * | 2/2018 |

OTHER PUBLICATIONS

Bai Y, et al., Novel isoforms of periostin expressed in the human thyroid. Jpn Clin Med. Nov. 3, 2010;1:13-20 (Year: 2010).*
Yoshioka N, et al., Suppression of anchorage-independent growth of human cancer cell lines by the TRIF52/periostin/OSF-2 gene. Exp Cell Res. Sep. 10, 2002;279(1):91-9 (Year: 2002).*
Cansu O et al., Periostin is temporally expressed as an extracellular matrix component in skeletal muscle regeneration and differentiation; Gene (2014), 553(2), 130-139 (Year: 2014).*
Taniyama Y et al., Selective Blockade of Periostin Exon 17 Preserves Cardiac Performance in Acute Myocardial Infarction, Hypertension, vol. 67, Issue 2, Feb. 2016; pp. 356-361 (Year: 2016).*
Yoshida S et al., Increased expression of Periostin in vitreous and fibrovascular membranes obtained from patients with proliferative diabetic retinopathy, Investigative Ophthalmology and Visual Science, Jul. 2011 vol. 52, No. 8 (Year: 2011).*
Norum, H.M., The notch ligands DLL1 and periostin are associated with symptom severity and diastolic function in dilated cardiomyopathy J. of Cardiovasc. Trans. Res. 10, 401-410 (2017) (Year: 2017).*
Cheng, C. W., et al., (2012). Levels of blood periostin decrease after acute myocardial infarction and are negatively associated with ventricular function after 3 months , Journal of Investigative Medicine, 60, 523-528 (Year: 2012).*
Hoersch S, et al., BMC Evol Biol. Jan. 28, 2010; pp. 1-5, Supplementary files (Year: 2010).*
Wang, UCLA Electronic Theses and Dissertations, Publication Date: 2017, Peer reviewed Thesis/dissertation, <URL: https://escholarship.org/uc/item/3655w9xw> [retrieved on May 22, 2024]. (Year: 2017).*
WO-2018030451-A1 Machine Translation (Year: 2018).*
Echigoya Y et al., PLoS One. Mar. 27, 2015; 10(3):e0120058 (Year: 2015).*
International Preliminary Report on Patentability for PCT/JP2019/002015 dated Jul. 28, 2020.
Aartsma-Rus, Annemieka et al., "Antisense-medicated exon skipping: A versatile tool with therapeutic and research application" RNA, 2007, pp. 1609-1624, vol. 13.
Baril, P. et al., "Periostin promotes invasiveness and resistance of pancreatic cancer cells to hypoxia- induced cell death: role of the β4 integrin and the Pl3k pathway" Oncogene, 2007, pp. 2082-2094, vol. 26.
Chijimatsu, Ryota et al., "Expression and pathological effects of periostin in human osteoarthritis cartilage" BMC Musculoskeletal Disorders, 2015, pp. 1-12, vol. 16, No. 215.
Fujimoto, Kiminori et al., "Periostin, a matrix protein, has potential as a novel serodiagnostic marker for cholangiocarcinoma" Oncology Reports, 2011, pp. 1211-1216, vol. 25.
Jia, Guiquan et al., "Periostin is a systemic biomarker of eosinophilic airway inflammation in asthmatic patients" J Allergy Clin Immunol, Sep. 2012, pp. 647-654, vol. 130.
Katsuragi, Naruto et al., "Periostin as a Novel Factor Responsible for Ventricular Dilation" Circulation, 2004, pp. 1806-1813, vol. 110.
Kii, Isao et al., "Periostin and its interacting proteins in the construction of extracellular architectures" Cell. Mol. Life Sci., 2017, pp. 4269-4277, vol. 74.
Kyutoku, Mariko et al., "Role of periostin in cancer progression and metastasis: Inhibition of breast cancer progression and metastasis by anti-periostin antibody in a murine model" International Journal of Molecular Medicine, 2011, pp. 181-186, vol. 28.
Masuoka, Miho et al., "Periostin promotes chronic allergic inflammation in response to Th2 cytokines" The Journal of Clinical Investigation, Jul. 2012, pp. 2590-2600, vol. 122, No. 7.
Morra, Laura et al., "Periostin expression and epithelial-mesenchymal transition in cancer: a review and an update" Virchows Arch, 2011, pp. 465-475, vol. 459.
Muratsu, Jun et al., "Selective Blockade of Periostin Exon 17 Ameliorated Renal Fibrosis in Unilateral Ureteral Obstruction Model".
Nakama, Takahito et al., "Different roles played by periostin splice variants in retinal neovascularization" Experimental Eye Research, 2016, pp. 133-140, vol. 153.
Norum, Hilde M. et al., "The Notch Ligands DLL1 and Periostin Are Associated with Symptom Severity and Diastolic Function in Dilated Cardiomyopathy" J. of Cardiovasc. Trans. Res., 2017, pp. 401-410, vol. 10.
Rios, Hector et al., "*periostin* Null Mice Exhibit Dwarfism, Incisor Enamel Defects, and an Early-Onset Periodontal Disease-Like Phenotype" Molecular and Cellular Biology, Dec. 2015, pp. 11131-11144, vol. 25, No. 24.
Shimazaki, Masashi et al., "Periostin is essential for cardiac healing after acute myocardial infarction" The Journal of Experimental Medicine, Feb. 2008, pp. 295-303, vol. 205, No. 2.
Shiraishi, Hiroshi et al., "Periostin Contributes to the Pathogenesis of Atopic Dermatitis by Inducing TSLP Production from Keratinocytes" Allergology International, 2012, pp. 563-572, vol. 61.
Takada, Michiya et al., "Periostin, discovered by nano-flow liquid chromatography and mass spectrometry, is a novel marker of diabetic retinopathy" Biochemical and Biophysical Research Communications, 2010, pp. 221-226, vol. 399.
Taniyama, Yoshiaki et al., "Selective Blockade of Periostin Exon 17 Preserves Cardiac Performance in Acute Myocardial Infarction" Hypertension, 2016, pp. 356-361, vol. 67.
Woodruff, Prescott G. et al., "Genome-wide profiling identifies epithelial cell genes associated with asthma and with treatment response to corticosteroids" PNAS, Oct. 2007, pp. 15858-15863, vol. 104, No. 40.
Yoshida, Shigeo et al., "Increased Expression of Periostin in Vitreous and Fibrovascular Membranes Obtained from Patients with Proliferative Diabetic Retinopathy" Investigative Ophthalmology & Visual Science, Jul. 2011, pp. 5670-5678, vol. 52, No. 8.
Ribomic, Inc.—Announcement of the Listing of New In-House Aptamer (Code: RBM008) Against Periostin—Jan. 29, 2015.
International Search Report for PCT/JP2019/002015 dated Apr. 2, 2019.
Muratsu, Jun et al., "Selective Blockade of Periostin Exon 17 Protected from Development of Renal Fibrosis", Nephrology Dialysis Transplantation, May 2018, pp. il-i660, vol. 33, No. Suppl 1.
Tomaru, A et al., "Oligonucleotide-targeting periostin ameliorates pulmonary fibrosis", Gene Therapy, 2017, pp. 706-716, vol. 24.
Supplementary European Search Report for EP 19743472 issue Oct. 1, 2021.
Office Action for JP 2019-567102 issued Sep. 6, 2022.

* cited by examiner

SEQUENCE LISTING

```
<160> NUMBER OF SEQ ID NOS: 49

<210> SEQ ID NO 1
<211> LENGTH: 36263
<212> TYPE: DNA
<213> ORGANISM: Homo sapiens

<400> SEQUENCE: 1
agactctcag gttgatgcag tgttccctcc cacaactctg acatgtatat aaattctgag      60
ctctccaaag cccactgcca gttctcttcg gggactaact gcaacggaga gactcaagat     120
gattcccttt ttacccatgt tttctctact attgctgctt attgttaacc ctataaacgc     180
caacaatcat tatgacaaga tcttggctca tagtcgtatc aggggtcggg accaagggta     240
```

```
agtgagtggt ttggttttat aaaccatttt tcttttcct cagcttgtta gatgttcaag      300
tatgcataaa gtttctcata tatgcctcag ggttttttt cctaattatt ataaagtaat      360
aggaaaaaaa ggaaaatgtg agtattctgt gatttatcta tgcactttta agctttaaga    420
cttaattgct ctctaaatac cttgaatata attgctttct tatgaaatgt tatataattc    480
taatctaatt aacacaattt agctgggcat tcttttataa ttccatttat ttatgttttt    540
attttcttcc aaaaatctga aattgagttt tcaaaattaa aaaatctatt gttaggaact    600
atcatatgta tgcaaacagc attgaaatat ctcacatgat gttagagaaa attttattta    660
aattacatat gaaggttaaa tactgggtaa tgtaactagt tctctgaatt ctttgaagca    720
tttaagttac ttttaaactc tgaattctgt aaaatttgca aaggtaattt atattttata    780
gaactaatgc aactcaaact aagcattttt aaaattacac ataattttgt aacttatcca    840
accatttata attttttaag cggatcttgg cacttcttcc tatgcctcac aggaattttc    900
ataatgttca caagcttctt tgacttacag tgaaaaaaga cttctgtccc tttaagaggg    960 gaagggaac cttaaaattg tgacagagga tgttctgatc tgttacttcc attcaaaaag    1020
ataaattctc ctttgtgcaa ccatattgtt tcaaagttaa ttttagcaca tttacttctg    1080
tgattactta cctagaaaat tacagagtat agtgtctgtg tacataataa accttgtctc    1140
ttttgctctc tgacctctca ttgttccaga gagccctgaa gttatggcca tcctccaaat    1200
gagcacatgc ttggtttaaa aagggtcagt agattatcta ccattaaaag taataaggca    1260
catagaaata aaattacgtt catactgttt gaatagtcct agttggttaa cttttgaaa    1320 agcttgtatt ttactctcag aaatgtataa tttttctctc tctccctgcc acctcctgta    1380
gactttcggt ttttcaacaa ttcagtagga ttgtgtcaat aattagattt gtgcaaggct    1440
agaatcatgt ctttggatat caaatccaca tctcaacatt ttcttctatc aaccaatctt    1500
tagatacgaa aaactagtca ttattaggac attaactttt ttccttcccc tctatcctcc    1560
agcccaaatg tctgtgccct tcaacagatt ttgggcacca aaagaaata cttcagcact    1620 tgtaagaact ggtataaaaa gtccatctgt ggacagaaaa cgtaagtctc tttttttttt    1680
cataatatgt cagttccaaa aacaacatca tgatgtatat gccttcccct gggtgtacac    1740
accattcttc ttgaaaatac tgaccaaaat tgtgagagtt atttaaagaa aagaaaggaa    1800
tacatacgtg aataaagaag ttctccctgc atctccaata ttactattag aactcagatt    1860
tcttcctgaa tccatgtgac atggaggcca gaaggaagca gatcacatgg ctcaggattg    1920
ggtatagaat ccgtgtgagt aaatgatgtt gtttctactc ctggtttggc cctcttttat    1980
cttaggcaag tcacttaacc tctgtgactt agtttcctca ttttataaaa aagtgggcca    2040
gaaaaacaaa ctgattttaaa atatcagagt ttctgaggca aaaagttaat gtttgtctct    2100
agtcatttgg aaattgtcta agtattcca gtttaccgga gagttttcat caaagtttaa    2160
agttaaaaaa tacttgagtt ttatctcttt atttaatcca gtgattctcc ggttcaagatg    2220 ctccatcccc agaggtccac aaggtgataa cggaagctca tcattatagt taatatctca    2280
atagcccaaa ggatgattat gttttaacat atgtttcact gattagctta aaatttgaaa    2340
gcattattta ttacttaata gacatgcctt ctggtttatt ttaccaataa atattggtgg    2400
aaaaaagtaa taaacactct ggacttatta aggtcaagaa ccactcctgt gatccaaagt    2460 ctttattta caatgaggga gaccagtcat aaatagggca agtaatgcaa tcagaaaggt    2520
ttaggtgtca tccccagtca agaaaacagt gcaagtggcc ccttcctgct tcctattaat    2580
ttgaagtcca ccctcagtga aggatccctt gagaatcaaa agaccccagg aagaacctgc    2640
```

```
ttaatacatc agcattaaaa ttcagttacc ctaagttcgg gtggaataat ttattagaaa    2700
cttatttcta agttaataat attggtataa atcctaaaca tgggccagga gtggtggctc    2760
acacctgtaa tcccagcact ttggggggc tgagacaggt ggatcacttg tggccaggag    2820
ttcgagacca gcctggccaa catggtgaac cccatctcta gtaaaaaaaa atacaaaaat    2880
tagccggatg tggtggcagg cacctatttg ggaggctgag gcaggagaat cgcttgaacc    2940
taggaggtgg aggttgcagt gagccgagat ggcaccactg cactcccgag tgggcaacag    3000
agtgagactc tgtctcaaaa aaaaaaaaaa aaagatacta aatatggaat cacttaactt    3060
cttgtagact tacctgtaaa acatggattt aatagctata ttatagagtt tctgagaaaa    3120
taaaatgaat tgataaatgt gaaattacta agtaaccata atgcataata tcaattgttc    3180
ttaaaattaa actcttttaa acaaatgcat agatgtagac aggaaaggaa gttgtgacca    3240
gatgcctatt tgaaatgcac aagattgtct ttatttctaa gtaagaacca tgtatacaag    3300
gcatttaagc ttagctgggt tgcatctcca catggtaacc aagtctaggg caccagagga    3360
cttttgctgac catctcctgc tcattggctt aatagagttt caacatgatg ttatcttttg    3420
acctgaacat tattcctatt attgtgcaga cttctgctag acttgtgagt cattcacaca    3480
attataatgc aatcagttgt tacaatgatc tctgccatgc tgcaagctag gccccagtag    3540
ggactctaag gctctgagtt ttcctctttg ttatttatat tcttggatac catgaagcat    3600
atttgaaatg cacacttaac tagataagaa aggaccttca ccctgaaatg ttagggagaa    3660
tgcttattac atccttccta gaagatagag aagaatgcca taaatttact ttaaccatct    3720
aaatatatga gagatgtcaa ggcttgtaca gaggctatgc caaaattctt tcttgctttc    3780
cattaaaaaa aaaaaaatca ctactttgaa gcctggcttt tttttttttt aaccagaaat    3840
gtaacagtgt ctcctttgtt caattgtatt agcttatttt tctaaagtag attcattttc    3900
aaaaacatag ttacgtctgg gcactgaaat aaatgtaaat gctaatttca aataaccaaa    3960
gaaatcaata ctattgacag gaagactgac tggtctgcca tctgcttgct tctgctgaaa    4020
tttccagaga tatcatcagg actttatgat cagatgacag aaatgtttgc ctttcagctg    4080
acagttgctc tggggatttg agaaaagtaa actgagcagg cctaatgaaa aacgtgaagc    4140
ttcctagggt caagatattg tccaaaatat atattggtct agtaatatag tattctggaa    4200
acttcctcta gagaatgtct gtgatatttt tagctggcat ctcatgaaat gttagatact    4260
attctgaaaa caaaaataaa tttctcatgt ttagagctat gtatagcaat atttttttta    4320
ctcttgtttt gccctactga ccatatggga acattgagtt ttgggtagca taaatgttct    4380
tctgaaaaaa actgcttttt ttttcttttc aaaatatccg ctcagagata accacattgt    4440
tcaattatct gatgatatta caatgaactg ctggaatttt atctcatcta ctgcattaat    4500
tctctacatt atgactgacc cttgtcatat tagcatttgc taataataat tttttgttaa    4560
atttcctttt ctattcacta ttttacttca agtaagtatt atcaatctat ggactaagca    4620
catttgtatc tcattttta aattgtttac aacatatgct aaagctaata tataagcaat    4680
tgttaatcaa tcttttgaca tccaataatt agatttattt acaagagctc atgtaaataa    4740
aattatttag aggctctatt atgatttgca taaggctcct atataccttt tatatgtttc    4800
caataccaac tattcttcaa actatattaa aattagagaa taacttgaag tgggtatttc    4860
ccatttaatt ttgtctgtat ttttagctat ctattattct taagccaata tttcatgcca    4920
ggaattttt attaacaaat aaagaatgag gatccaaggt tataaaccag actacaaatc    4980
```

```
ctagataatt acttagtgta gcagggttca atttgaaaac atttatttac ttttattcaa    5040
ctctataaaa tcatctttta tatcattaaa attttgctt cttgatagtt tgcttttatc    5100
attttatca tactaaaaaa agattttatt cttatacttg gcgatctctt tcatgtctaa    5160
attattttat tcattcatac ttcttgaata caattaagac aactggataa aaagccagaa    5220
aagaaatagc atttgaataa gctgattcat gtttaattag tgaattgcaa ataattaat    5280
ctataattgt cataatctgt ttgacatgat atttatcaat taaaaattac aaaacgatgt    5340
gcatttattt tttacttgta ataatccccc tatttctaat tgtttggtac atgtaccttt    5400
atatttcttt tgaaaggaaa cataagtaac tatgtaaaat ttgagttaaa ataggctacc    5460
tatgttagat gatgaagtcc agaaaatatt ctatgaaatg cgaaaaata aaaattagga    5520
ttatattata atattaataa tataattata cattaatata atcagttttt attttgtaag    5580
caattatata taattttaaa ttattatttt ccctcaaaat atagtaaatt agataaactt    5640
atttttgta tatcgtgata tcttgaattt tctggtctgt taccttaatt attgcctata    5700
gaacttaaca cacttcgtta actttaaaca ggatgccact ttcttgaata ctaaactcta    5760
atattaaaat aaacttactt agattatttt tatcaaattt tacaaaaata aaagattttt    5820
aaagtttata tataatataa tacaattaat aatcctacca acaattcaaa ccaaatatgg    5880
cattattta tctagcaatg agatagcatg ttacggactc caatgggtca atgtatttc    5940
ttatgtttcc aattatatta aagcagattt ctagccattt ttagtttaca aaatgatttc    6000
aaaagcatta tttcatttga gattcacaat tactctgtga gtagatatta tagctactat    6060
attcatgtta aatgctgggg gaaacaggga ctcctattga ttaaatgact tgctcaaggt    6120
tcacatgtca accaagtagt agaactagga cccaaatgtc gttcttctgg atcaacatta    6180
tggaactttt ctatagtaac atgagactgt agtgagaaat caaactcata gaaatataga    6240
aaaaatcggc cgggcgcagt ggctcatgcc tgtaatccca cactttggg aggcccaggt    6300
gggcggatca tgaggtcagg aaattgagac catcctggct agcacggcga acccccatct    6360
ctactaaaaa tacaaaaaat tagccaggcg tggtggtagg cgcctgtagt cccagctact    6420
cgggaggttg aggcaggaga atggcgtgaa cccgagaggc ggagcttgca gtgaacccag    6480
atcgcgccac tgcactccag cctgggcgac agagcgagac tccgtctcaa aagaaaaaag    6540
aaaaaatcag gggggaaaaa aaacctgatt tttagaaacct caacaaatca agtcaataag    6600
tgaaatattt tgtcaaattt atgtaaaaat gtatcctatt tagtttctca ttttaatatt    6660
aattttcttc ctatgtacag gactgtgtta tatgaatgtt gccctggtta tatgagaatg    6720
gaaggaatga aaggctgccc agcaggtaaa atctcaattt tttgaattaa ataaggaatt    6780
atatgcaaag aaagggttga ggtggcttgt ggagaagcca attgtgtatg tgtgtattca    6840
gcaccatcct aaatccaaga tatatccctc ctattttgt gttaatcatg aatttatgaa    6900
tgataaaata taagagcata tttctcatgc actggatgct gggcaataca acagaaactt    6960
agtcacaaat ttaaattagt tcagcttccc ttcaggaaca aaactcttta caaaatcctg    7020
ttctttgaac ttgtctagga acatggaact caactacttg gcaaaacttc atcttctcta    7080
gttgaacagc tctgattta taatattctt tatattgaaa tttggtttcc tctacttctg    7140
ccaactagag aaaaaaaaa tagctcatct atttcctctt tgaaatggca gccattcaga    7200
tatttcatgc caatcaccac acctttcctc cagctacctt ctcttcttga ataaagtctt    7260
ctattctctg gctaaccatc cccaattctt ttaatatgac acagactttg aagccctccc    7320
cattataaca ccaacccaca gaaagtctct agtccagtaa tctttcttct gaatacaaac    7380
```

```
ctagactgat atttaaagtc catccatgtg ggtctgagca tttaagacaa taccaagata    7440
agtacctgat ttggggacac cttgcacttt ggataatgtc attggtaacc atgttacatc    7500
attagcttat attgaattta gaatcaatta aaattgatta cagttttttt tacatacact    7560
attaagtcag gtctctagga tttgttttc tcaatttagg cataggaatt acatggaacc    7620
ttgttaaatt taaccttgtt cattttgact caatttctcc atcttttag ggtcttttaa    7680 aatcctggtt ttatacttaa tagttgtgtc accaaatcta aggatattca caatttaat    7740 aaccattgat tctatgctat taatcaaatt atactaattt tcaaataaat agggtcagaa    7800
aaaataagtt gactgcacat taccagataa atcccttcag gctgacattc attcatgaat    7860
ctttcttctg acgttcggga gaaataatct ggaaggattg aatattttaa atcatttgct    7920
cccagaaatt gtaatgaaaa caagcaggcc tacatatttt tagggaccca aatctataaa    7980
aatgatagat ttaaataaca gataatattg aattataatt gaattattat tgacatagca    8040
ggattgagat ctaaataggt taaatgttaa accaggatga cagtttaaat tttttttcc    8100 tcaacacaaa ggatatgtaa aataatgttt ttcagtagca ttttattatt tagcactcaa    8160
aagataactt ttatataaaa atgattattc atataattgt attgctaaaa ttattagcta    8220
aatgtcttgg gaaacacagc ataaagttta aatgattatg aataatatcc tgagaatatt    8280
atccccagta ctgattcatt tcttgattat ttcagttttg cccattgacc atgtttatgg    8340
cactctgggc atcgtgggag ccaccacaac gcagcgctat tctgacgcct caaaactgag    8400
ggaggagatc gagggaaagg gatccttcac ttactttgca ccgagtaatg aggcttggga    8460
caacttggat tctgtaattc attatttta tcaatatatt tattttttgc tgttattgtt    8520
atttcatttt aactgactta ttaacttgga tattagtaga aatttatat ctttctattg    8580 tacatatatg agaataccta aagggatgag ttattaaggg aagtaaaata tcttaataca    8640
tccgtaaata gaataaatct ccaggagact tatactttaa ttttttaag aaggggaatc    8700 aagaatcagc taaagggca cttactattc tattttactc ctttcctctt tcctgtttgt    8760
ttgtgaggat atgtatgtaa tttcagataa catgtctaac agaaaggtaa gttaagaagc    8820
ctactgaaat ttaaaattat cataagcagt attatacagc aatattttat tacgtatgtt    8880
taattatatg tatatatatg gatgttcagg ttgtcaaatt tgtatacatg tatgtggata    8940
gttaaatgaa atgtgaaaat acatttgatt ttcagacttt tgtgcacagt ctaatttaca    9000
atgccttaaa ttattactca atttccgaat ctataaaact gatataaaaa tacattccta    9060
ctttctacta gatatggaga tgaattgata attattacta gagtgaaata tacataataa    9120
aatgtaggta tatatctgta ggcattatct tgctacacta gctgtgtggt taattgcttg    9180
attatagaaa tcgctcctct ggttgtcttt caccgcatct ctaaccacct ctccagttcc    9240
ttttgctgac tcatcttctt ccttgcctta aagaattgag caatgagaac acatggacac    9300
agcaagggga atatcacaca ccagggactg ttgtggggtg ggaggagggg ggagggatag    9360
cattaggaga tatacctaat gctaaatgac gagttaatgg gtgcagcaca ccaacatggc    9420
acatgtatac atatgtaaca aaccttcacg ttgtgcacat gtaccctaaa acttaaagta    9480
taataataaa agtaaaaat aaaaataaaa agaatggaac ttataagaat tcttccagc    9540 acttgactct gctctttaaa tgcacttatc atggtttcaa ctatcacttt agtgcataca    9600
aacagtaaac ctacgcttgt tgtttggact tgtttcttct tggaacctca gtagaatatt    9660
tctattgttt atcttagcat ttatccttgg atataccatc tgcatcttta aacaaaagtt    9720
```

-continued

```
atctaaaaca tatgcaattt tctttccccc caataaataa ttggtttttt ttgttgtctt    9780
ttccccacaa ttggcagtac cagtgtcaat gttcagactt gaaatttgta agccatcctt    9840
acctcccctt tctccaattc ttaaaaactg ctgttagcct catctcatgt ttcatctaaa    9900
gtgatccccc taatactcta atttctgctg tacattacca ctcaaccttc ctgaagcctg    9960
gttctaatca ttaaattcca atgccacaaa atcttcagtg gttccttatg ccagtttat   10020
ttcactcctc ttagggcatt aaagttatcc acgttattgt cccacatacc cttctaaatt   10080
tcttagtatt atctgagaaa cataaaagtg tgtattaacc aaactggaca acttttgctc   10140
tcttggcatt caccctatct cagcactgga tttaaaagac caccacacca ttcctattca   10200
tttaaatctc atggtctatc tccaaactac ttccgaatag ctgttctttc ttattggagc   10260
cctgaaagca tttttcccct ctgtcctata tcttactctg tctacttttta cctgctgcta   10320
tatgataaac agttgtgact ttttgcttta cttatcatta tatttcccat agcattgagt   10380
aaagcataat atgacacata gtgttggata gataaaaagg tacaggacag ttgaattctt   10440
gaatttgtta tggaataaac atgaaaccct tgttaaaact taagtgttgc atacaaatat   10500
aatgtcattt ttgttttctt ttgtttgcca tttaaagtat tttaaatatg tgataatttc   10560
atatctccct ttcttatcat tttattattt atatcaagat tgtctcttca tcaacatatt   10620
cactttaaaa attgtgttct aagtactgta tcacattcag gatccttaag taagtatctg   10680
aacttacaaa atcccttaac caattagaat aatataattt taagttattt atgtcaattt   10740
tgtatgacca tctgataatg aaatgagaaa atagcaagag agtagaaata gggtgatcgt   10800
aagacttttta ctaatgttcc acaataaatt gaatttctat cattgcaatt tttcctagga   10860
tatccgtaga ggtttggaga gcaacgtgaa tgttgaatta ctgaatgctt tacatagtca   10920
catgattaat aagagaatgt tgaccaagga cttaaaaaat ggcatgatta ttccttcaat   10980
gtataacaat ttggggcttt tcattaacca ttatcctaat ggggtaagtt ttatcagtaa   11040
aaagtacact tatgaaaaat accttcttta attttgtcta tactttttat ataatgctca   11100
caaaaataat aaaatgttag tgagaataag gtaagtgcta tattatgact ttaccccccaa   11160
atctagggca tgtaaatttc caatctggtt attaatttct actaaagagt gattgtaaag   11220
gacaaattac atgaacagtt cattgacagt agacaggtat tctagaaaag gaaattttag   11280
tagttgatat gtttgaaata atttatcgta gtagcaaaaa gaataatcaa agaatgagtg   11340
ttctttttact cccccctctag ctactgtact aactgaagta cttgtgtgtt tggatcagat   11400
tttgtgggaa actgccaaca gggtcatagg acttttttcca cagccagcca aattctcagg   11460
gacgaaagag gtcaatgaag aaacaatttt taggaagttc ttgtaatgta actaattata   11520
tctatacaat aattatttgt ttctccctct caaaacttaa attttaggac tgattagact   11580
tctttaccta attcattgac ccacattaaa aagtttatga ctatttgcat aaaagagaaa   11640
agcaataatt taaatgaaaa aaacacccttt gccttatgtt gctagatatg ttaagtatga   11700
cttgacttgg gttctcaact ggttcccttt tctcttacag tttcttttttt agatataaca   11760
acatgtaaat cttcatccac agcgtttaca tttacaatgt agtttcctgt atgttacatt   11820
tactagtata aatgaaaaac tgggaatggg cttgcagtct cagtggtcaa tgggtatctc   11880
tggtttcagc actttgattt ttccaaataa ttataggttg tcactgttaa ttgtgctcga   11940
atcatccatg ggaaccagat tgcaacaaat ggtgttgtcc atgtcattga ccgtgtgctt   12000
acacaaattg gtacctcaat tcaagacttc attgaagcag aagatgacct ttcatctttt   12060
agagtaagtc caagagcaga ttgtcttgag tcattgaaat ccctcttctt ctcctgtcaa   12120
```

```
aatctaaaaa caataaaaat gctattaaat ctggcaaaaa tgtaacacat attttttgaa    12180
aggactacta ttttcatttt acacagaaga aaccatctca tatgaaataa taatatttct    12240
gtggacatga tagagtaaga atggttagtc acatgactgg cgtgtattta gctcatttag    12300
aacgtgttca tctgttatta tatgtactgc tggatattgc tacagtccca taaacatggg    12360
cagaattccc attcttgcaa acacaatttg aagaaagttg aaaagacat ggttgtgtca     12420 aaaagtaata ttttgaagat ttaacaacaa caaacctcta tagtgtagga atcagctcct    12480
tcatgtcagc ctaggctaag tgtgttgcaa tcttttttctg gatttacaat gtgaaagtct   12540
ctgaaaagca catttgtgtt tcaggcagct gccatcacat cggacatatt ggaggccctt    12600
ggaagagacg gtcacttcac actctttgct cccaccaatg aggcttttga gaaacttcca    12660
cgaggtgtcc tagaaaggat catgggagac aaagtggctt ccgaaggtag tttaatgtct    12720
tcatctctaa ggagtctccc agcattctga gaagggaata aaaagaggc tagtccttac     12780 caataatatt agtttaata agcaaaggca gggaaaaatt tttattctga gatgtactat     12840
gtcttccaaa agtccttaaa agagtaggca gagtataatt cttaaataat aagaatactc    12900
tcaagatcac attctttcat actgctttca agtaaataag tagtagatat tcagaaggat    12960
tagcaggtgt tggaaagaaa tattagatca tcaaatttta atattgtatg cacgttatgc    13020
aatgctttta attctgtatt tatgccaaaa gatattgagt tgtgagaact gtatggttct    13080
cttgggcctc taattactga tacacataag aatttggtgg ctttccaagc ttctttgctg    13140
ttgtcagata ggttttacat tgtgcttgca tacttcactt actcagccta tcccaaaata    13200
catttaacca atttaagatg agaaaatttt aggatgcagg atagatataa tgtagttgag    13260
gcatagatcc ctccagaggt ccttcaatga atcatcttta tttggttact ttctagaagt    13320
tgccttccgg aaataaatttg tcttatcctc agcctctatc gacctcatta catgttatat   13380
acaaatattc tgctatgagc agctattaca agatactgct cttgggtatt ttggaatttc    13440
acaggccttc cttttctttc tcttttggta gagagggatc ttgctgtgtt tctcatcatg    13500
gtcttgaact cccggcctca aacaatcctc tcacctaggc ctcccaaagt gttgggatta    13560
caggtgtgag cccttgtgcc agtcaaagtt cctctgaaag gaacaattct tgctttcaca    13620
tcaggagtta cttttttatg atagctggaa cttaacctac cacgttttct aatactgcac    13680
caatcatttc ctgaagctga tctcctctta ttattcctac gaagctgagc tgtttctatt    13740
ttatagttga taggaaaaaa cttttagaac ataaatagga ttttaaagct gttagtgaat    13800
ccttaggttt tactacattt taaggaatac ttagttccac agtgaaacac atcttttcag    13860
ggtcaaatgt tatttcccctt gatctgaaag ctacctgttt ttattgtgtt ctccagctct   13920
tatgaagtac cacatcttaa atactctcca gtgttctgag tctattatgg gaggagcagt    13980
ctttgagacg ctggaaggaa atacaattga gataggatgt gacggtgaca gtataacagt    14040
aaatggaatc aaaatggtga acaaaaagga tattgtgaca aataatggtg tgatccattt    14100
gattgatcag gtcctaattc ctgattctgg taagcaactt ttttttgtttt tgtttttgtt   14160 ttttttactta ctgtaatttta ctaattatgc tgtctcaaag agtaagtcca tgaaaaatga  14220
atgtgcagta taagaatgg catgcaaagc actaacacaa taaatagtga gctacttgag     14280
cactccatag ataggcagtg tagtgatggg aactccatgc atgaatcttt ggctttctag    14340
ggtttctgac atctaatatt tataaccgtt ttcacagtgc cagagttttt cttggaaaga    14400
gaaggaaaga tctaaccaaa tggtcagctt tggataaatg gaaaagctat ggaactcaca    14460
```

```
gtatagagag aaagatgaga gatgaacaat agagaattaa agaaacatgt agtaggaaga    14520
cagaaaaata ttttccttct gaaatttatc gtgattatca actcccacca aaaaatggaa    14580
gtggaactct cttattaggg aggaggagga tgtcttatca cactgacatt gcagtaaata    14640
gcttacaata ttagaaaaga gtcaggaatt gatttactag tttcatgatg gagataatag    14700
caatgatgac attgttgtga tggtgatggt ttattttca gccaaacaag ttattgagct    14760
ggctggaaaa cagcaaacca ccttcacgga tcttgtggcc caattaggct tggcatctgc    14820
tctgaggcca gatggagaat acactttgct ggcacctgtg aataatgcat tttctggtat    14880
gtgctggaca ctgttgttcc tgctctctgc ctacacacct ttttttcttt atgatgattg    14940
tttgcaataa gaaacaataa atgttttagg aggtgttgat tagtttctgc attggctaca    15000
catacaatgt gttaacacta catggtctct actaaaatgt tcttcatttc taaacatttc    15060
attataatgg ataatagcct acagagagtg aaatttgtaa tttgtaatta agactattca    15120
ggccaggcgt ggtggctcac acctgtaatc ccagcacttc gggaggccaa gacaggcaga    15180
tcacttgaga tcaggagttt gagaccagcc tggccagcat ggtgagaacc catctctact    15240
aaaaatacaa aaattagcca ggtgtggtgg tgcactcctg taatcccagc tactcgggag    15300
gctgaggcag gagaattgaa ctgaacccag gaagcagatg gcaccactgc actctagcct    15360
gggcgacaga gtgagactcc gtctcaaaaa aaaaaaaaa acgaaactta aaaaaaagca    15420
tatttagttt ctctgtgaat ctaatatttc cagcacaata aggatgcatt gacagatctc    15480
taaaaaaata aaactgattt ctttatttga taccaacata ataatattta gaaataaata    15540
ggtgtgtttt gcatctcaaa atttggacag taagggtgtc aaattataaa taaataaaat    15600
gaagagactt atacacttcc atatcatgat gtaaaatagt atatataaat atttcaccta    15660
gtagttgcta ttcacagacc atgttcagat tcatgcaacc ttcgaccttt ctcaggaaaa    15720
tgatttcaca gacatatttta aattgttagg caacatttat taattaaaaa taggtaacac    15780 aatttttgt ttttccaaat gctaaattgt gatataaaaa ctattaatca aaaaaattga    15840
attcctagat atcctgactt tcttctttgt aataatcctg cccatgtgtt ttgacaataa    15900
cccatattta agaggttgtt tgctttgatt ctctttccag taatcaagat taatttacaa    15960
aggattcatc agtagttctt tcatgtgact aacagatatc taattatcag acaaagcctt    16020
ggccaccatt aaggtttagc atttgccagt gaccactata aaactatgta gcccttacag    16080
aggtgaaact cattgattga actggttgga actgtattat tgtcatttaa tacaataggt    16140
cacagagttt ctacttggtg aattgaattg ttagttttta gcatttggtt gattcatgta    16200
ttatatgagt gcaaaatcca tgatatcaat aatgtcaggg attatctgtt tatatgattc    16260
tgtcttaccg ggagaaactt caatgttttc taaataaaat aatgctcttt cttaatgaat    16320
ttatttacag atgatactct cagcatggat cagcgcctcc ttaaattaat tctgcagaat    16380
cacatattga agtaaaaagt tggccttaat gagctttaca acgggcaaat actgaaaacc    16440
atcggaggca aacagctcag agtcttcgta tatcgtacag taagtgaatc acaacaaaat    16500
aaaaagtctg tcaaatgaca tgtcaaataa tgctgtttca atgaatattt cacagaattt    16560
tatgagtgtg gttctaatag taaatattca tagaagcatc agggaactgg gtagcttggg    16620
tgaaaagact gtgagcaaag tccacaacaa gtgctatgta ttcaaaactc agatagatat    16680
tttgcatgtg tttcattatg aataacttc tattctagag catcaattat tttaaattcc    16740
agaaagcagt aaattttta aaataaactt ttccttttgca gagtacttta caattttcaa    16800
ggtaattctg ttctctgcct acacaccatt tttctttatg atgattgttt gcaataagaa    16860
```

```
ataataaatg ttttacaagg tgttgattag tttctgcatt gactacacat acaatgtgtt    16920
agcactatgc tgtctctact aaaatgtttt tcatttcaaa acatttcatt ataatgaatc    16980
aaatatgcaa ggtgatctta tactgtaaaa taaccagtca gcatctgaat atcttttgaa    17040
tggctttcaa gataaacctt tattggcaca tagagatttc tggactctaa aaagggttt    17100 taatgtactt ttttttttta agggacagaa tttcactctg tcacccaggc tggagtgcag    17160
tggcacaatc atagctcact gtaaccttaa actccttggc tccaggggac cctcccacct    17220
cggtcttctg agtagctagg actataggtg cacaacatca ccctagttaa tttttaatt    17280 taatttttct tgagacaggg tcttgctaca tttcccaggc tggtctcaaa ctttcagcct    17340
ccagtgaacc tcctactttg gcctcccaat gtgctgggat tacaggcatg agccgctgca    17400
cccagcccta acatacattt tgctgcagga aaatttatag aaatattgct tatcaaaatt    17460
acagttcaac taatgatacg ttcagtattt gtccagataa cacgtacagc tacaactaaa    17520
agacttcaca ggaagtcagg cattacctag aactgaatct ggcacatgtc agcagctccc    17580
tgcagctaca aaattccaaa cattttaag tatgcattaa atgtgctgca ctttaaattt    17640
tgtatataca aatatatgtg tgtatatata tatcacgttc gttcaaaaag ctatgaatat    17700
gtcaatgatt tgacttacaa tgatgaatag ggtcttacag tcaagaaaat aaagtaaata    17760
tttgtgaaga tcactaaaag cactaaagtg aggaaaacctt acagatagtg ttggccaaaa    17820
gagggtctag agaaatagtt caaatctgaa tagaaattat aaaaaatgta gaagtgggat    17880
tccatggaac ttttgtaatt tattgacaaa attacctgcc tgatccataa ggtagcttga    17940
cttttaataa aaaacccggc tagataagaa gtgtcttgtg agtttgtgtg agccattgaa    18000
aacagaggaa agaagctgtt cccgtggcct cagacaccag gcaacctctc agaagggccg    18060
atccggaaac ttaattatgt agttacatct atacgggaaa tttcaagcaa ggaaaatgac    18120
accccatacc tttctttcct ttcctaggct gtctgcattg aaaattcatg catggagaaa    18180
gggagtaagc aagggagaaa cggtgcgatt cacatattcc gcgagatcat caagccagca    18240
gagaaatccc tccatgaaaa gttaaaacaa gataagcgct ttaggtaagc ctattagtgg    18300
cacctccaca gagaatgaga gctattggca tattttgtt tcataggcgg tatcccaaaa    18360
ggcattcagt ctcctatgtg gttgaaaatg gaatttagaa taaaatgttc atacaagtgt    18420
tttcaaaatt gatatatgtt ttcgctgcta ctttctggta caccgttata tgatttcatg    18480
tgtgaaaaca aatctaacag actaaactac ttcttgacat ttttcttata gttttagaa    18540 attgatggta tatatagcaa agactatctt gtagagtatt acatgataaa aatgcttctt    18600
ttttgttatg tgtgaccttg tcaagtttta taggatgaaa tcagatgaaa aaaattaaaa    18660
attgtattgt atatttcagt catttttcat gataaaactt ttaacaggta aattgtattc    18720
gaaacatatg aaaatgtatg agcagttctc tcatgctttc cacaatacat ggattctatt    18780
ctattacatg cactgtaggt gaacatacct aaatctaaat ctgacaaaat acatatacat    18840
tcttcccact tagcaccttc ctcagcctac ttgaagctgc agacttgaaa gagctcctga    18900
cacaacctgg agactggaca ttatttgtgc caaccaatga tgcttttaag ggaatgacta    18960
gtgaagaaaa agaaattctg atacgtaagt ggaagtgaat tccagatatt ttcccttca    19020 tttcaggatc tcacttcttt ctcaagcttt cctgtccaga tgtctgcctt aaaaatgccc    19080
cctctctggt attcatggtt agctttagtt tccttttatt tcgtccactt gggatgtgtg    19140
gagggtcact cagtaatgtt cttaaactgt gaactgttat gttgttgggc tagatgttca    19200
```

-continued

```
cttatgtggt ttctattaaa gaccatgtaa tcaggggaca aagaagaaaa cagttataat    19260
ttagaaaata aatagatttt tttctcccag taagttgggt tctatttttga ttaggctaat    19320
tgaaataact atgttttgaa atagcatcga tatctacttg agagaataat gatattatga    19380
gaaagtacaa tatggaaaaa gataaagact aataagtgtt ttgtttctta gtccttatca    19440
aaaagtcata ttattcaata aaaataaaca tatattttcc cctaggggac aaaaatgctc    19500
ttcaaaacat cattctttat cacctgacac caggagtttt cattggaaaa ggatttgaac    19560
ctggtgttac taacatttta aagaccacac aaggaagcaa aatctttctg aaagaagtaa    19620
gttgtctaga atgaatttat gatagtgttc atccatcatt aagttatcta aatattcatc    19680
cttaatgaaa tttcctcatt gaaattgcct cctatttga taggtaaatg atacacttct    19740
ggtgaatgaa ttgaaatcaa aagaatctga catcatgaca acaaatggtg taattcatgt    19800
tgtagataaa ctcctctatc cagcaggttt gtaattattg aactcattga taggctaagt    19860
cttttttttaa tatgaacctc gattttattt ttatgctttc ttaccaatat tcatttaata    19920
tttctcttca tagacacacc tgttggaaat gatcaactgc tggaaatact aataaaatta    19980
atcaaataca tccaaattaa ggtactaaaa gttacttgat ttatttctttt ttttttttt    20040
ttttttgaga tggagtctcg ctttgtcgcc caggctgtag tgcagtggca tgatctcagc    20100
tcactgcaag ctccgcctcc catgttcact ccattctcct gcctcagcct cccgagtagc    20160
tgggactaca ggcgcccacc accacaccca gctaattttt tttgtatttt taggagagat    20220
ggggtttcac tgtgttcgcc aggatggtct cgatctcctg acctcgtgat ccacccgcct    20280
cagcctccta aagtgccagg attacaggcg tgagccaccg cgcctagcct aaaagttact    20340
tgatttattt ctaatatgta gaacatatat tacaggttta acataacagg ctagaaatgt    20400
acgcattaat aagtaagtat gtactgggct tggattactc tttgttgttt atgtaccact    20460
gacccacctg taaagaaatg gcatcatttc ttcatggttt tgttcaacaa atatctatta    20520
aaagctactc aggaccaagt attgtgtaaa gtgttatgaa aaatatgtat ttaaattgga    20580
catgtctttta ttcaaaaagt ttacagtcca atttagaaaa ataaaatggt acataaatga    20640
ctaaaatcgt tgtatcattc aatactttca ctgcagaata taaaggaaag aacattcact    20700
tataaaaaat tgtcactcat cacagattaa agggaacgga atattttttct tcttttttcaa    20760
tgtagggtaa aagtagcagg aaacataaaa ttgtgtttca taaatatatt taactttgga    20820
ttaattatta tataattttt aaatctctga gtaatgaatc caatgatttt tatgccctct    20880
gacctgatag cattgaattg gaagatgatt tatatgagga cttcacttct attaagtgta    20940
ataatagctt cactattttt actttaataa gaattaaagt ggtgccatgg ttttgttaac    21000
acaactatca cctttcatgt tactaaatat aaacatttat tttcagtttg ttcgtggtag    21060
caccttcaaa gaaatccccg tgactgtcta tagtaagtat ataataaata ttggccacct    21120
gggtggcaag gtatgaaaaa agaaaacaat acatttcttt gtatttacag agattattga    21180
taatctggta tttagaattc caaactatgg ccaatctcat ttcacttgaa aaaaggattg    21240
aggtctcaga taaccttcaa ctccaatgaa cttcttcccc actcattgga aaaacagaaa    21300
tgatatgaca tgagaaagac agcaaaatat aatattagcg tggcaaagag ccaggaaaat    21360
aaaaagacat ataagggaa gagatggcga aaagaccctc tagaaatatc taaaaattca    21420
gatgtgtgga cacagaaatg accttagcca agacttgttg ttcacgccac cctcaagccc    21480
tgagctatct aagggcaggc tgagaagcac gtgttgaaga ataccaatgt ttataaggtg    21540
gcagttcaaa aactctccca tccaaaattg gacaaaggaa caaaaaaatc tgccatgtga    21600
```

```
caaatttaaa gtttccaaat tccagggttc tttgatctct gacacaacca gattatcaaa   21660
attaaacctc tactacttaa caatgataaa gggtatttca ttctcataag tgtagctagt   21720
agtatatctt ttccatcatg gcttttctc  tgtttatctt ttctctcttt ctttatttca   21780
ctgtagcttt caagcagaaa ttcttttcat tttgttttgg ctctgtaatt aaacactcaa   21840
agtgtatcag tagctaaaac attacttcaa tacccacatt tattctggct agaaaatcat   21900
tccattttat accatgagca tccagttatt taattaagaa aatttccctt aagatttata   21960
ctagatatgg aaaaggagta aagccaatgt aaggagcaaa acaaaatgtc tgctgctgtt   22020
gttgatttca attatgcaat aataacatgc aattccagga tcaggccagc tcagcactgt   22080
attaaagatt taattggaat agttatgatt caccatggga atacaatctt gtaaaaaata   22140
tgttttctga aaattaagca atccttatgg gctctattca tcagacatgt tatgtcatct   22200
ttcttcatca aggtataaaa tatatacata tgcatatata tatatacaca ttcccactac   22260
atttctttag cttcccttct ttatccatct tagtttcact actttctata tatgtgaatg   22320
caatatcttg attacaatga gcaaaaatat aattattttc tcctactaaa ttacatcctc   22380
actcacagag cataagctac attttattaa gacacacatg ttcaatggtc cttccctacc   22440
tacccagagg ccttgaaaca gctctaacat ttacattcca atgtaagatg tttcttttac   22500
tcctccttag acggtatgct gttattaaga agtattttaa agtagaagta aagataaatt   22560
aaaccaaatt ttctattttt atatttcgtt gttgacttgt ttctaaaatt cctataattt   22620
tttgctgcat attatcctca tccccaaaat aacatccatt ttaaagtgta tagttgaggg   22680
gaaggatgct gttttggta  taagttgtca aatatggaac atttgacctg gagagggcta   22740
aaatcaatat ttaatcctca gagcttcacc tgtcaaaact atttaagtct gcagaaaatc   22800
aagattgaaa tgaaaactac caaccagctg aacatccaaa acgtcaaatt ccttaacatg   22860
atgtaaaaaa tgtaagctaa aaggaattag tccattttga tagcagcaat agagagccct   22920
gtgtattcgt attcgacttt catggaaagg ttcttctgtg gcaagaccac ctgtggaact   22980
agtacctaaa cacacagatt tgttttattt tagagcttca caatttgaga tctcaaaata   23040
caaaacctaa taaggctgaa acacagggtc tatgaaggct aagaacccac attaattcaa   23100
aaagttgaca cagctaaaca tcttacaagc atgaggtgag aactgcagaa accaaagctg   23160
tgctaacatc tcacctctac tgctttgatg tgatctagat gcacgttag  cttcagtgtg   23220 gcccgttatc taatagaacc atctttcaag gcttttcatt agaaatgaca aaaagccagt   23280
tgctctggct gtgtggcttc agaggcacat ttccagttaa tcagtacaac caaagtcaac   23340
caaatagttg actggtattt aatttatttt aatttacttt tattatagat ctagggggt    23400 acacacgtag gttgataga  tggatatatt gagtaatgct ggggtttagg cttctagtga   23460
acccatcacc caaacagcaa acatagtacc tagttcaaag actattatct tacttaggta   23520
gacgacacac gttaaaata  tatacctta  aattaaaaaa aaaaaggat  agtgataaca   23580 aagctgaaaa ttaaagacat tttagcctat aacttaaata ctgatcatat catgtttgtt   23640
gaatagagct catgtctggc tggctgaaat ttattcttac ttttaagtat tctgaactat   23700
gtttcatttt ttcctttcta tgtcactgtt atcagatgca tgaaaacat  tttaaaagcc   23760 ttttctttc  atttttcctt ttaattgaga agaatccag  caatgcaatt taagatatta   23820
tgaattgcat gacattaatc atatttgtct tctgttgcaa tgcagccagt attttcaaga   23880
agtacaaaag aaggtaaagc gctttagcgg tacaattaaa aattacagat ttctagatat   23940
```

```
aattcctcac tttgtgagta tatatttcac tagatcaaat tcaagtcact agacttcaga   24000
gttcaacacc tggacatgag aagatattat attatgtacc ataaatattt cctgtatctg   24060
actgcctgaa catattacca catcctgtgc cttagtatcc tacagagaca aaaagaaaa    24120 ggaaaaaaaa aaaaaacctt tgttcaggtt tttatgtaaa tattttcat gttccacttt    24180 ctatactttc agcaactaaa attataacca aagttgtgga accaaaaatt aaagtgattg   24240
aaggcagtct tcagcctatt atcaaaactg aaggtaaaaa tcaatgttat acatggttcc   24300
ttttatagta aaaacatctg taaaaatact gatctctatg aatgtatcta cattctttta   24360
aaaactaaca tgttaaatgt tatataacca atattatacc aatggcatgc tcatgtaatt   24420
gcagaatgcg gagtgcaaat tatttagcaa agtagatgat gcattcctaa tactttcagt   24480
acatttgctt gtacttgatt taatttgaat ctaattggca ttgcattaac ttagtataca   24540
gatactcact aaacaaagac atgagttttt tttactttag tcagactcct acaggctgta   24600
tactctttat gttgctttgt ttgcaatctc ccacatgttc tttcttataa cagtgcaaga   24660
agctcttcca aaaaaaaaa gtataggcat ttttcattgt gtaacataag atagcataga    24720
agctatgttt actgaaagct tttaaaatta caaccacgca tgagatattt tttaattaga   24780
ccatcagaat tataaaacaa aatgagtagt ttatgcagtg aattgatttt taaaatactt   24840
aattccagcc ctgaacatat tattacatac agacgtatat attatacatg agatatatat   24900
aatacagaca cacacacaca ttctctcctg atgtttcaga ctagaacatt aaataagcag   24960
ttacttttct ctctactccc actatgtatg ttagccaact tcaacatctt tgatgttact   25020
ttcatttcat gtattttaat tatgtccaag gatcacaatt taaattttt aagatttcca   25080 tgtataagca tcttaatgta gcaacttacc cagagaaaag aactagttat ctcctttgtg   25140
ctataagaaa gctagaaaca gtcttccaaa agagaacag attatatctt tgatggaatc    25200
tttgggaaac tgtaattata cttatgtttg gttttgctat ttcttttggt ggtttgagaa   25260
ggtaacttct tgaatacttt tatctatatt ttttaaagta agtcattaat ttaaatttat   25320
acactgaaaa tacataggta aaaacttatt tcctagctaa ttagttatct atattagtat   25380
ttattcttga gacttaaaat tgagttattc tttgaaatct atccttgttt ttttcttgaa   25440
aaaaatacta taattataat tatttaatcg actttctata gtgatgaaga caattcggta   25500
ttttaagaag aaattaaatc agaaagtttt gttgaaaaaa tgttccttga tcattgtaat   25560
aaaacatgac acaatgatct ttgataatac aattgatttt aaaatcaaat cttgtcctgt   25620
ttttaaaaat cagattccct aaaattttgc actataattg tgcacagctt ctttacctga   25680
aattatttac atgtgccaat gttcttattt tcaaagattc ttctcctttg aagcttcttt   25740
attcaactta tttatctcct caatctttgt cagtaggatt ctatcctact aatctttatt   25800
cagttaagat catactggcg ggtcatctct acatggcttc ttcttataaa gggaacatgg   25860
atgaaaaatg gagttgtgtc acctactcat taataacttg agttcagaaa ttacactcct   25920
gtgtagcata atgaaggaaa caaatattta tcttagtagt aatttacaat ggtccagctt   25980
ccaggattgc tactggcatt tccttcttac tatttgaaca attacagatt tattgatgac   26040
ttttaaattc ttactaaatg aattaaactc caggacacaa ttttaaggtg tctcttataa   26100
aagatacata acagcatttt ggaattaaga ataaatcagc taaaattcaa ttcaacaaat   26160
agttattgag cagctattct gctgggtact ttctgaggtg ttgggagtaa ataggaaaac   26220
aattttgaga aaatctcttc ttttatagag cttaactata aaggatgttt ccaaaatttc   26280
agtttggctt ttctaaagaa atattgattt agatatttta ttaacgcatt tttggttctt   26340
```

```
aaattcctta ggcgtccttt cttttgaagt taccgcacct taaaaacctg gctttatgtt    26400
ttgtgctcaa tatcccttgg ccttatatat caaatattat ggcatgaaat acttatggtt    26460
tcaaaaaact ttacttttat tttcattatt ttggattgtt ctaggctggt ttcgttttgg    26520
taatcatgta cattgacaat ttctgaacaa gcaaaaaaaa atgctctcaa agataagcaa    26580
gcaacagttg cattccacta ttgaaggcta ttacagtatg agttaaatgt actgaactta    26640
tttttcttac tcctctgtga aacagtctta attaactaat gtagtaagca gctttctaac    26700
cttcaaaatg attttctgtg gtagcaaaat cattttgcaa gtcaaatgca acactagttt    26760
atcttttgca tttgaaggac tgtttaacta ttaactggtt aattgtgtat cattcccata    26820
cagaaggtaa gtactcaaat tattttcctc ataaaacctg acattcagca tcttaaaggt    26880
aggtatacat ttggtacttt cttatgttca ctcctatacc cactagatca aaatataag    26940 gtactgagtg attttaaaac ttaaatgaaa aattttaata aggaaaaagt aatagacaat    27000
atcagtatga taaagtggga tctacaccag ttatcagaga aacacaaatg tgtacatact    27060
gcatgatctg caaagtgtag ccacatataa tattttgcat aatcatactt tataactacg    27120
aataaacaga tggatttatc catctgttta aaagctaaag cagatgaaag taattttagt    27180
agcacacaaa cagactaaat catttgttct cataactctt gtctaatttg aagacaatgg    27240
gaaatattta aaagtgattt catagagcct gaaaccactt tgacatttga gttgagtcac    27300
accgaatgtt gaaataaatg tcctattccg gtaaatttaa aggactgttt taacatgata    27360
atttgtctcc taaataatg tcccaggacc cacactaaca aaagtcaaaa ttgaaggtga    27420
acctgaattc agactgatta aagaaggtga aacaataact gaagtgatcc atggaggtgc    27480
gttccttatg ttacctgggg ccgactacct tcgctgtgat tattttgaaa tagtgttggt    27540
ttagaaatat tgaacatctg atattttctc ttagttctta ttttataaaa attgtgggaa    27600
ttatttcctc agctatgagt tcttattagc tggtcagaaa taaaacatag ttagctttta    27660
atggatctag ttggaattaa tttatctatt aagtcactgg gcccaacaaa atgtcatgat    27720
ttttgcatat acaagtgagg attgtggaat aaaattgtaa cattaatgtc agtataaaag    27780
gaaatattag aaacagtagg aaaaaatgac cattgtataa gtctctgtct aataagccac    27840
tccactacta ggatttatga tagggctccc attccaatga tatagaactc cctggattct    27900
cactaagtat ttattccaca tccagaaaac aagtatgaca tggagagtta ggatgtcaaa    27960
tggccctctc tctcaaccaa gattcaggac atagctatta ccttttagat ccctattgat    28020 atgattttg ggggatatgt tctaaaaatg tttatgattg aatcttaaat ggtaatattt    28080
gtagaaatat agttaatcat tacaatgtct agcttatgga tgtatagtca caatatgagg    28140
gtaaatcaaa tgcatttgta ttcccctgct tttagagcca attattaaaa aatacaccaa    28200
aatcattgat ggagtgcctg tggaaataac tgaaaaagag acacgagaag aacgaatcat    28260
tacaggtagc cattaattcc atacatggat ctatgcctag attataaaga tcaaattata    28320
gttaatcccc aaatataaga atcattaaag aaacaagtca ttttcatagt gattactaaa    28380
gttacttcat attttggcag atataatatt attctaaata tgtaatctat gttttactct    28440
gaattgaaaa tttgtagaca aatctaaaag catttgtttt tattacatgt atgcatacat    28500
acatgtaata tgatatacca ttgatatgat attccatttt cacttactg tttgttaatg    28560 agttagagga ccctagaaga aaagccattt cctcatttga gcttccatta atcttaaggt    28620
ctgtacatct acctgccaaa atagaagcaa gtttatacaa agcaattgat caatattttc    28680
```

```
agtaaacctc atatcagact tccaaactag cgtccagttg gtccaaatta gcctaaaatt    28740
cgccgaaaat ccttaattca gctattcttt aagtatttgt ttaaacaatt agtgagcaag    28800
tgtggcttgt gccacccatt tatggaaata aagttttatc ggaacacagt ctttcccatc    28860
catttatata atacctaagg ctgctttcac actgaagtat cagagttgaa caatggcaac    28920
acagactaca tggcccacaa gtgtaaaata cttactctct gtcacttcgc agaagaagtt    28980
tgcctacttc tgttttagac ctttttcatt gtccttctca taggtcctga aataaaatac    29040
actaggattt ctactggagg tggagaaaca gaagaaactc tgaagaaatt gttacaagaa    29100
ggtcagcatt tctaggaaaa taagaatgtg actttaccta agctatccat atacaagtct    29160
aaaataacat tctacatgtt ttctactcta tctcaatcta ttgttcattt ccataccaac    29220
aagaaaaaag cacaagaata aggaattaag cataaatggc agtcatattt tttatacagt    29280
attttgttca acaactttat aagaatatta gtatgtcaga aaacagcact aaaatttgtg    29340
aaagaatcga gtgttgggct ggaattcatt attgggcaga tgccattatt tatgacataa    29400
agtctgctgt ctttattttg ttatataaac caatttctgc tataaacatg tatcctctca    29460
gaggtcacca aggtcaccaa attcattgaa ggtggtgatg gtcatttatt tgaagatgaa    29520
gaaattaaaa gactgcttca gggaggttag taaaaggaca caactaacc cccttaacag    29580 gttctagtga ctgagttcaa ctttttaaag actgagcaag cagattttt cttttaattg    29640 ggttaaaaaa aaaaagaca acatccactg ttgtcttaat agatggattg gttcaatggt    29700
agttaatagt tatgaagaaa tgattactag tttaaacagt ctttaaaaag ttctatggta    29760
taaagtttgg ggagcaatga atatttttt tgctttgatt cagataattt taagggcctt    29820
ttaagtatgc aaaagggaaa taattgttaa attgctagct gttaaacaag cccaaatttg    29880 atatacttt tatatttaaa aaattatatt cactgccccc ataagagcaa tcaaggcatg    29940
tctttaaatt ctatacatag atatagccaa aaatagtgca tttagtaaca ttcttttcca    30000
aaactatatt cttgggaatg aatatctgtt tcttctaaca gtttgagtga taatctatac    30060
ctgtagatat aagttatttt gcatataaaa ttaatcttaa tcttttatgg aatgttctct    30120
gtctgtggca ttaaatgaac cttaagaaca aaaaaaaag aattcaaaat cttacacaaa    30180
ccctacatag taattattca aagatgttgt ttatatagat acataatttg tatcattggc    30240
atttgaataa acaaatttct acttcatttt ttaacaagga aagaattaag ctgaaaaatt    30300
attttttgtg aaacatgtat ttatattctt tagaaaaacc aaataggcac tttgaaatat    30360
actattaatt gagaaacata actgaagttt gatgtttatc caaaacacag tccagatggc    30420
ttttcagctt atacttttta aaactgtatc actatgtcca agaaaatgta aattatcttg    30480
ggactttcta tattttttagc aattattatt tctatattct gtagtttaat aaacgtaaaa    30540
tctcttaaat agtatttaga aacttgtcag tgatagttta aaaatttta attcaaccaa    30600 tgattgaatt ttccctcaat agaaatatat atgtctgaaa aatacaagtt tcctcccaga    30660
attctaagag tacatagcac aacagagcca taacggaacc aaagattcct gtaggatcta    30720
acaaagaatt cactatctac ccctaaatgc tcaactgtct gctaggaaaa aaatctaagg    30780
atttgaggga agagacaaac acattatgaa gattaaattg aattcttttt tttttctttc    30840
agtccttgcc atagtaagca gctttgtaga atggtagtgc tttttaggga atcaataaat    30900
tagtagctgc atcagtttat attgctttaa ttcatttagg attaaatttc aggtaagtat    30960
attttcttcc ccttttgataa gccccctgtta ttgaggccac tatgaaaaat ccagttaaat    31020
actaaagaat tgcttcagcc aagaaaacat ataactgcta caagttaagt atatgacatt    31080
```

```
caattttag ttaatgaact cctttcttag ctcttgcctc tgatcatccc agaagtttat    31140
tcctttagtt cccagtgtat gatctctcta catatctgta aggcatcggt tttcacaatg    31200
ccacgtcaac tattatagca ttgtgaaaaa acaaaaaaaa ttaaaagttt ttatcaaatc    31260
atttctccaa ggttttgctt tttgtaggaa aaacactata tgcggtagaa ttactagtac    31320
cagcattaat tggacatgct tgttttcttt tttccagcta tctaaaacca tcaggtcatt    31380
actgagtcac aagtatcccc ttgtctagat cctaaaaggc attgataaaa gaagctagta    31440
aagattacac tatgtaagac ttttttttt tccaaggtct ggccaattaa tacatatctg    31500
aaccatgctc ttcaactcaa taagttctac ctaaaactga attttctatc taaacagttc    31560
atatcgtata cattgtggta catgtagtac attttttttt tttttttttg agacggagtc    31620
tcgctctgtc gcccaggctg gagtgcagtg gcgggatctc ggctcactgc aagctccgcc    31680
tcccgggttc acgccattct cctgcctcag cctcccaagt agctgggact acaggcgccc    31740
gccactacgc ccggctaatg ttttgtattt ttagtagaga cggggtttca ccgttttagc    31800
cgggatggtc tcgatctcct gacctcgtga tccgcccgcc tcggcctccc aaagtgctgg    31860
gattacaggc gtgagccacc gcgcccggcc atgtagtaca tttttttgtac ttttggtaat    31920 ttgagtatat ttctcaatca tttaagtcat gactattaac atggctaact ggtactttga    31980
gtactgatgt tgtgatttgt cactgataca cttccaagac cttaactgaa aaatttctc    32040 attaaatgca taaaatttt gggcttacct tagaattatg cattctgaaa cgactcaagc    32100
aattaaagga gaataacaga ctatgtcgaa aggaacaaca acaaaaagtc atttttgaag    32160
gttttcgcaa atctgccaac ataagaggtt aagatttgta acctctatag agaatagtag    32220
atcgagttgt aggtctgcat tcagtctgag ccccaactca atcccaaatt agttgactct    32280
tttcttgctt gtttccttca tctgaaagtg aggatagtag tgatacctac agtctaaata    32340
agttaatata tgacaagctc ttagaacaat gttcagcaca aagtaagctg tcatcaaatg    32400
ttactgtcaa tcatcaattg acattaacat ggtcaattaa gtaatgtttc tcacccaact    32460
ttaaatttcc atagtcataa ccatggaaac atacaaaaaa caaacatgca ataaaaatgt    32520
caaaataatt gagctgagta ctttgcatgc tttaggaaat aagatgtagg gtggttcttt    32580
gtgccaatat attcaagtaa ttggtttatc ttcccatgtt ttgctgctct aaacatgatc    32640
taatataact ctcattcatg ttgacatagc agagagctgc taggagtaaa cctgttttct    32700
acacattaat caagctgttc tttcaaagta tttgtttgac acattgaatg ttttttattc    32760
tggaatatta tcacagcaaa acctcattaa ttggatgcta tcaaaattat gaaaggaaat    32820
ctgagtgagc acacttgttt tgaaaagaaa ttggtaaata cttctatgat gcagttttaa    32880
gttatacaat taactgctat ttggaattta ataagtccac tataagcaat gtgcctgcac    32940
accaattaaa ggttggatct gtctcttctt gacaatttt tagaagccat tatttcgtta    33000
ccaaataaac ctgaagttaa gaaatattta tatttacatc tatttatatc tgttggagaa    33060
tatttcataa ctcagacttg gttgttttac acagacttct ccccattatc caacatagtg    33120
agatttttct atagttctat attttactct agtattaatg tggttttata aatgattata    33180
tgccttatat tctgggggga aagaaatgtg aaaatgtgct aagtagacag aaacagaata    33240
tataagttgt tttgaatgtt atttcttttt taaaaatttt gcttggtgtc atatagccaa    33300
aactattcat ggtgacagtt tcattgctta cttttatat gatttcagcg aattgaaaac    33360
atgtatataa tagaaaaaac tggacttcat gctgagtata gatgatacat ataaagaag    33420
```

```
tcaaaatttg gagaaaaaat ttaaaaagat aagtagaaaa atgaagtaac tgtagaaacc   33480
atacttactc tttgatctca aatgcccaaa aactgaatga aaatgtgaat ttaggccgac   33540
caggtagtct tgtcaataaa ctaaagaaaa acaggaaaa ttgagaaata tgttacaact   33600
ataacaacac aaaacagcat agttttgaaa cacttgcagt tcttaaatat aaaagctttt   33660
attagttaat ttttaaaag gatctcatag gattgacact gaatcaggtt gggaggtgga   33720
acaagggtga tggcatattc tttctgaatt acttattata acatttctag aatcattagg   33780
tcagtgctac tttgttgtcg tcaatgtaca ataaggaat cacaaattga tcttagtgat   33840
aattttacag aggcagacat tgcacatagg tatgactgca aaaatgggtg gctaactctg   33900
ggaagatact tgtgttaaac tttatatgac atttaataac ccttcatcat aaggcaatgt   33960
tttttacaaa aagattgaaa aaatcatgta agtcatttac tctgcaaaaa tggcacatta   34020 ggtgggggttc caaaatccat aatgaaacaa tgtgttttgc aactaagaaa cattcattat   34080
gatatatgga aaacactgtc tgtctacttg tcctttacga aaaaatgtaa aactctgagg   34140
atcataaaat ttaactacta aaaataatct tcgtgtttaa gtgatactta tttaagactt   34200
tacactgttc tgtttaacca tggtctcctg tctgatttta gccataattg cgaagtattt   34260
ctaactacaa caatttaatt ttagacacac ccgtgaggaa gttgcaagcc aacaaaaaag   34320
ttcaaggtaa gtgtattggc tatagtaatg tgtgtatatg gcctcttttg ttacatgaag   34380
agaaatcaaa caataggaaa gattttaaag tattttattg aaacttgtta tcgatcagag   34440
agaaaagcta gccagttttg atgaaaacaa ttttgataac aatcagaaaa taaatttctc   34500
atgttctata ctatcagaat ctaataacaa atattaaggg aaaggtcaac atactcatgt   34560
aaactgctag gcatattgaa cccttgagat agactcaagt gtatattctc catacatata   34620
tatatatata tatatatata tatatatata tatatatata tatgtaatgt tttgtatata   34680
caagtataca tataattttg tgtatataag agttaagtca aaagaaatt gttgaatatc   34740 agagataaac aaatgtagat tgcaggtgga cctgaatcct taaaaatgtt attatgtgag   34800
acaatgctac agtttgagac ataagtaaat aagaaatgta tatatgcaaa aaaccattaa   34860
tatagctatt tacaaaatgt tcatttaaat atgtagatta tatatgtata tatcacatgt   34920
gcattacaat ttatttcata attacactat gtgcatttgc taattcctcc acttaagtta   34980
tcttacattc caatacattg agagagcaag aatttcccctt gtggaagcta gagtaaattg   35040
caagtttgga attgcaagtt tggaatttct gggttaatta gatactagta gtgaaaagga   35100
gacacaaggc ttatcaatgc gctataggaa cttcttactt taaaccaatc caatatacag   35160
acctttgaaa gtaaaagatc aactgcacag atattttta actaaagaat gtgtcagtaa   35220
atctatgtaa atatccaaat tgacacaaat tttctaaaga gttaaaatta ttaaatttca   35280
aattattatt ttatatactt ttgatcaaaa tataatattt gcttcaccat aagttgaaga   35340
tattaagaaa acataatcta aggtttatta caaaaaataa tggcctctga tagatataca   35400
gagaataata tattcttaaa ttttaaaatt tcctaacatt tacagtctat acattctcct   35460
ttctttctaa ttaggatcta gaagacgatt aagggaaggt cgttctcagt gaaaatccaa   35520
aaaccagaaa aaaatgttta tacaaccccta agtcaataac ctgaccttag aaaattgtga   35580
gagccaagtt gacttcagga actgaaacat cagcacaaag aagcaatcat caaataattc   35640
tgaacacaaa tttaatattt tttttctga atgagaaaca tgagggaaat tgtggagtta   35700
gcctcctgtg gtaaaggaat tgaagaaaat ataacacctt acacccttt tcatcttgac   35760 attaaaagtt ctggctaact ttggaatcca ttagagaaaa atccttgtca ccagattcat   35820
```

-continued

```
tacaattcaa atcgaagagt tgtgaactgt tatcccattg aaaagaccga gccttgtatg    35880
tatgttatgg atacataaaa tgcacgcaag ccattatctc tccatgggaa gctaagttat    35940
aaaaataggt gcttggtgta caaaactttt tatatcaaaa ggctttgcac atttctatat    36000
gagtgggttt actggtaaat tatgttattt tttacaacta attttgtact ctcagaatgt    36060
ttgtcatatg cttcttgcaa tgcatatttt ttaatctcaa acgtttcaat aaaaccattt    36120
ttcagatata aagagaatta cttcaaattg agtaattcag aaaaactcaa gatttaagtt    36180
aaaaagtggt ttggacttgg aacaggact ttatacctct tttactgtaa caagtactca     36240
ttaaaggaaa ttgaatgaaa tta                                            36263
```

<210> SEQ ID NO 2
<211> LENGTH: 31770
<212> TYPE: DNA
<213> ORGANISM: Mus musculus

<400> SEQUENCE: 2

```
gatgtcatta ctgatcctaa ttggtaaata ttttcgaagg gttggcattt gttgacttga      60
tgagagtttg gtaagtctca aacatgatgc tcagagtgga acgatttcag atttctatta    120
ttggacacta taaaaggggg gtttcagggt gccttttgt catacgagag tatgctttgc     180
cttgtgccaa acagtgaatg tgtgctgctt gtcagaatac tgcagtaacc tcatcaataa    240
acattctaac agccagttgg ttgatatcag atagaccta tgtgcatgag atacggctgc     300
cttttcattg agcagttacg gacagcccac catttgtaca aactaagagt agcaaaaact    360
atttataaag caaacaagaa aaagaggcag ttaaagttag aatagtttca tttagataaa    420
tataaataag agattagatt tctatcacac aagtgccctg gaaggaacat agtttacttt    480
ccatgatagc ttctctccca gttctccaga gatagtttta tacactttca atcctttaat    540
accaaaattt cagaagtgac agaggcctct gactcatctt caaactgtgt tgtttggctg    600
tgtacttaat aaattagctg ttagttgcag gattatttta acactgaaag gaaacttctc    660
atgggaagct tacacatctc tccagataag gaattctctc tggactaatg tggcctccct    720 tcaactttc caactgtaaa acagccacag tgtctttgcc ttgtcagtgg gaaaacaata    780
ctgacaccca taaatgggta tgggggggg cttcacaaca cagcacagaa acacccccc     840 tctctagaga tgctttaaaa tgtgtgcatt cacagagact gatggctgtt tccattcctt    900
gccaactgaa gcttcgtatc ttcgcagctt cttcatcgaa aggtttctct gcatctcata    960
tctggtcatg tgtgaagacc taaaaaacaa acaaaaaaca aaaaaacaaa aaacaaagt    1020 gtcttccctc agctaagaat gctgaggttc aactccaaga gagtacagtt gttcttacag    1080
aaagcagaag gatactcttg gcagcaaccc tgtttcttaa tatgcattta attgccacat    1140
tatttctgga ttagtaatac ttgttttccag ggcttatcag agtatgcagt gtgtgtgtaa    1200
tggaaaacaa aaaaaagtaa aattgtgaga aagatagata gatagataga tagatagata    1260
gatagataga tagatatatt tcaaaagtta gagaaattct cccaaagtag atctttgtta    1320
cttaaccctc tatactcatt atgagtttgaa aagacatggc cccagtttca taggacttca    1380
aggggcatgt gtctcttcca cataagctgt ggaaatcaca ctttaaatgc attgtacatc    1440
tatccaggat ttgggttaaa tgcccctgtg atttctcttc tccgtgttct gctgtggagt    1500
gatttaagtg caatcagatc aaaccaggaa agtaactgag ctcagagaca cagagtgtgg    1560
tggcagagac agaaggcaga gagatcccta aactcagaat cagctctttt cgcaatgtaa    1620
```

```
acctatagaa gtgaaaaacg ggctcaccat gattgaaaac aaataggaga cagagttcag   1680
attgctcaga acccaggaga tttccaggga cagcccaggg ctgctggtgc ttctgtaagg   1740
ccatcgcaag cttcaggttg gcccagcgcc ccctcccaca gccttgctcc ctcccacagc   1800
ccagagctat ataaactcag ctctccagag cacaggccag atctcttcct ggacggagct   1860
cagggctgaa gatggttcct ctcctgccct tatatgctct gctgctgctg ttcctgtgtg   1920
atattaaccc tgcaaatgcc aacagttact atgacaaggt cctggctcac agccgcatca   1980
ggggtcggga tcagggtaa gtccctggct tgttttatct ttatgtctca cttagcttgt    2040
tctagaaata tgcgtgaagt tccttgtaaa tgcaccacag gggagctgtt ttacttattg   2100
caaggtaata ggaaaagaaa caattatggg tcttctataa atatacatat atagatgtag   2160
atagatatac agttactatg acatatatat gccttaaact cataagaagt gctatcaaca   2220
tagcaagtat ttttaattga tgtgggttgt taattttaat gtaattaacg aaatacagtt   2280
tggtaatcct tactaattca gtttacttgg cattttattt ctttccatta ctgcagaata   2340
tggttttcaa aatcagagtg tctgctcttt aatggtatca tgtcaaaggt tttaagatgt   2400
cctgcaagat atcagtgcaa atttcctttg ttttgtatgt gaaaatttaa ctctgggctt   2460
tttggagtat ttttttaatc ttctaggata aatgtaggat tttcaaaagt tattagaaac   2520
atcttagtaa ctcaagcaaa catctgcaca cttttgcatga gactcttggc attcctccct   2580
aagccttagg gggattttca ttttttctgag ttctcagagc agtctgctta gcagtggagt   2640
agaatttcca tccctttaag agaaagcaag cttaaaattg caatagagaa ggatactctt   2700
acttgttctc tttaaagaaa caaatttcat ttgtgtaaag gcattgttca aaagttactt   2760
ttaacaccaa tctacttctg taagcaccta gggagtcaca cagcagagtg tgaagtaaaa   2820
cctgtgtcct ttaccatcag tctcctgctg tcgagaaaaa tcctgaagct acccatctcc   2880
caaatgaata aatgcttagt tttaaaataa tggaatttt ctctattaac agtagtttgt    2940
acataaatct aaactctgtt aagtctaatt ctgttaaaat atccctgcca ggttaacttt   3000
ttgaaatact ggtataagtc tcaagtatac agtggtcttc cctgccttcc ccttcctccc   3060
ccttcccttt tcccttctcc tcaccccctcc cctccctaca tcctctcctc cctcctatac   3120
ccctcccttt ttcctcttct ccctcctctt cctatctttc ttagacttct gcttttgcca   3180
gcagctcaat agaactggga caggagttag ctttatacaa agttgagatc tcatcttgga   3240
atgtcaggac ttcacccaaa catttctttc agtcacctga cctgtaattg ggaagaggca   3300
ggtgccatag caattaactc tttttttcct cgccctcctc cctctctatc tccagcccaa   3360
acgtctgtgc cctccagcaa attctgggca ccaaaaagaa atacttcagc tcctgtaaga   3420
actggtatca aggtgctatc tgcgggaaga aaacgtgagt ctcacccttt tctttattga   3480
aagtttgaag agcctacagg atggtatttg cctcttcttg ggcacacacc ccagttgaag   3540
atactgtcca aactcatgtg tttttaaagc aaggcacatg cacaggcaga gaagctccct   3600
ctcaacacca ctgttataag agtagatttc tctctaagtg cataagctga agaggccaaa   3660
gcaggccctg tgaccatgtg atatgtcctg aatctatgtg aaaaaaaaaa aatgtggtct   3720
ctactcattg tacactcttt gttgttttgt cctcttctgt cttaagagat cctaatacac   3780
tctgtgtttc atttgcttgt cttatatcta tacacacaca cacacacaca cacacacaca   3840
cacacacaca cacacactca gaatcaagga gaacaaattg atatgaaatg tcaaattgta   3900
aaagcccaaa tagatgtttc tccagtcatt tagacatcat gataaagatt ccacttcacc   3960
cctgaatttt cactaagcac aaagtgagaa agatgttgca cttccacag gctgcctgat    4020
```

```
ccccaggaaa ccattacagt gacagtgaag cccatcactt ggtcgaatat tcctgtagct    4080
aaaaggatga ttctcccatg gttctgctgt atatttcact gatcaactta gagatggaaa    4140
acatgattga cgatgtagta gacatgtttg ttgatttatt tcactatagc tattggtaag    4200
aaaaataaga acactaggtc tataaaagtt aatcacttgc ccaatttatc attttacaaa    4260
gagggtgctg tctcaaaggt aggatagctc atgtcatccc agtgttgaaa ataatggaag    4320 ggcccttgc tgccatcaac ctgatcctct atgaggtagc cttgaggact ggaggatctg     4380
aatatgtact taagatacca tggtgaactt catgtaccct ctaaagaggc tgaggcaaga    4440
agactgcccc aacctctaca acctctagga taccttgagc tccaaagtga aaacccttta    4500
aatacataca tacatacata catacataca tacatacata catacataga aagacaattt    4560
ctatcctcgt gccattggga caaacactca atgcagaact atttaagctt gggaagtcag    4620
tgatcttcct atgttgagtg tttaaggaaa gtattttcat gttctttctg gaagttaaag    4680
tcatcttatt ttcacaatgt aactatatta gagatgccaa agttgtcaca caaccaaagt    4740
cgagtctctt gttttccatt aaccaaaagt tgtgctggta gccagacatt ttaccaaaac    4800
tttaacaatg tacccttggc aaaatttcct ccagttgctt ccatttcaaa atcacattta    4860
catctcttca ctgagacaaa tacaaatgct aacctcaact aagcaaagaa accaatggaa    4920
tggacaggga ggaagcctgg cttgccctcc actcccttcc tgacacgtcc ttgccagcat    4980
cttctgtgtc atgcagcttt ttaagttgtc ttctggttaa tcagcgacat tgggaattta    5040
ctagaaagaa acaggccagg tctcaagaag gcatcagcat ccctaggctt aggtttaagg    5100
cactgtttat agtaatgtag aatccttcc ataaagcatt ccacaggctc cctgttggtg     5160
caagtgacat gttcagttgg cttcctgtga cattttgtt actactcaga tagtgagggc      5220
aaattcccca cctccaagct gtgcagagca attattatgc ttttttcttg ctttatgtga    5280
cttcctggcc atatagaaaa atggatttgt gtgtagcata tgtgctttct gtgaacaaaa    5340
cctaaacgtt tttgttgtat ttgaaacatc ccctcagata aacacattgt ccacttctca    5400
gctgaggtcc caggccactg ttctgcaagc tcgccccttc cccagcatga cttttttctgc   5460 ttcagagctg attatcagat tgtattaatg tttggtgtag acatttgtct cataaacaca    5520
gtgtcctgtt ctcatcttat tgatcttcag gtctcttcct atagacatat cttatgttta    5580
ttgtttacaa tgtgcttaaa tcaaattcac aagaacattc aattaatttc tacaaagaag    5640
tataattgtc acaaggggg caaatgaaga tttgcattgg ggtcacacgc agttcccttg     5700
tttcagttga gacaactctt tgacattaca aaaaagaag ctaaaacaaa ataggaaagt     5760
ttaaatttgt atagaacagt taaattaata acaataattg ataaattaat gaataataaa    5820
tgatgataat ttttaaaagt aactctgtat cttagttata aatagagctt acttggttga    5880
ctgctttccc caaatgcaca gagccctggg tttgatcccc aacaccacat aaatccactc    5940
tgatggcttt caccatagag aatcagggt tcagggtcat ccttaagttc atagggagct     6000
caaggtcagt ctggtctcat gagacactgt cgcatgtggg ggggagcgat gaaataagac    6060
agaagagggt aaaatgaat aaactgatca aagtatatca tgtgtatgta tgtaaacact     6120
agagaaatct ataatccata ctaacaattt tacatgagat aggatttcat acattaaagt    6180
gggctagtat atttctagtt tcaaggtacc atacaccaat gagcattttg ctggtattta    6240
gagctaacac agttatccta aagacaatct ttcggtattc acaactattt gtattttgat    6300
attatcattg ctcttcccgt attatactgt tggaagactg aattctgcta tatcaagaac    6360
```

```
attgtttaag tacatctgtc tagtatacag agaaaatgca cactaaactc catccttcag    6420
taccaagatc caggactttc cccccactgc ctcaagggtg cagagaaaaa tcaaacttgc    6480
ataactatct ggtatctata gggtagaaac aaaagatggc ttctacaatc ttagcacatt    6540
ataggaataa ttaatattct gctcatctta tgtgaaagta catggtttgc agttctctct    6600
tttaatattg aaatttcccc ccctctatgc agcactgtgc tatatgaatg ctgccctggc    6660
tatatgagaa tggaagggat gaaaggctgc cccgcaggta aaatctacat ttctggattg    6720
tacatgggag cttttcctct gtgaggaacc agttcagcac accaacagtg tgtgcatgca    6780
tgaatgtgtg ggtgtgcaca tgtgcatgag tgtacaggtg tgtgtatgca cgggtttgga    6840
acaatcataa acctaagaaa attcttcatg cttttgtgct aatcacatgc ttaccataat    6900
ggtgaaatat tagacggctc ttctcacaca cagggatctg atggtactag atactaacat    6960
ggagtctaat tgaaactagc tcagatcctc ttctttgagc tcatttacaa gcagggcatc    7020
tacttacgaa ggcaacatct ctagctcacc agctctgaat gtgtaacggc cctcgctttg    7080
caatgtgatt gcccctaatt ttgccaataa aagaagttgc ttttcattt cctctggata    7140 tgcaattcca atcatcaccc atctccaggt tccttctcca caacagaagg atctcctctt    7200
ggacataggt cctcccctct aattgcacat aaactctaaa gcacttactg tcatggacac    7260
caacccatag acagtccctg gcatagtatt atgttcagaa tgaggagcta agctggtgtc    7320
agcaacgcac acaggcctga gcagctgaaa ggctatcgag gacctcactt gctgagaccc    7380
agtgcttggt taatgctgtt ggtgatgagg tcttgttata ccacaggctt tctcccatga    7440
aaactgttgg gctcagttta ctctaggatg tgttttgttc aatgtaggca tggacttgcc    7500
ctgaaacctt attaaattta accttattgg tgttattttg ctttatgatt taatctaata    7560
attgtctcag ggaattcact aaagtagtca tttactttat ggctagttcc aaatgactct    7620
aattttaaaa tcaacggcat ctgaaaagca ggcagcctgc agagtgctag atctatcttt    7680
tcagattggc atcaggttgg ctccaggaca accttctaaa agtagtagat atgttttcct    7740
taaatcaaaa tggagagagc catgtccatc tattgcttta gggaccaaga accataacaa    7800
ttataggtat aaacctaacc tgctgctcag agacttgact cagcattgcc gcgcacacgt    7860
tatccttgcc agtctcaatg aaggcaagaa acaccttgtc ttttggcaaa ataactagtt    7920
atattctcta aaaatgctga ctgaactatt agtgaggtgg caggatttac taaatgctac    7980
ttcagtttga tattttaaaa ctcacttcct taacgccaag aatataagaa atactggcgt    8040
gaatagagct ttattatata atactcaaaa tgcacatttt gtgtatttgt gcaaaatagg    8100
tgattcctgg gctcttactg cttaaattga gcagttcaat atattggtga gtaggtaaag    8160
tttgaatgat tgtgaaggaa cattctggaa atcaacttct aagcatttgt tcgattctga    8220
ctctttcagt gatgcctatt gaccatgttt atggcacgct gggcattgtg ggagccacta    8280
ccactcagca ctactccgat gtctcgaagc tgagagaaga gattgaagga aaagggtcat    8340
acacgtactt cgcgccgagt aacgaggctt gggagaacct ggattctgta attcagcctt    8400
ttcgctctct gaggcactta ctgtgggatg ctgccatttt catgttaatt gatcaactta    8460
tgaacaatcc aagaacattt aatatttctc tattgtatac ttgaaaacat ttttaaaagt    8520
gtcattggga cagtggcatg tgttcactct gtcataggaa acaatctctt taatgggaag    8580
atcaatgaac tgaaagaata tttagtagta gtagtagtag tagtagtggt ggtggtggtg    8640
gtggtagagt attttattcc tcttctctta ccttctttgc tgtaagaaaa tatatgccat    8700
ttcagatagc atgtccatta gaaaggcaag ttaaaatgcc tacctatatt taaaaatcta    8760
```

```
ttaggaacta tattacaata gctgtatttt attatagttt gtaaataaca tagctataaa  8820
catagttgca ttaaatgaga agctataata aatagtttat acttacttat ttatacatac  8880
atgccacatg ccacatgcca catagattgc tgttccaaga ttgtcagaat agtagatgtc  8940
tatctctgta tatttaaacc aagtgttata acaatatttt gattttatga acagactaat  9000
tcatgacaga gtaacctatg aaggaaggat cccttaattt ccggctttac ataactagta  9060
gagaaatgtg tttctacact atgctcgtgt ggagatgaac ccacaatgtc aagggtggct  9120
cagcgaagcc tctcaggcac agtgtcctgt agctttgctg tgttaatgct gagtcatgga  9180
ccctcatctg ctctgcacct cagccccctcc aggttccttc agaccacgcc tgggcatcct  9240
cacattagtg gtaaaagtta gatatttcct cccagaactg tagcctgccc attgcccgca  9300
ccttaaaaac tttgcctctt gccttagtgt gtgcaactat gaaagctgtg ggattggtac  9360
tggtttccct aggaagccca gtgattctaa tctgcacatt aatactactt cttcaacata  9420
tgatatggct acataaatga agattgtctc ttcgtaaata tatttaaaag cttttttttt  9480
tttgccctaa aattatccaa gcattctatc agatttggaa ccctccagtg acaccttgga  9540
attccaaaat tcctcagtca attgaaataa tataattctc ttatttttgt cagttttcta  9600
tgaacaagtg ataatgtaac aggaaggtca caaaagagta gaaacagggg tttggagagc  9660
tgacccaaca gttaggaatg cttgcaaagg agccaagttt ggttcccagc acccacgtta  9720
gcagctcaca accacctgga acaggtgcca gtctcctcca cacactctca cacacatagt  9780
gtatacagac atgcgcacac acacaagtga aaatatgtca tagagaagac ttccatagca  9840
aaccacagca gattaactct tatttcattc ttcctaggac attcgcagag gactggagaa  9900
caatgtcaat gttgagctac tgaatgcctt acacagccac atggttaata agagaatgtt  9960
aaccaaggac ctgaaacacg gcatggttat tccttcaatg tacaacaatc tggggctttt 10020
tattaaccat tatcccaatg gggtaagaac ttatctattt attattcat tcatttataa 10080
aatttctatt tttgagtcac ttttttttaa aaatttatc tgctcccttg agcagaaatt 10140
gttcacagga aggatataat gttgtcat gtgaggtcaa tgcttgtatt atgattaaga 10200
agaaaaacac cctgtccatg taaaatttca atccaactct taaagacaga ctgattggca 10260
gttaggggca atgtgtgttg agcaggttct tacagacagt gaagtgcacc atcagcaggg 10320
tgattgatgg ctgcccctcta ctcgctctct gcatagcatg ctccttgagc ttcttgtgtc 10380
tttgtattag taagactatg gcaagttgcc agtaggacat caggagtttt tttgttcgac 10440
attaaaattt ccagagatga aaataaagct ccagagagga ggcagtacta tttattgttc 10500
agtagacctc atgacagttt tgcaatggtg attttcattc ctctctcaga attcatttca 10560
gagctaattt gaattcttta cacaagactc tggtctacat cagagatagt ctgtaactgt 10620
ttatattcaa gaataaaagt aaatataaat tactcaaatg aagaaaatta tttggatttc 10680
cagaaatgct tttgactgac tggtgttcta acagttctg ttttctctta acaatgttc 10740
aagccttaat cgagagcatc agcactcagc atgcaggctt cttacattat acctactaga 10800
tccccagcat aggcactcag catgtaatgc cttacaccac accaactagt acaaatggga 10860
aggtggaaat cgccttcctg tcttagcagt caatgactag atgtgacttc tttcacatga 10920
ttgcaggttg tcactgtgaa ctgtgctcga gtcatccatg ggaaccagat tgccacaaat 10980
ggtgtcgtcc atgtcattga ccgtgtcctg acacaaattg gtacctccat ccaagacttc 11040
cttgaagcag aagacgacct ttcatcattt agagtaagaa ccgtggcaga atcctctaag 11100
```

```
tcactgaaac gcttccttcc cctgacaaga tctgtagact gtcagaaaat gctactcaac    11160
agatctggca aactgcacca atatattcaa tgaaataacc atttctattt cacaaatgag    11220
agaccatccc acatatagta atagtacatg tttaaacatg attgataaag aaaggctctt    11280
tgtgtggcta cactatgatt ggaatcttta gaacatgttg gttcaatgac tatgcatgtt    11340
gttggatttt gctacaggcg gataaacact ggcagacttt ccattctagc caatggtttg    11400
aggagaatta gttgggccaa aaagtataat tttaaccatc taacaagagc agatgtctct    11460
ggtgaagctg tgaactccct cctgacacac taggccaagt gtgtgacaag tttcctttgg    11520
atttgccatg ccatcctcta aaagtcctct gtgtttcagg cagccgccat cacctctgac    11580
ctcttggagt cccttggaag agatggtcac ttcacgctct ttgctcccac caatgaagct    11640
ttcgagaaac tgccacgagg tgtcctagaa aggatcatgg gagacaaagt ggcttctgaa    11700
ggtaagaaaa tgtcttcctc tcccagaatt ctcccagaga cttaggatgg aggcaatgga    11760
aaaagaccag tcattgtcaa tgatgagagc tgtgatagga aagaccaaaa gcatttaatg    11820
tgaggtgctc tagaaaacat catgcaaagg attggaagaa taggcaagta tcactgttaa    11880
caaaaacagc tgtgaggctg cagtcatttg tgttgtttcc aagcaaatca gttacagatg    11940
tgatgaaagg gtgtaaggag ccaggggat ggctcagcac ttaagactgc tggctgctcc    12000
tacagaggtc ctgcgatcaa ttcccagcac actgcaggat tccaaggaat aggattctct    12060
cttctagctt ctgtaggcac cagacatgta tatggtgtgt aacatacat tcaggcaaac    12120 actcacactt ataaaacaaa ataaataaat cttttttaaa atcaaaaagg aaaattaatc    12180
aagtgtgggg gagtaatttt gggagtggtt ttaatatgga atgcctatta tacaatactt    12240
ttcagctcta attttatgct gaactgagaa agttatatgg ttcttttagc cactacatat    12300
cgattctcaa atgtacttgg atcttttcca acctcccttt caagagccaa atagtctttg    12360
ccttgtgcta actaatttta tacactcaat ctccaaatta agccgacaag cgttgaagat    12420
gtaagcctca atataatatc aagggtcaga gagattcccc caggtgctt tcatgaaact    12480 gtctgcattt tctaatgttg tctggggaaa atggcctgcc ttgccctcag gttctaaaac    12540
tatattctca atcatgacca gtcttttgga agtagttaat acaacattct atttgagtgt    12600
tttataagag tcatgactaa cgggtaattt cataaactgc tcaaaggctt ctccttttc    12660 tcttttcatt ccttttgtc ctcctgatgt tgcaaagaat aagtttgatt tttccacccc    12720
ttctctcccc agctctcatg aagtaccaca tcctaaatac cctccagtgc tctgaggcca    12780
tcactggagt agccgtgttt gagaccatgg aaggaaacac tattgagata gggtgcgaag    12840
gggacagtat ctccattaac ggaatcaaga tggtgaacaa gaaagacatt gtgactaaga    12900
atggtgtcat ccacctgatt gatgaagtcc tcattcctga ttctggtgag cagagcccag    12960
ccaccattcc ccttaccagt taaggtatct ggagagcaaa tccatgaaga tctaatgcat    13020
agctcaaaga acaaacagca aactgtctgt gcgctcacta agtgctaact ccaaagcctg    13080
ggcagccatg cacagcccat gcaggacctt ggcccagcat ctagtattta aagggtttt    13140 ttcacactgc tagtgtattg cttggcaaca gaaagatgac aaactgatgg taaacattaa    13200
gtaaagaaaa ggacttgcca ctcacaatgt agaacgggct gaaagttgag taatgttcac    13260
gaaaactaca ctaggacgac agagaaaaaa ctgcctccaa agtgatttga actgatcaaa    13320
ccccccacgt gaaaactaga accttcataa taaggaaggg aaggggtgt tttactgcat    13380 tgacactcaa gtaaatagct tacaagagta gaaaagagcc aggcactgat ttatgaacgc    13440
tgggagaggg atcgtaacaa tgaggacatt gttgaaatgg gaactgttta ttttacagcc    13500
```

```
aaacaagtta ttgagctggc tggaaaacag caaaccactt tcaccgacct ggtagcccaa    13560
ttaggcttgg catcctctct gaagccagat ggagagtaca ccttattagc acctgtgaac    13620
aatgcgttct ctggtacgtg ctgggttctg ttcccactcc cttcttcctt tcttccccct    13680
tgattattct caacaagaaa taatagatat tttagaaaat gttggttaga tttggtgatc    13740
tagaagatac cggggtcaag ttataaatgt agaaaatcaa gagacggtta cttgggacca    13800
tgatgtgaag tatgtttgtg tcatctagtt attggtactc actgacaata tttagggtat    13860
atggtaagat ctggttctaa aaccttattt cacaggcata tgaggaggaa gtgtttagtg    13920
aacaaaagtc aaatttttaa tatttttaaa tactaagttg taatatataa aatgattaat    13980
tagagagatt agaacttcta gaaatacagt attcccctta gaatgataat gagcatgtgt    14040
tctggatcta tgacacattc ggagtctgtg tgctttgatc ccttagccag tagtaagtat    14100
gaacttacat gtgactcatc aacagtcacc catgtgacta atggacacct gccagaaaaa    14160
tattggtaca ctataaaggt ttagattttg ccaatgacca ccatgaaagt aaacggtccc    14220
tatgtagatg aagttattgt ttgccaataa gggtggggtg ataggtcagt gtgtactgac    14280
agatggccat gttggctttg ggtgtctaac tgactctttc atgatgtgag tgaggggtac    14340
acttgcttga atagcattag agacatccaa gtttcttctc ctgccatgct ctctgtaggt    14400
gataatattc ctccctaata aatttattca cagatgacac tctgagcatg gaccaacgcc    14460
ttcttaagct aattctgcaa aatcacatat tgaaagtaaa agttggcctt agcgacctct    14520
acaatggaca gatactggaa accattggag gcaaacaact ccgagtcttt tgtgtatcgga    14580 cggtaggtga atcagactcg aaactaacat ccatctacag tggtctgaga gtcacatggc    14640
atatgctggt caaagaattg tcactaagaa tattcctcac acacatgcaa atgcaattgt    14700
aaaattaact gtccatatga tcagagataa agacatctca gcagaaggaa cttaggagag    14760
agtaccaatg tgctgtgaat cgcagataac tagcatttgt cccagttaac aagaaactat    14820
gttctgaaat actcatttaa atcccagaag attccccata gcgtaagcat ttgcctcata    14880
gaatactttg tattttatag gactgatttt tttaaaaatt aattttattt gtaattcatt    14940
tttttatact ccatattcca ttccccgccc ctccccatcc atcctctgac tgttccacat    15000
accccaccct gtctccacat ggatgcagct aaaaggcttc atggggaggg aagcattgcc    15060
tagaaatgga agtggcaggt ggtagctagc tctttactaa ggcttcagga tagcaaggca    15120
cacgtttcaa ataattcaga aagtgagctt cacttctaat tatatgtgta catatattaa    15180
attatacata tatatattaa acaacacata tatacacatt gaattataca tatgaataca    15240
gtgatatatg catgtacttt attattcttt atattagaca tctgaaatca ttaaattata    15300
catgtgcaca tattaaataa agcataggca tacatcaagt ttttaaaagt ggaattaaat    15360
taaggattag acatataatt gattggtctt acagtcaaga aaatttaatg aatgttaata    15420
ttatatgact cactgaattc tggaatattt atagctaata ttagcataaa gagtagctaa    15480
acatggaaca ggatgatggg gaaaaaacag aattagaatt ctatgcaaag tctgcagtct    15540
gctgacagaa tgcagaagcc tgatgcataa cgtggctggg ctggaggcag gaccagatga    15600
gaaatgcaca gtcaaatgtt caagacatta caaacaagag agaagaaact gccttctctg    15660
gcctagttac tctagtgacc tcctggaagg gctacctccc atcaaacaca caaggggca    15720 tcattggtct ttcctcccac tgctaggcta tctgcataga aaactcatgc atggtgagag    15780
gaagcaagca gggaaggaat ggtgccattc acatattccg agaaatcatc caaccagcag    15840
```

```
agaaatccct gcacgacaag ctgcggcaag acaagcgctt taggtaagcc taccacctgt   15900
gcctgtattg ctcactccaa tgatacaccc acaacacgac cctgacaccc aagacgaaaa   15960
cattcacaag acagtatccg tagattggga attacaggca attaatggct ggtgagggaa   16020
ggagaatcag ccttctccag tgaagagccc cctaacggga catctaaccc catgccagcc   16080
ctaaacacac acgcatatat cagcaacagt aaatggactc attaggctct gtgtgtgtgt   16140
gtgtgtgtgt gtgtgtgtgt gtgtgtgtgt gtgtgacagt aattaaagaa caggaggtca   16200
tgaattttaa gtgtggggac agcaacacag gaataaatag aggggagatg ggggatggaa   16260
atgatatgaa tacagtactc actaatgtaa ttctaaataa aaattaagtt gaaaattaaa   16320
attaaattga aaaatcatgc aaatatttta aaattaacac gtttcaatga tatttggttt   16380
gttcctgggg tatcatagta tgatttggtg ggtagaaaaa aaaatctaat aatctgattt   16440
actccttgag attttctta ttcttgtgta catggtaata aaaaaaagat ttttcaataa   16500
aatatgaaat gaaacaaggg ctttgtgtca cagaaaatgt gactttgatg cttttataag   16560
aaaagcgaag gtggagaaat tcaaattata tatttcagtc ctttcccat tataaatctt   16620 taacagggaa attgcaccta caaaaaatgt gtcagtgatt tctcgctgtt tcaataatat   16680
gtggattcca ccctgcgctg tacatggtta agtgaatcta aatctaactc ttatgtcaaa   16740
ctaaatgcat attctctgtg cttagcatct tcctcagcct ccttgaagct gcagatttga   16800
aagatctcct gacacagccc ggagattgga ccttgtttgc accaaccaat gatgccttca   16860
agggaatgac tagcgaagaa agggagcttc tgattggtga gtgaccatga atggcagatt   16920
ctgattggtg aggggcagtg aatggcagat tctgattggt gaatggcaga ttctgattgg   16980
tgagtgaccg tgaatggcag attctgattg gtgagtgacc gtgaatggca gattctgatt   17040
ggtgagggac agtgaatggc aaagtggttt ccttaactga ctttggtttc cattatccta   17100
cgtgggatgt gaggagagcc attcgttaat attattcaca aattgcttac tgtcatacta   17160
atttattgaa aaacatacaa ttgtatggta taaaggggaa ctgttttatt ttcaagacta   17220
atgggcacag tttgaattga ttgaaatgac taatgttttg ataaggcatt ggaatcggtg   17280
agaaaatgtt gaccttgtga aaaaaaaaaa aaaacagaa gaggaaaaag agacagtgta   17340
atgttttatt ccttagatct tgtatcaaaa tgtcagagaa gcaacacatt attaaatcaa   17400
tatctgtctt ttctgcaggg gataaaaatg ctctccaaaa catcattctt tatcacctga   17460
ccccaggggt ttatattgga aagggattcg aacccggagt cactaatatc ctgaagacca   17520
cacagggaag caaaatctat ctgaaaggag taagttgcta gaaggagttt atgaagtgct   17580
tatgatcatt aaatggtcta cacacggttt ctccttacca tcaccccctta ttttgaaagg   17640 taaacgaaac gcttctagtg aatgagttga agtccaaaga atctgacatc atgacgacaa   17700
atggtgtcat ccacgtcgtg gacaaactcc tctatccagc aggtctgtaa agattaaaca   17760
cgctgataga ctgctcaaaa tgagcttggg ttgttttgtg ggtgttgtt gttgttgttg   17820 ttgttgttgt tgttgttgtt tttctttaat cacccatttt cttaccatac tcactgagtg   17880
tttatctccg tagatattcc agttggaaat gatcagctct ggaattact gaacaaactg   17940 ataaaataca tccaaatcaa ggtacagaac gctatcgat tttatttcta atatgtcaag   18000
actgtattgt ggggttaata taaagactaa gaaattagtg tagtggatta ctagtatacc   18060
actggtataa tgtagaaaat aggaaaaata taggatatta tgtatattta acattggtta   18120
attactttat aatcttaaaa ctcttagtaa taggcctgat tgttttgatg gcacctgatc   18180
tgacttcatt tctactgagt gaccttaact attttttattt tagttagaat tacagtgttc   18240
```

```
ttggtgtgca atacactttc tgtaactaaa cataaacatt tattttcagt ttgttcgtgg    18300
cagcaccttc aaagaaatcc ccatgactgt ctatagtaag tatatgaaca gcttgggcta    18360
caaatagaga tgatatgcaa ataacttctc tttgcatata caaagtctgc tgataatctg    18420
gtatttagga ttccaaattc tctgaaactc attatccttc aaacagggcc tgagatcagc    18480
agaagcctta aaggcttagc cacaccctcc gagtccactg aaccgaggga agtcaattaa    18540
aagggcataa aaaggacagg atactagaag acaccccaga gctttctgga aatgttaatg    18600
agtgtacata aacacagcag cacagcagag ggctgccact tatcctgccc tgggcctgag    18660
ctgtgcatag gaagatgtgc agagggtgct aattttccc attaattaat taattaatta    18720
attaattaac tttacatccc cattgcagcc caccacctcc cagtccaagc ctcacatagc    18780 ccctccctc gccctcctcc ttccctctg agaacctgag aggtccctcc tggggaacca    18840
gccctctctg gcacctcaag tcactgcagg actaagtaca tttctctcct aattcttatg    18900
agatgctggt tcaaaaaatt accacatcca aaactgggca aaggaacctc aaatctgcta    18960
agcagttatg ttttaagccc ctacagtacc agattatcaa gatcaaagtt caacttctta    19020
accatggcaa ggacatttca ctctaatcat aaatgctgct gtcaaccatc aaatagcttc    19080
ctcattgtgg tttctcgttc ctacctacct ctctaccctg cttcttttac tgtagctttt    19140
aaagctgaag ttcttttcat tttgttttgg ctctactcca aaacagtcaa atatggtgaa    19200
atgttactcc cctttattct aactagaaaa ttattctact cagtatcatg aacatccttt    19260
tatctattat gagcattgtc cttcaaaatt aatgctggtc atgaaaagga gaaaagccaa    19320
tgtatggagc aaaacaaaat gtctgcttct ctacttgata taacctctgc catggtggtg    19380
ccagaccctg agagctatct aagggattcc actagaatca tgatgattta gcattttcta    19440
aattccagcc atggaaatat atatcttata ataaatacaa gagtcctcat ggcctccatc    19500
catcagatat aaatgacacc atccttctcc cctgtgccat aaatccttag gaaagtagta    19560
tttatccttc ttagtttatc tacatccatt ctattactgg ctgcacatgg caacatggct    19620
tataatgaac caaaatacta ttatagtatt tcataaacta tgtctacaaa attatgtaaa    19680
tctagtaact tgccagccca ctcaaaggcc ttacggagct atgggattta tatccttatg    19740
ctggctgttt caaatagagg tacaggccga ataaaacaaa gattccattt tcagaatcat    19800
ttgttaattt gtctctatta tttcttctgt tttgttggta cttatttttc ttgtcccctc    19860
aaaaatacca cacattttaa attttattg ggagcacact tgttataag ttgtcaaatg    19920 caaaatgatt ttacatagag gacaaagatc aggaaatctt tagagctgtt caaatgactt    19980
aagccttcac aaaagcaaaa ctgtcaatta tgaccctcaa gttcaaattc cctagcacgt    20040
aaaaccttaa aagtgattaa tgtttccact tgaacaacag cagcaggtct ctgtgttgct    20100
ccaggggcag agtcctctat ggcagaacca cttatgagat caagaactga gcatgcagat    20160
ttgacacatt ttagagcttt atagtctgag ttttcaaga gatgatctat ggttgaaagg    20220
tagtccccat aaaagaggag cccacaccca ttcaagaggt tgacatggct tagcatgtaa    20280
gagcaggggc agagactggt agaaatccac agtgtgctac tgactctttg tcacacgcat    20340
gactgaagtt ggcaacccctt ctactggaat caccttttaa ggcttctact taggagtgca    20400
gaggcctaag tagaactggt gacctggctc ttacataaaa ataaaataaa aacaaccaac    20460
aaacaaacaa gcataaaacc atccatccaa cctaaatcca tgatagcctc acttgggaga    20520
tgatatacat tcatcataaa acctttacat ggaaacctac cttaaaatta tcaaaacaag    20580
```

```
gctaaaaatt aaatgttgac caactcacat ctgttgcaaa aagctcatga cttcctggct   20640
gaaatttatc ctcatctcaa attgtgaatt catttccata ttctcttttc tgtgccaaat   20700
gcatgggagt attccatggg tcttttcctt cccatatcct cctttaatt gagaaataag   20760 ctgacaaagc aatttaagat agtatgaact gcatgagatt aatcatgttt atttgtcttc   20820
tgttgctgtg cagccagtgt tctcaagaag cacaagggga agtcagagcc ttagtgatgc   20880
agttgagagt ggtagatttc tagatgggat gtggcattta gttagcatgt cttcccctcg   20940
ggaacgtagc caagtcactg acctgcagga ttcagcatct ggatatgaga agacattaat   21000
gtgctgtgac tatttcctgt gactgcctga ccctagcacc agagctgata aattaacgcc   21060
tgatagagac caaaaaggac aactttatcc gagttgtttc tagttaaact tcgttcatgc   21120
tccactttct atgttttcag caactaaaat tataaccaaa gtcgtggaac caaaaattaa   21180
agtcattcaa ggcagtcttc agcctattat caaaacggaa ggtaaagcca cactctcca    21240 tggttcctta cattctggaa aaacatatc atgtaatcaa ctcatctctc tgaatatacc    21300
tacattcttt ttgaaactaa catgctaaac gtttctctac aaatggcatg cttgtgtaat   21360
tgcagattgt ggagtgcaat attttttta gcaaaataga tggtgcatcc ctaatattt     21420 cagtacattt gcttgtattt attttgatct aattgaggtt gtgtcaacac tggtacccag   21480
ataatcactt aaaaattaat catgaatatt tttgctgtag attccttcag aaaatatact   21540
ttctgtagct ttatttccac cctttcatca ccatcgcaca ttcactttat accactgaaa   21600
gaacattgct taaaactaca caggcatcct ttccaatgag aattctaaaa gggtatagaa   21660
ggtgtacact catgaaagct ttaaaaatta caattaacaa atcctttaaa acattagatt   21720
acgaaagcag aaaatagtgt tatttagtag gtcaaactct ggatcctaca tctcatctct   21780
gaacatactt tatataacctc tcatgtttca aatgtcaatg tgtttctata cttactatat   21840
taactgatgt caaccttgag caacagtgtc cactttcatg cttgttgcag tgataatttg   21900
ccacagcgaa cacatctgct gtcatctttc ttccatgaga atgatgcaaa cagtcttct    21960 ttttgtgtc tatatttttt taaattcatg ttacatccca attgcagctc agtctttcaa    22020
aagaggaaca gattatgctt tattgaatct taggaactct gttgttctaa ttgtccttgt   22080
atttgggttt cttgtgctt gttttcatt ctgtggcatg agatgccaac tcaaaataca    22140
tgtgtctctt cccttaggca accctgactt aaactcgttg aaaacataaa gttgattctc   22200
tgactggcta gctatgggtg tcattcattc ttgagtctac agttgagtca tcctttagaa   22260
tctgtgctta gcttaaaaaa aaagaatttc aattattcca ttgcttttta tttattgatg   22320
agtaaaaaaa attggggttt taagtagaaa ttaaatctaa agtgttttga tggcaatata   22380
tatttgattg ttagtgaaaa ttatcaacca aatttaggca aaaatattgg atgtttttta   22440
aatcatagtc aataaaattt gctataactg atacacagct tctaaaacta aagtcatccg   22500
caggtgccat tgtcccattt ccaaacactt ttctccttcc attcaacttc ttcactcaac   22560
tcatgtgtcc tcccagtctt tgtcaacagg ggtatgtgtg tccctcttca gttgggagca   22620
tccttgagca tcagtctacc tggggttctc cctcataatt atctagaggg tgatagggtc   22680
atctcatctg caaatattct tcattgtagg accataaaac aacatttcta tgttgcagca   22740
tctcaaagca gagaaatgtc catccccaga gtccacccat ggctctcatc ctctctcagc   22800
atttgaactc tatgggttca atgatgcttt ttgggttctt actaaatgtg tcagagtcca   22860
agacataatt ttatgatttt ttttgtcaaa aagcactaa atcaaaattc agaattaaga   22920
acaagtcatc taaaacttaa caaatgaaat atctatttca tatatatgta tataaaacat   22980
```

```
ctagtaaaaa tttcttcttt tgtagtattt gataataggt gcttccagaa tttcaacttg    23040
gcttttgtaa agaaaaaaaa atgcctcagt cacagtgcta actcatttcc ttgtcttgag    23100
tcactgggca tacttccttt tgagggttat cacatgttaa aacctattca tacctttatg    23160
ctaaccattc ctactggact cacgtagaaa acactacggc ctgaaatact tacaggttaa    23220
aagaacctta ctatatagca ataatgtctt acattattca tcatttatta cctagttctg    23280
ggtaatggtg tactttgatg atttctcaat aaacaaatca atcctctcaa gatgagtaat    23340
tataactcca ttcagctatt gagaagtaca agttaaatgt actgaactga ataattctca    23400
ctgctccata aaatattcct gatcaactaa tgtagcagta agctttctaa cattcaaact    23460
gattttctct gggaataaaa tcactttgca agtcaaactc aaccccctgt gcttttgaag    23520
gatgtgtaac tgttagtgat gctggtcctt acatccttct cctagtccag gtaagtacac    23580
aagtcagttt tcctctaagg cctaaagcat agcatcttca aggtaagtag agtagatttc    23640
tttatgtcca gtgctatact cattgataat gtaagatcag gaatgataaa aagcattaaa    23700
taaaatatgt tagcaaagat tggcgcgtga tgtcctctgg aaaagtgtga tttgaaccag    23760
ttgccacttg agcgtctcca atctgtaaat gctgattccc agagaaagcc acataataca    23820
ttctctgtaa tcataccttta tagtcactaa cgagggatga cggtgtgcat gcacggcttg    23880
ctcgtgcatc actgtaaatg ctaaagtggg ggtggggaag ctgcagcata ctgaatcctt    23940
tggttcccca atattgtct aacctaaaaa caacaggaaa tgtttaaaac tggtttcata    24000
aaacctgaaa cactgaagtc tgaataacaa gaaacgtgga aataaattta ctctttggga    24060
aagtttaagg gattgcttca atgcactaat ctgtctcctc taaaataata tctcaggacc    24120
tgcaatgacg aagatccaaa ttgaaggtga tcccgacttc aggctgatta aagaaggcga    24180
aacggtgaca gaagtgatcc acggaggtac tttatgcctt ctgcttttc ttatgctggg    24240 gcagcatccc cggaacgttt taaagtagtt ttgatttaga atttttcaac agcgaatttt    24300
atcttgatct aaactttaca caagttgaga aatttgtttt actaggtatg agttcttgct    24360
agctaatcag gaatatagtg tagctcgttt ttaagtgtgt tcaataataa aggattaagc    24420
tcctggatca cttcttatta atatgcaaaa atggcagtca tgaagtataa ggatcacaat    24480
aatgtcaaca cacaaagaca tattgttctc agaagagaag gggttgatgg ttttttttgta    24540 agactctggt aataagggct ggtgagatgg gttagtaggg aaagatatct tcttccgagc    24600
ctatgttaga tccttgggtc ccaaatggtg aaaggaatta agttgtctcg tgacctccac    24660
aggtacacca tagcttacac acacaaacac acacgcacac acacacacag aatcacataa    24720
tacatacaca cactcacata atatacacac atacagacac ttgcacacac attcacatat    24780
gtacacatat acatacatat atacatgcac acatatgaac acacgtacat acacacacaa    24840
acatgcatat attcatgcac atgcacacaa acagacacac acatacacac acacacacac    24900
acacacgccc taagtaaaat gaaattgcaa taaaccttt agagactgtc ctaataaacc    24960
agcactgggt tttctaggaa ggtttccttt ccaatgacag ctcagcttgc cagttaaccc    25020
tcctgctcac ctgagacaca agagttactc agactgacca ggatttgctc ctagtctgtt    25080
ccaacaatgg ctagggctgt tcttaaaca aacgtgttat gagaaacaca tccttgattt    25140
aaatctccag ctctggaggt atagacactg tgagaggata agtcccgtgt ggtattcttt    25200
ctcttctttc agagccagtc attaaaaagt acaccaaaat catagatgga gttcctgttg    25260
aaataactga aaaacagact cgggaagaac gaatcattac aggtaatttt taatttata    25320
```

-continued

| | | | | | |
|---|---|---|---|---|---|
| tatgagctgt | atccagatta | taaacacaag | ttatattaac | cctaggatgt | gtgcattaca | 25380 |
| caaatctagc | ctttgtcatg | gtgacaattg | aagcttctcc | atttcccatt | ttgtttttg | 25440 |
| caaacaaaaa | gaaaaagaa | aatgtacaaa | atatgttacc | cctctcttac | tctaagactt | 25500 |
| ttggtagaca | tgtctgtaaa | catgcatttt | tactctgtgt | acacatacat | gctttatgat | 25560 |
| attctgcctt | tcttttacag | cttcccaagt | tactgaatac | taaaagaaac | ttcctttggg | 25620 |
| gttctattca | tgctacagtc | tgtacatcta | catagcatcg | tgtatatgag | tctctctaaa | 25680 |
| acagctgaca | aatttagtaa | actttgtgtg | agacttacat | cgatgattta | acctaaaatt | 25740 |
| ctaaattcaa | tattctatat | actttattta | aagaagccca | caaatacagc | ctgtgcctca | 25800 |
| tattttgcaa | taagctttc | tggagcacag | ccttggccat | cattggtatc | gtgcctgcag | 25860 |
| ctacactcac | tcagaggagc | tgaatggtcg | cagcacagac | gtgtgcccac | acagcctaaa | 25920 |
| accctctttc | ctttaggtcc | tgagataaaa | tataccagga | tttccacagg | aggtggagaa | 25980 |
| acaggagaga | ccttgcagaa | attcttgcaa | aaaggtcagt | atgtctagag | aagcaagagt | 26040 |
| gtggcactga | gccacctgtc | ccctatctca | catcagcttg | aagactgaga | acatgtctta | 26100 |
| taccaccttg | ctccaggatt | catattccac | accagcataa | ggggtcattc | aaaaatagag | 26160 |
| atgatgccag | atatggtacc | cacgcagatg | gtttgctggt | atagcaatgg | cagccatctt | 26220 |
| acattgcctg | tataatgatt | aactgctgat | gaaaacactg | taccagacac | caacactaaa | 26280 |
| aacttaggag | ttgttgagaa | gtgtctggaa | ttccctactg | agcaggtggc | agcatgcatt | 26340 |
| gtgtcaaatt | ccttttatt | gtgtgaccca | atttctgctg | tgaacatgtg | tcctctcaga | 26400 |
| ggtctccaag | gtcacaaagt | tcattgaagg | tggcgatggt | cacttatttg | aagatgagga | 26460 |
| gattaaaaga | ctgcttcagg | gaggttagta | aacatcgaaa | actaaccccc | ttaacaggcg | 26520 |
| ctggaagaga | gcttcagctt | tttaaagact | ggacatgtag | gctggtcctt | tcattcgatt | 26580 |
| aaaaagacag | cgccgtctgc | tgtcttcggc | aaattgactc | gtgtgtgtaa | gtggtcagtc | 26640 |
| cagaaagtca | ttaaatctta | aacctgctta | aacagtcttt | aaaaagtttt | atgatgtaaa | 26700 |
| acctggaagc | agtgaatact | ttttttgcc | ttgactcaga | aaacgaaaca | gatattttga | 26760 |
| ctatatgaaa | aagtaatgat | tttgctacct | ggcagacaag | tttaaatttg | aaaatgcttt | 26820 |
| tcatgtttct | aaaaaatcgt | attcactgtc | cccataacaa | agacaggcat | gtttgggagt | 26880 |
| ttgtaagtgc | gtagttaagc | attaaaaagt | gcttttagca | acttgcattt | ccaaagctac | 26940 |
| attcttacaa | gtgaatatgt | attccttctt | actgtttgag | ggacaatcta | tactcaggat | 27000 |
| tacaaaatct | ttagcatata | aaattaatct | ttgaggtatg | gaatgtcctc | tgtctgtggc | 27060 |
| attaaattga | cttactttca | aaaggaaaaa | aaggattcaa | aatatacaaa | ctctcagtga | 27120 |
| tagttattca | aaaataggaa | atgttttaaa | aatcattggg | accattgaca | gctaaataaa | 27180 |
| cgcatattta | gttcaattta | ctaacaacaa | acatcagac | taaaaattat | tcagagtaca | 27240 |
| agcaaataga | tatctacaac | aaatctgttc | tttccagtat | gttatggatc | aagaaagaca | 27300 |
| gttgaaatct | gatgtttacc | taaaatccag | ttcggatggc | ttttggttga | taatttaaaa | 27360 |
| agttgtataa | ctatgtctaa | gaaaatataa | tttctcttcc | atcttaaatc | ttgtatattt | 27420 |
| ctggattggt | gaaataattc | ttcattcaaa | caacagtgta | tttttaagta | tacattcaca | 27480 |
| tatatctaga | aagtattaga | cttcctttca | gactgcagga | agcctgtggt | atatccttag | 27540 |
| ccatgatgaa | accaatggct | tcttgacgat | gcagcaaagg | acccactaag | tgcctccctg | 27600 |
| ctataaaacc | atagcagacc | ttaaaggaag | agtgaacaca | ttgaggaatt | taatttgaat | 27660 |
| cctttgtttt | tctttataac | ccttgccata | gtcagcagct | ttgtggaatg | gctgtgcttt | 27720 |

```
ctagagaatt tattagagct tgtccctatt tatattgttt ctccttgtag gattaaataa   27780
tgggtaagta tgtttgtccc ctttaattag taagactctg aaagtcttct ttgaaactga   27840
acttaaatat taaaaaaaac ttattcccct tcccaggata tatgtccatt taaaaaatgg   27900
tgttttctct ttaattaatg gggttatttt aatttctgtt gttctcagtt tctttacttc   27960
tatggatatg acctgtctat agatctatgg ggaatgggtt ccaagagtgc caatttagaa   28020
ggtttagcaa actatttta aggattttc ttttcttaaa aaggaggatg tgggcctgga    28080
gagatggatc tgagcttaag aacactcatt gctctctcag ggtaacaggc tctgtttctc   28140
agcttccaca gagcagcctg gactgccttt aactccagtt ccaggggctc tggcatcctt   28200
ttctggtctc cacaggtact acatacaaat gatgcatata aactcacacc catgcacaca   28260
catacataca cataataaat agaggaggcc tttaaaagat gtactatagt aactagtgtg   28320
tgcgatgtag tttctagcat ctgggcctga gctagataag ttacctttct ctttctagct   28380
ctctaaatgt ttcttctccc acatccactg gagagtcact tcctaacact ttcatgttga   28440
gatatctgag agccaggaaa gtaaactcgg gctctgagtt ttactagaat ttcattctga   28500
gatgtttctg aacctcattg aacatttcta atttggatgc tgccatagca gagtaataat   28560
aattggtaaa aataaaaaaa taaaaaaaaa cacctcattg tcagactcta ccaaattttt   28620
gtaaggatat ctgaaagcag ttgtccattt gaaaagggaa tctagaagat tcttttgaa    28680
cctgatatca acttttcaat caaatataat ttaataaact tactataaac catacccta    28740
ttcaatattt aaggttacat catctatttc attgtgatga tactttataa accattattt   28800
tattatcaaa taaactttta gttaaggaaa atgtttattt gatatgcttt aacttagatg   28860
ttctaattca atggcatttt cctcttatta gccaatctca aagggtttc tgtggttctg    28920
tgtctaacca tagtgctaac atattatgac aaatagttgc acgccttatg gagaattcac   28980
atgttggaaa tgtattaaga ctgggacaaa gctcataaat tatttaaaat atagtggggt   29040
ttttttccat ttgctttctt ttgtacatct tgcactaagt ctagtgcaag catttttcaa   29100
atgtacaaaa ttgaaaaaaa accaataaag aaaaatggtt ttattgttaa atattgatga   29160
tacacacaaa ccaagtaaag ttttaaagga aagtaaaatg gaggcaatcc aaaaaaatga   29220
aactaccata ggaaccaatc agtctttaat cccagttacc ctcaaaatga aggtaaagtg   29280
tgatcttagg cttactaggt agtcacgaca ggagttagat taaaacgatt agagaattgt   29340
tttctaacta taaaaacaca aaccatatga acactttgaa aaatggagaa cactggggct   29400
ggagagatgg cttgatggtt aaaagcactg actgctcttc ccaagagtct aggtttgaga   29460
ccaagccccc aaatgacagt tcacatctgt ctgtaactcg agatcgatgg gctctacact   29520
gctgtgctct gcagacactg gcacacatg tggtgcacag acatatgtgc ttctaaaaca    29580
tccctaaaca taaagaaaat gtaaagaaaa gtgaaaagtt ttaatatttt tatacctagt   29640
taatttgtca atggtttatt ggatggacca tggaatcagg gggaatggac acaggtacac   29700
ttctaaattg ctcatggtct ataatgaaaa ttttacagag gcacatatat gcataataa    29760
actgaaatat gggtagctct cttggaaggt agtgtcacat tttaccaaaa tgtcagcgat   29820
aggaaaacca attaaaggat tccaagagac acaataaaac acgctatgtt ggtgaacatt   29880
cactatgatg catgagaagc agatggcttg gcaggaagtg aaagtctaag gatcagtaag   29940
tttactactc aaacaactac acattgaagc aatgcctaca tatactttac actttttctgc  30000
ttggcaaggg cctccggatt ttaccaggaa tcccaaagca tttctaacta tgtgtcttta   30060
```

```
attttagaca cacctgcaaa gaagatacca gccaacaaaa gggttcaagg taggtgaatc   30120
aactaaatta atacatgttt gagatatgtt tgatgatgtt agtgacagag aggggtgttt   30180
aatgcagttt gttgagtttt gggtttggac agacagaaaa tttagtgaga tctgatgcaa   30240
agtttgctgt gataagtgtc aagaagtcaa cagtatatgt tctcctttat tatctgactt   30300
aagttgaaca aaccttaaaa ggatggcaga tagacttgta taaatggtta aaagtgccga   30360
accactgagt taagtcagaa agaaatgctg gcgctacagt tgagacagaa gccaattaat   30420
agttaaataa gcacttatct aacttaatcc tctattgcat atatgatgtt tacaatataa   30480
tttcttccat ttatgtcaat tttctaatat tttctcttaa gtaagtaaac atatatgtac   30540
tgaaagagca aagattttct ttgtagtact cacaaacatt gaattgaaag tctcaaattc   30600
ttgagataat tgcacactaa taataaaaag aactcataag attcataaat acagtacatg   30660
aagatctgac tttaagccaa cccagcatat agaatgttga cactaagaag ccagttgcat   30720 atgttttttaa ttaaaagatt tattaagagt ttatataggc acacaagact acttcaagtt   30780
tctagaaact caaaatcatt gaattttata ttttaataca cctttaatta aggcattcag   30840
tctttcttac cctaaagtga agatagtatt cagacaacat gatctaaata aatcttatta   30900
caaggagcaa tggtcacttt tgacagatat gtgtgtgcca tgagattttg tcctagtctc   30960
ttctaactgc tctcatttcc ttctcctcag ggcctagaag acgatcaaga gaaggccgtt   31020
ctcagtgaaa acccagaggc cagaccacag agtttatata atcctaaatc aacgatctga   31080
ttttaaggga aattgtaaga gccaccacac tgacttcaga atctgaaatg acaaccaaca   31140
gaagccaatc ttcaagcaag tccaaacaca gagttcatgt ctttgtttct gcatgagaaa   31200
tataagaaaa tgatagctag tctcctgtgg ggtaggaact gaggaaatat aggaccatgc   31260
agggatttta tctcaatgag aaaacttctg attaaagtag aatccaccaa agaacatcat   31320
tgtgactggg tccatacagc taagtctttg cacagtaaaa accttccgcc tcaggaagag   31380
gctgaaaaaa cccaaagcac acagttacct ttccagggga ggctaaggta tcaaaagggg   31440
tgttcagtta tacaacatgc aaacaaacct accaaattac gaacagtggt gttacatatt   31500
tctcatgcaa tgtgggtttc ctgctaaatt ttgttatttt tacacttgat ttatatcctc   31560
gagatgattg tcataagctt cttgcaatac aaatgttttc tctcaaacat ttcaataaaa   31620
ccattcttca ggtataaaga gaattactgc agagttggta attcagaaaa ctcaaggttt   31680
aagttaaaag tgagtttaga ctttggaata ggacttcata ccttttttta ttgttaacaa   31740
gtactcaata aaggaaactg aataaactaa                                    31770
```

<210> SEQ ID NO 3
<211> LENGTH: 30
<212> TYPE: DNA
<213> ORGANISM: Artificial sequence
<220> FEATURE:
<223> OTHER INFORMATION: Antisense Oligonucleotide

<400> SEQUENCE: 3

```
ccatgtataa cattgatttt taccttcagt                                    30
```

<210> SEQ ID NO 4
<211> LENGTH: 25
<212> TYPE: DNA
<213> ORGANISM: Artificial sequence
<220> FEATURE:
<223> OTHER INFORMATION: Antisense Oligonucleotide

<400> SEQUENCE: 4

```
ttgttgtcct tttactaacc tccct                                           25

<210> SEQ ID NO 5
<211> LENGTH: 25
<212> TYPE: DNA
<213> ORGANISM: Artificial sequence
<220> FEATURE:
<223> OTHER INFORMATION: Antisense Oligonucleotide

<400> SEQUENCE: 5
tgctgaaaac atagaaagtg gagca                                           25

<210> SEQ ID NO 6
<211> LENGTH: 25
<212> TYPE: DNA
<213> ORGANISM: Artificial sequence
<220> FEATURE:
<223> OTHER INFORMATION: Antisense Oligonucleotide

<400> SEQUENCE: 6
cctcttacct cagttacaat ttata                                           25

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
ataaccaaag tcgtggaacc                                                 20

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
tgtctccctg aagcagtctt                                                 20

<210> SEQ ID NO 9
<211> LENGTH: 21
<212> TYPE: DNA
<213> ORGANISM: Artificial sequence
<220> FEATURE:
<223> OTHER INFORMATION: Primer

<400> SEQUENCE: 9
ccatgactgt ctatagacct g                                               21

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
tgtctccctg aagcagtctt                                                 20

<210> SEQ ID NO 11
<211> LENGTH: 20
<212> TYPE: DNA
```

```
<213> ORGANISM: Artificial sequence
<220> FEATURE:
<223> OTHER INFORMATION: Primer

<400> SEQUENCE: 11
ataaccaaag tcgtggaacc                                               20

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
tttgcaggtg tgtcttttttg                                              20

<210> SEQ ID NO 13
<211> LENGTH: 21
<212> TYPE: DNA
<213> ORGANISM: Artificial sequence
<220> FEATURE:
<223> OTHER INFORMATION: Primer

<400> SEQUENCE: 13
ccccatgact gtctatagac c                                             21

<210> SEQ ID NO 14
<211> LENGTH: 21
<212> TYPE: DNA
<213> ORGANISM: Artificial sequence
<220> FEATURE:
<223> OTHER INFORMATION: Primer

<400> SEQUENCE: 14
ttctttgcag gtgtgtcttt t                                             21

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
ttctcctggc aaagacggac                                               20

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
cggccaccat cttgagactt                                               20

<210> SEQ ID NO 17
<211> LENGTH: 21
<212> TYPE: DNA
<213> ORGANISM: Artificial sequence
<220> FEATURE:
<223> OTHER INFORMATION: Primer

<400> SEQUENCE: 17
ccctggagaa gagctacgaa c                                             21
```

```
<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18
taccccctga caggacgttg                                               20

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19
acggcatgga tctcaaagac                                               20

<210> SEQ ID NO 20
<211> LENGTH: 20
<212> TYPE: DNA
<213> ORGANISM: Artificial sequence
<220> FEATURE:
<223> OTHER INFORMATION: Primer

<400> SEQUENCE: 20
agatagcaaa tcggctgacg                                               20

<210> SEQ ID NO 21
<211> LENGTH: 20
<212> TYPE: DNA
<213> ORGANISM: Artificial sequence
<220> FEATURE:
<223> OTHER INFORMATION: Primer

<400> SEQUENCE: 21
caagcaatac ccaaagaaga                                               20

<210> SEQ ID NO 22
<211> LENGTH: 18
<212> TYPE: DNA
<213> ORGANISM: Artificial sequence
<220> FEATURE:
<223> OTHER INFORMATION: Primer

<400> SEQUENCE: 22
gaacagtcca gcccatac                                                 18

<210> SEQ ID NO 23
<211> LENGTH: 20
<212> TYPE: DNA
<213> ORGANISM: Artificial sequence
<220> FEATURE:
<223> OTHER INFORMATION: Primer

<400> SEQUENCE: 23
tgcgcttgca gagattaaaa                                               20

<210> SEQ ID NO 24
<211> LENGTH: 20
<212> TYPE: DNA
<213> ORGANISM: Artificial sequence
<220> FEATURE:
```

```
<223> OTHER INFORMATION: Primer

<400> SEQUENCE: 24
cgtcaaaaga cagccactca                                                    20

<210> SEQ ID NO 25
<211> LENGTH: 20
<212> TYPE: DNA
<213> ORGANISM: Artificial sequence
<220> FEATURE:
<223> OTHER INFORMATION: Primer

<400> SEQUENCE: 25
agcccaacta tagcgagctg                                                    20

<210> SEQ ID NO 26
<211> LENGTH: 20
<212> TYPE: DNA
<213> ORGANISM: Artificial sequence
<220> FEATURE:
<223> OTHER INFORMATION: Primer

<400> SEQUENCE: 26
gggtaccagg agagagtccc                                                    20

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
tccatcctat gttgcggtcg                                                    20

<210> SEQ ID NO 28
<211> LENGTH: 20
<212> TYPE: DNA
<213> ORGANISM: Artificial sequence
<220> FEATURE:
<223> OTHER INFORMATION: Primer

<400> SEQUENCE: 28
aaccgctcca catacagtcc                                                    20

<210> SEQ ID NO 29
<211> LENGTH: 20
<212> TYPE: DNA
<213> ORGANISM: Artificial sequence
<220> FEATURE:
<223> OTHER INFORMATION: Primer

<400> SEQUENCE: 29
agggcctctt ctgcgatttc                                                    20

<210> SEQ ID NO 30
<211> LENGTH: 20
<212> TYPE: DNA
<213> ORGANISM: Artificial sequence
<220> FEATURE:
<223> OTHER INFORMATION: Primer

<400> SEQUENCE: 30
ctttggaagg actcaccgct                                                    20
```

```
<210> SEQ ID NO 31
<211> LENGTH: 19
<212> TYPE: DNA
<213> ORGANISM: Artificial sequence
<220> FEATURE:
<223> OTHER INFORMATION: Primer

<400> SEQUENCE: 31
aaccaaagtt gtggaacca                                                   19

<210> SEQ ID NO 32
<211> LENGTH: 25
<212> TYPE: DNA
<213> ORGANISM: Artificial sequence
<220> FEATURE:
<223> OTHER INFORMATION: Primer

<400> SEQUENCE: 32
atccccgtga ctgtctatag accca                                            25

<210> SEQ ID NO 33
<211> LENGTH: 25
<212> TYPE: DNA
<213> ORGANISM: Artificial sequence
<220> FEATURE:
<223> OTHER INFORMATION: Primer

<400> SEQUENCE: 33
atccccgtga ctgtctataa gccaa                                            25

<210> SEQ ID NO 34
<211> LENGTH: 20
<212> TYPE: DNA
<213> ORGANISM: Artificial sequence
<220> FEATURE:
<223> OTHER INFORMATION: Primer

<400> SEQUENCE: 34
gaccatcacc accttcaatg                                                  20

<210> SEQ ID NO 35
<211> LENGTH: 22
<212> TYPE: DNA
<213> ORGANISM: Artificial sequence
<220> FEATURE:
<223> OTHER INFORMATION: Primer

<400> SEQUENCE: 35
ggtcaccaag gtcaccaaat tc                                               22

<210> SEQ ID NO 36
<211> LENGTH: 22
<212> TYPE: DNA
<213> ORGANISM: Artificial sequence
<220> FEATURE:
<223> OTHER INFORMATION: Primer

<400> SEQUENCE: 36
gttacaagaa gacacacccg tg                                               22

<210> SEQ ID NO 37
<211> LENGTH: 23
<212> TYPE: DNA
<213> ORGANISM: Artificial sequence
<220> FEATURE:
<223> OTHER INFORMATION: Primer
```

```
<400> SEQUENCE: 37
cctgaagtca acttggctct cac                                          23

<210> SEQ ID NO 38
<211> LENGTH: 22
<212> TYPE: DNA
<213> ORGANISM: Artificial sequence
<220> FEATURE:
<223> OTHER INFORMATION: Primer

<400> SEQUENCE: 38
agcctattat caaaactgaa gg                                           22

<210> SEQ ID NO 39
<211> LENGTH: 21
<212> TYPE: DNA
<213> ORGANISM: Artificial sequence
<220> FEATURE:
<223> OTHER INFORMATION: Primer

<400> SEQUENCE: 39
gtctccctga agcagtcttt t                                            21

<210> SEQ ID NO 40
<211> LENGTH: 20
<212> TYPE: DNA
<213> ORGANISM: Artificial sequence
<220> FEATURE:
<223> OTHER INFORMATION: Primer

<400> SEQUENCE: 40
caatgagctt cgtgttgccc                                              20

<210> SEQ ID NO 41
<211> LENGTH: 20
<212> TYPE: DNA
<213> ORGANISM: Artificial sequence
<220> FEATURE:
<223> OTHER INFORMATION: Primer

<400> SEQUENCE: 41
catagagaga cagcaccgcc                                              20

<210> SEQ ID NO 42
<211> LENGTH: 20
<212> TYPE: DNA
<213> ORGANISM: Artificial sequence
<220> FEATURE:
<223> OTHER INFORMATION: Primer

<400> SEQUENCE: 42
gctgacctcc ctgtcagatg                                              20

<210> SEQ ID NO 43
<211> LENGTH: 20
<212> TYPE: DNA
<213> ORGANISM: Artificial sequence
<220> FEATURE:
<223> OTHER INFORMATION: Primer

<400> SEQUENCE: 43
gcacccaggc tgaggtattc                                              20

<210> SEQ ID NO 44
<211> LENGTH: 22
```

```
<212> TYPE: DNA
<213> ORGANISM: Artificial sequence
<220> FEATURE:
<223> OTHER INFORMATION: Primer

<400> SEQUENCE: 44
atgagcactg aaagcatgat cc                                              22

<210> SEQ ID NO 45
<211> LENGTH: 22
<212> TYPE: DNA
<213> ORGANISM: Artificial sequence
<220> FEATURE:
<223> OTHER INFORMATION: Primer

<400> SEQUENCE: 45
gagggctgat tagagagagg tc                                              22

<210> SEQ ID NO 46
<211> LENGTH: 20
<212> TYPE: DNA
<213> ORGANISM: Artificial sequence
<220> FEATURE:
<223> OTHER INFORMATION: Primer

<400> SEQUENCE: 46
agtgcatccg tactcccaaa                                                 20

<210> SEQ ID NO 47
<211> LENGTH: 20
<212> TYPE: DNA
<213> ORGANISM: Artificial sequence
<220> FEATURE:
<223> OTHER INFORMATION: Primer

<400> SEQUENCE: 47
tcttcttcat gacctcgccg                                                 20

<210> SEQ ID NO 48
<211> LENGTH: 20
<212> TYPE: DNA
<213> ORGANISM: Artificial sequence
<220> FEATURE:
<223> OTHER INFORMATION: Primer

<400> SEQUENCE: 48
ggaccagcta accaacgaca                                                 20

<210> SEQ ID NO 49
<211> LENGTH: 20
<212> TYPE: DNA
<213> ORGANISM: Artificial sequence
<220> FEATURE:
<223> OTHER INFORMATION: Primer

<400> SEQUENCE: 49
aaggtcaaga cgtgccagag                                                 20
```

PHARMACEUTICAL COMPOSITION FOR TREATMENT OF DISEASES ASSOCIATED WITH UPREGULATED PERIOSTIN EXPRESSION OR PERIOSTIN SPLICE VARIANT SWITCHING

CROSS REFERENCE TO RELATED APPLICATIONS

This application is a U.S. National Phase Application of PCT International Application Number PCT/JP2019/002015, filed on Jan. 23, 2019, designating the United States of America and published in the Japanese language, which is an International Application of and claims the benefit of priority to Japanese Patent Application No. 2018-010354, filed on Jan. 25, 2018. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 37 U.S.C. § 1.52 (e). The name of the ASCII text file for the Sequence Listing is SeqList-IWAT007-010APC.txt, the date of creation of the ASCII text file is Jan. 17, 2019, and the size of the ASCII text file is 94 KB.

TECHNICAL FIELD

The present invention relates to a pharmaceutical composition for the treatment of a disease associated with upregulated periostin expression or periostin splice variant switching.

BACKGROUND ART

Periostin is an extracellular matrix protein with a molecular weight of about 90,000. Periostin was originally identified as a protein which is expressed in a mouse osteoblast cell line and is involved in osteogenesis and odontogenesis. The structure of periostin, as shown in FIG. 1, has four FAS1 domains in the central region, an N-terminal secretion signal sequence, and a cysteine-rich EMI domain in between. The C-terminal region (exons 15 to 23) has alternative splicing sites resulting in generation of different splice variants, and there are mainly 4 types of splice variants (see FIG. 1).

Periostin is known to form crosslinks with various kinds of extracellular matrices, which may lead to the formation of fibroblastic foci (Non Patent Literature 1). Periostin is also known as a matricellular protein that binds to integrins and mediates the interaction between cells and matrices (Non Patent Literature 2). Other studies have reported upregulated periostin expression and periostin splice variant switching in various kinds of diseases, specifically, heart failure (Non Patent Literature 3 to 5), breast cancer (Non Patent Literature 6), cholangiocarcinoma (Non Patent Literature 7), pancreatic cancer, malignant melanoma, glioblastoma, bronchial asthma (Non Patent Literature 8 and 9), diabetic retinopathy (Non Patent Literature 10 to 12), knee osteoarthritis (Non Patent Literature 13), atopic dermatitis (Non Patent Literature 14 and 15), idiopathic interstitial pneumonia, age-related macular degeneration, treatment-resistant breast cancer cells with epithelial-to-mesenchymal transition (Non Patent Literature 16), etc.

Periostin is expressed also in various normal tissues and involved in odontogenesis, osteogenesis, cardiac valve formation, etc. Accordingly, periostin knockout mice manifest dental hypoplasia, growth retardation, and cardiac valve malformation (Non Patent Literature 17). Moreover, periostin knockout mice have a higher risk of cardiac rupture after myocardial infarction as compared with wild-type mice (Non Patent Literature 18).

The present inventors have produced neutralizing antibodies capable of targeting a periostin splice variant having a different C-terminal region, that is, a neutralizing antibody against a peptide encoded by exon 17 and a neutralizing antibody against a peptide encoded by exon 21, and revealed that these antibodies are effective for the treatment of heart failure, cancer, inflammatory disease, etc. (Patent Literature 1 to 3).

CITATION LIST

Patent Literature

Patent Literature 1: WO 2007/077934
Patent Literature 2: WO 2009/001940
Patent Literature 3: WO 2014/136910

Non Patent Literature

Non Patent Literature 1:
Kii I, and Ito H, Cell Mol Life Sci. 2017 December; 74(23):4269-4277.
Non Patent Literature 2:
Baril P, et al., Oncogene. 2007 Mar. 29; 26(14):2082-94.
Non Patent Literature 3:
Norum H M, et al., J Cardiovasc Transl Res. 2017 August; 10(4):401-410.
Non Patent Literature 4:
Katsuragi N, et al., Circulation. 2004 Sep. 28; 110(13):1806-13.
Non Patent Literature 5:
Taniyama Y, et al., Hypertension. 2016 February; 67(2):356-61.
Non Patent Literature 6:
Kyutoku M, et al., Int J Mol Med. 2011 August; 28(2):181-6.
Non Patent Literature 7:
Fujimoto K, et al., Oncol Rep. 2011 May; 25(5):1211-6.
Non Patent Literature 8:
Woodruff P G, et al., Proc Natl Acad Sci USA. 2007 Oct. 2; 104(40):15858-63.
Non Patent Literature 9:
Jia G, et al., J Allergy Clin Immunol. 2012 September; 130(3):647-654.e10.
Non Patent Literature 10:
Takada M, et al., Biochem Biophys Res Commun. 2010 Aug. 20; 399(2):221-6.
Non Patent Literature 11:
Yoshida S, et al., Ophthalmol Vis Sci. 2011 Jul. 29; 52(8): 5670-8.
Non Patent Literature 12:
Nakama T, et al., Exp Eye Res. 2016 December; 153:133-140.
Non Patent Literature 13:
Chijimatsu R, et al., BMC Musculoskelet Disord. 2015 Aug. 21; 16:215.
Non Patent Literature 14:
Masuoka M, et al., J Clin Invest. 2012 July; 122(7):2590-600.
Non Patent Literature 15:
Shiraishi H, et al., Allergol Int. 2012 December; 61(4):563-72.

Non Patent Literature 16:
Morra L, and Moch H., Virchows Arch. 2011 November; 459(5):465-5. Review.
Non Patent Literature 17:
Rios H, et al., Mol Cell Biol. 2005 December; 25(24):11131-44.
Non Patent Literature 18:
Shimazaki M, et al., J Exp Med. 2008 Feb. 18; 205(2):295-303.

SUMMARY OF INVENTION

Technical Problem

An object of the present invention is to provide a pharmaceutical composition for the treatment of a disease associated with upregulated periostin expression or periostin splice variant switching, which pharmaceutical composition prevents complete inhibition of the functions of periostin.

Solution to Problem

The present invention includes the following to achieve the above-mentioned object.
[1] A pharmaceutical composition for treatment of a disease associated with upregulated periostin expression or periostin splice variant switching, the pharmaceutical composition comprising, as an active ingredient, a nucleic acid capable of inducing skipping of exon 17 in periostin gene transcription and/or a nucleic acid capable of inducing skipping of exon 21 in periostin gene transcription.
[2] The pharmaceutical composition according to the above [1], wherein the nucleic acids are antisense nucleic acids.
[3] The pharmaceutical composition according to the above [2], wherein the antisense nucleic acid capable of inducing skipping of exon 17 is one or more kinds of nucleic acids of 14 to 50 bases that target the region of positions 24143 to 24323 of the nucleotide sequence represented by SEQ ID NO: 1.
[4] The pharmaceutical composition according to the above [3], wherein the antisense nucleic acid capable of inducing skipping of exon 17 targets at least one of the regions of positions 24191 to 24193, positions 24215 to 24220, positions 24247 to 24254, positions 24249 to 24258, positions 24252 to 24255, and positions 24273 to 24275 of the nucleotide sequence represented by SEQ ID NO: 1.
[5] The pharmaceutical composition according to the above [2], wherein the antisense nucleic acid capable of inducing skipping of exon 21 is one or more kinds of nucleic acids of 14 to 50 bases that target the region of positions 29412 to 29595 of the nucleotide sequence represented by SEQ ID NO: 1.
[6] The pharmaceutical composition according to the above [5], wherein the antisense nucleic acid capable of inducing skipping of exon 21 targets at least one of the regions of positions 29460 to 29462, positions 29468 to 29474, positions 29472 to 29479, positions 29509 to 29515, positions 29525 to 29531, positions 29530 to 29536, positions 29531 to 29538, positions 29534 to 29539, positions 29534 to 29541, positions 29536 to 29542, and positions 29545 to 29547 of the nucleotide sequence represented by SEQ ID NO: 1.
[7] The pharmaceutical composition according to any one of the above [2] to [6], wherein the pharmaceutical composition comprises an adeno-associated viral vector designed to express the antisense nucleic acid capable of inducing skipping of exon 17 and/or the antisense nucleic acid capable of inducing skipping of exon 21.
[8] The pharmaceutical composition according to any one of the above [1] to [7], wherein the disease associated with upregulated periostin expression or periostin splice variant switching is a disease associated with upregulation of a splice variant containing periostin gene exon 17 and/or exon 21.
[9] The pharmaceutical composition according to the above [8], wherein the disease associated with upregulated periostin expression or periostin splice variant switching is at least one kind selected from the group consisting of heart failure, renal failure, breast cancer, cholangiocarcinoma, pancreatic cancer, malignant melanoma, glioblastoma, bronchial asthma, diabetic retinopathy, knee osteoarthritis, atopic dermatitis, idiopathic interstitial pneumonia, and age-related macular degeneration.
[10] The pharmaceutical composition according to the above [8], wherein the pharmaceutical composition is for use in treatment of heart failure, treatment of renal failure, treatment of diabetic retinopathy, prevention of breast cancer metastasis, or prevention of malignant melanoma metastasis.
[11] The pharmaceutical composition according to any one of the above [1] to [10], wherein the pharmaceutical composition is used in combination with a therapeutic agent for the disease associated with upregulated periostin expression or periostin splice variant switching.

Advantageous Effects of Invention

The present invention provides a pharmaceutical composition for the treatment of a disease associated with upregulated periostin expression or periostin splice variant switching, which pharmaceutical composition prevents complete inhibition of the functions of periostin. Since the pharmaceutical composition of the present invention prevents complete inhibition of the functions of periostin, the pharmaceutical composition does not cause adverse effects such as bone or tooth growth inhibition and can treat a disease associated with upregulated periostin expression or periostin splice variant switching.

BRIEF DESCRIPTION OF DRAWINGS

FIG. 7A show the results of immunofluorescence staining with the anti-exon 17 antibody and an anti-αSMA antibody, and FIG. 7B shows the results of immunostaining with the anti-exon 17 antibody (day 21).

FIG. 17A shows the results of non-treatment with paclitaxel, and FIG. 17B shows the results of treatment with paclitaxel.

FIG. 18A shows the results of non-treatment with paclitaxel, and FIG. 18B shows the results of treatment with paclitaxel.

DESCRIPTION OF EMBODIMENTS

Figure 1:
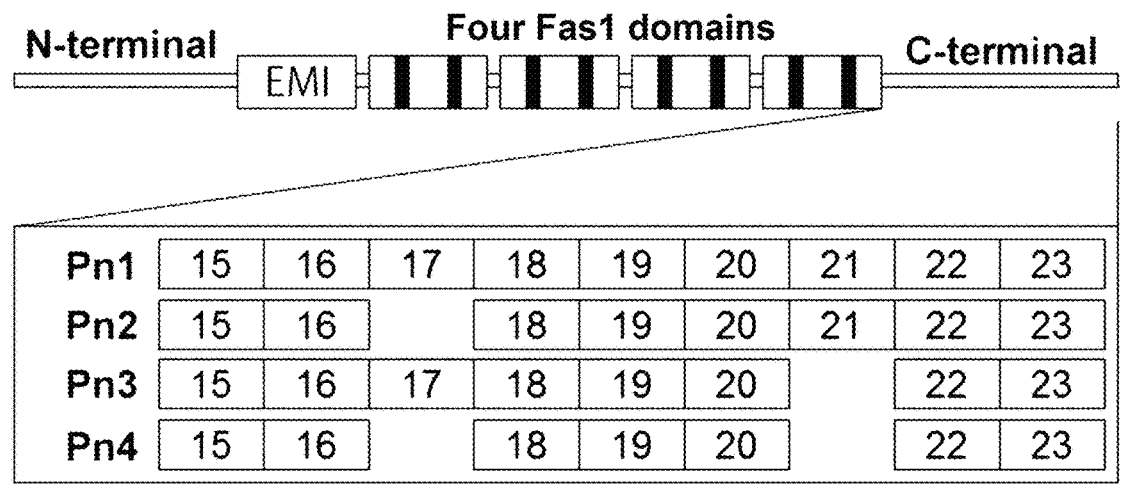
FIG. 1 is a schematic view showing the structure of periostin protein and 4 splice variants having different C-terminal regions.

The pharmaceutical composition of the present invention is a pharmaceutical composition for the treatment of a disease associated with upregulated periostin expression or periostin splice variant switching, which pharmaceutical composition comprises, as an active ingredient, a nucleic acid capable of inducing skipping of exon 17 in periostin gene transcription and/or a nucleic acid capable of inducing skipping of exon 21 in periostin gene transcription. The periostin gene is, for example, a human periostin gene represented by SEQ ID NO: 1, a mouse periostin gene represented by SEQ ID NO: 2, or the like.

"Skipping of exon 17 in periostin gene transcription" means that, in the splicing process, in which introns of a primary transcript, so-called pre mRNA, are spliced out to form a mature mRNA, not only introns but also exon 17 are spliced out to form a mature mRNA lacking exon 17. Similarly, "skipping of exon 21 in periostin gene transcription" means that, in the splicing process, in which introns of a primary transcript, pre mRNA, are spliced out to form a mature mRNA, not only introns but also exon 21 are spliced out to form a mature mRNA lacking exon 21. Therefore, the nucleic acid used as the active ingredient of the pharmaceutical composition of the present invention is a nucleic acid capable of hybridizing with a specific sequence of a primary transcript, pre mRNA, of the periostin gene. Such a nucleic acid may be an antisense nucleic acid, siRNA (short interfering RNA), shRNA (short hairpin RNA), or the like.

In general, the sequence targeted by a nucleic acid capable of inducing skipping of a specific exon is preferably a sequence containing a splicing acceptor site, a sequence containing a splicing donor site, a sequence containing an intronic splicing enhancer sequence, or a sequence containing an exonic splicing enhancer sequence (Nucleic Acid Ther. 2014, February; 24(1):69-86, Biochem Biophys Res Commun. 2007, Jun. 29; 358(2):521-527). Therefore, the sequence targeted by the nucleic acid used as the active ingredient of the pharmaceutical composition of the present invention can be determined using the combination of such known art and the nucleotide sequence information of the periostin gene, and based on the nucleotide sequence of the targeted region, the nucleic acid used as the active ingredient of the pharmaceutical composition can be designed.

The nucleic acid capable of inducing skipping of exon 17 preferably targets the region of positions 24143 to 24323 of the nucleotide sequence represented by SEQ ID NO: 1. This sequence contains exon 17 (positions 24193 to 24273) and the adjacent upstream and downstream introns of 50 bases each. This sequence contains a splicing acceptor site upstream of exon 17, a splicing donor site downstream of exon 17, and multiple exonic splicing enhancer sequences.

The sequence containing the splicing acceptor site upstream of exon 17 of a human periostin gene corresponds to, for example, positions 24191 to 24193 of the nucleotide sequence represented by SEQ ID NO: 1. The sequence containing the splicing donor site downstream of exon 17 of a human periostin gene corresponds to, for example, positions 24273 to 24275 of the nucleotide sequence represented by SEQ ID NO: 1. The exonic splicing enhancer sequences in exon 17 of a human periostin gene correspond to, for example, positions 24215 to 24220, positions 24247 to 24254, positions 24249 to 24258, and positions 24252 to 24255 of the nucleotide sequence represented by SEQ ID NO: 1. The sequence targeted by the nucleic acid capable of inducing skipping of exon 17 is preferably at least one of these sequences. The exonic splicing enhancer sequences can be predicted using ESEfinder 3.0 (rulai.cshl.edu/cgi-bin/tools/ESE3/esefinder.cgi), for example.

The nucleic acid capable of inducing skipping of exon 21 preferably targets the region of positions 29412 to 29595 of the nucleotide sequence represented by SEQ ID NO: 1. This sequence contains exon 21 (positions 29462 to 29545) and the adjacent upstream and downstream introns of 50 bases each. This sequence contains a splicing acceptor site upstream of exon 21, a splicing donor site downstream of exon 21, and multiple exonic splicing enhancer sequences.

The sequence containing the splicing acceptor site upstream of exon 21 of a human periostin gene corresponds to, for example, positions 29460 to 29462 of the nucleotide sequence represented by SEQ ID NO: 1. The sequence containing the splicing donor site downstream of exon 21 of a human periostin gene corresponds to, for example, positions 29545 to 29547 of the nucleotide sequence represented by SEQ ID NO: 1. The exonic splicing enhancer sequences in exon 21 of a human periostin gene correspond to, for example, positions 29468 to 29474, positions 29472 to 29479, positions 29509 to 29515, positions 29525 to 29531, positions 29530 to 29536, positions 29531 to 29538, positions 29534 to 29539, positions 29534 to 29541, and positions 29536 to 29542 of the nucleotide sequence represented by SEQ ID NO: 1. The sequence targeted by the nucleic acid capable of inducing skipping of exon 21 is preferably at least one of these sequences.

In the case where the active ingredient of the pharmaceutical composition of the present invention is an antisense nucleic acid, the length of the antisense nucleic acid is not particularly limited. The length of the antisense nucleic acid is preferably 14 to 50 bases, more preferably 14 to 40 bases, and still more preferably 14 to 30 bases. The antisense nucleic acid used in the present invention contains a sequence complementary to its target sequence (the nucleotide sequence of pre mRNA of the periostin gene), but does not have to be completely complementary to the target sequence. The antisense nucleic acid may contain a mismatch as long as it is capable of hybridizing with the target sequence. The sequence complementary to the target sequence may have a length (number of bases) that is 50% or more, 60% or more, 70% or more, 80% or more, 90% or more, 95% or more, 98% or more, 99% or more, or even 100% of the length of the antisense nucleic acid.

The antisense nucleic acid capable of inducing skipping of exon 17 of a human periostin gene may be, for example, an antisense nucleic acid consisting of the following nucleotide sequence:

(SEQ ID NO: 3)
5'-CCATGTATAACATTGATTTTTACCTTCAGT-3'.

The antisense nucleic acid capable of inducing skipping of exon 21 of a human periostin gene may be, for example, an antisense nucleic acid consisting of the following nucleotide sequence:

(SEQ ID NO: 4)
5'-TTGTTGTCCTTTTACTAACCTCCCT-3'.

The antisense nucleic acid capable of inducing skipping of exon 17 of a mouse periostin gene may be, for example, an antisense nucleic acid consisting of the following nucleotide sequence:

(SEQ ID NO: 5)
5'-TGCTGAAAACATAGAAAGTGGAGCA-3'.

The skipping of exon 17 induced by the antisense nucleic acid can be confirmed, for example, as follows: the antisense nucleic acid is introduced into cultured cells expressing periostin, RNA is extracted from the cells, and the transcript of the periostin gene in the extracted RNA is analyzed by RT-PCR etc. The skipping of exon 21 induced by the antisense nucleic acid can also be confirmed in the same procedure.

The antisense nucleic acid may consist of a DNA strand, an RNA strand, or a DNA-RNA hybrid strand. In addition, the antisense nucleic acid may contain a nucleotide analog. The antisense nucleic acid is preferably modified for the enhancement of nuclease resistance and/or the affinity for the target sequence. In a preferable embodiment, the nucleotide analog contains a modified backbone, for example, a morpholino backbone, a carbamate backbone, a siloxane backbone, a sulfide backbone, a sulfoxide backbone, a sulfone backbone, a formacetyl backbone, a thioformacetyl backbone, a methyleneformacetyl backbone, a riboacetyl backbone, an alkene-containing backbone, a sulfamate backbone, a sulfonate backbone, a sulfonamide backbone, a methyleneimino backbone, a methylenehydrazino backbone, an amide backbone, or the like. A morpholino oligonucleotide has an uncharged backbone in which deoxyribose sugars and phosphodiester linkages in DNA are replaced by 6-membered rings and phosphorodiamidate linkages, respectively. The morpholino oligonucleotide is resistant to enzymatic digestion.

Furthermore, the nucleotide analog preferably has a structure in which one non-bridging oxygen in the phosphodiester linkage is replaced by another atom or group. This modification provides significant resistance to nuclease digestion. In a preferable embodiment, the nucleotide analog contains phosphorothioate, chiral phosphorothioate, phosphorodithioate, phosphotriester, aminoalkylphosphotriester, H-phosphonate, ethylphosphonate and other alkylphosphonates (e.g., 3'-alkylenephosphonate, 5'-alkylenephosphonate, and chiral phosphonate), phosphinate, phosphoramidates (e.g., 3'-aminophosphoramidate and aminoalkylphosphoramidate), thionophosphoramidate, thionoalkylphosphonate, thionoalkylphosphotriester, selenophosphate, or boranophosphate.

Furthermore, the nucleotide analog preferably contains one or more sugar moieties that are substituted at the 2', 3', and/or 5' positions with one or two substituents including —OH; —F; substituted or unsubstituted, straight- or branched-chain lower (C1 to C10) alkyl, alkenyl, alkynyl, alkaryl, allyl, or aralkyl that may be interrupted by one or more heteroatoms; O—, S—, or N-alkyl; O—, S—, or N-alkenyl; O—, S—, or N-alkynyl; O—, S—, or N-allyl; O-alkyl-O-alkyl, -methoxy, -aminopropoxy; -methoxyethoxy; -dimethylaminooxyethoxy; and -dimethylaminoethoxyethoxy. The sugar moiety may be pyranose or its derivative, or deoxypyranose or its derivative. Preferably, the sugar moiety may be ribose or its derivative, or deoxyribose or its derivative. The sugar moiety in the form of a sugar derivative is preferably a bicyclic sugar moiety in a locked nucleic acid (LNA), in which the 2' carbon atom is connected to the 3' or 4' carbon atom in the sugar ring. The LNA preferably contains a 2'-O, 4'-C— ethylene-bridged nucleic acid (Morita et al., 2001, Nucleic Acid Res Supplement No. 1:241-242). These substitutions provide a nucleotide analog or an equivalent thereof with RNase H- and nuclease-resistance and enhance the affinity for the target RNA.

Moreover, the antisense nucleic acid may have a modification at the 5' and/or 3' end. The modification includes triethylene glycol (TEG) modification, hexaethylene glycol (HEG) modification, and dodecaethylene glycol (DODEG) modification.

The antisense nucleic acid can be prepared by a known nucleic acid synthesis method. The known method may be the method described in, for example, WO 2009/064471 or WO 2013/100190. siRNA and shRNA can also be prepared by a known nucleic acid synthesis method.

The disease associated with upregulated periostin expression refers to a disease characterized in that the periostin expression level after the onset of the disease is higher than that under healthy conditions. The periostin expression level can be confirmed by measuring the periostin protein concentration in blood or the periostin mRNA or protein level in cells of an affected site. The disease associated with periostin splice variant switching refers to a disease characterized in that the expression pattern of periostin splice variants after the onset of the disease is different from that under healthy conditions. The present inventors have confirmed that almost all the organs express Pn4 (a splice variant lacking exons 17 and 21, see FIG. 1) and hardly express other splice variants under healthy conditions (Reference Example 1). That is, the disease associated with periostin splice variant switching is a disease characterized by upregulated expression of Pn1, Pn2, Pn3, etc. (see FIG. 1) after the onset of the disease.

Examples of the disease to be treated with the pharmaceutical composition of the present invention, namely, the disease associated with upregulated periostin expression or periostin splice variant switching include heart failure (post-acute myocardial infarction heart failure, idiopathic cardiomyopathy, etc.), renal failure (acute renal failure, chronic renal failure, etc.), cancers (breast cancer, cholangiocarcinoma, pancreatic cancer, malignant melanoma, glioblastoma, etc.), bronchial asthma, diabetic retinopathy, knee osteoarthritis, atopic dermatitis, idiopathic interstitial pneumonia, and age-related macular degeneration. The pharmaceutical composition of the present invention is particularly effective for treatment of heart failure, treatment of renal failure, treatment of diabetic retinopathy, prevention of breast cancer metastasis, or prevention of malignant melanoma metastasis. Moreover, the pharmaceutical composition of the present invention can be used in combination with another therapeutic agent for the disease of interest, namely, the disease associated with upregulated periostin expression or periostin splice variant switching, and thereby can enhance the effect of the therapeutic agent used in combination therewith. For example, the administration of the pharmaceutical composition of the present invention to a patient currently undergoing anticancer drug treatment can enhance the therapeutic effect of the anticancer agent.

The pharmaceutical composition of the present invention may contain one kind of antisense nucleic acid as an active ingredient, or two or more kinds of antisense nucleic acids as active ingredients. The combination of two or more kinds of antisense nucleic acids as active ingredients is not particularly limited and is preferably a combination of two or more kinds of antisense nucleic acids that produces an enhanced effect as compared with their use alone.

The pharmaceutical composition of the present invention can be prepared in a dosage form by appropriately mixing an antisense nucleic acid capable of inducing skipping of exon 17 in periostin gene transcription and/or an antisense nucleic acid capable of inducing skipping of exon 21 in periostin gene transcription, each of which is as an active ingredient, with a pharmaceutically acceptable carrier or additive. Specific examples of the dosage form include oral preparations such as tablets, coated tablets, pills, powders, granules, capsules, solutions, suspensions, and emulsions; and parenteral preparations such as injections, infusions, suppositories, ointments, and patches. Preferred are parenteral preparations. Injections may be lyophilized preparations. The amount of the carrier or the additive to be used is determined as appropriate based on the range of amount conventionally used in the pharmaceutical field. The carrier or the additive that can be used is not particularly limited, and examples include various carriers such as water, physiological saline, other aqueous solvents, and aqueous or oily bases; and various additives such as fillers, binders, pH adjusters, disintegrants, absorption enhancers, lubricants, colorants, corrigents, and fragrances.

Examples of the additive that can be contained in tablets, capsules, and the like include binders such as gelatin, cornstarch, tragacanth, and gum arabic; fillers such as crystalline cellulose; bulking agents such as cornstarch, gelatin, and alginic acid; lubricants such as magnesium stearate; sweeteners such as sucrose, lactose, and saccharin; and flavors such as peppermint, Gaultheria adenothrix oil, and cherry. In the case where the unit dosage form is a capsule, a liquid carrier such as fats and oils can be further contained in addition to the above-mentioned ingredients. A sterile composition for injection can be prepared according to the usual pharmaceutical formulation practice, for example, by dissolving or suspending an active ingredient in a solvent such as water for injection and a natural vegetable oil. As an aqueous liquid for injection, for example, physiological saline, an isotonic solution containing glucose and an auxiliary substance (e.g., D-sorbitol, D-mannitol, sucrose, sodium chloride, etc.), or the like can be used, optionally together with a suitable solubilizer such as alcohols (e.g., ethanol etc.), polyalcohols (e.g., propylene glycol, polyethylene glycol, etc.), and nonionic surfactants (e.g., polysorbate 80, HCO-50, etc.). As an oily liquid, for example, sesame oil, soybean oil, or the like can be used, optionally together with a solubilizer such as benzyl benzoate and benzyl alcohol. Further, a buffering agent (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, and/or the like may also be added. The sterile composition for injection may be a lyophilized preparation.

The pharmaceutical composition of the present invention can be administered to a human having developed the disease associated with upregulated periostin expression or periostin splice variant switching. The administration route is not particularly limited and is preferably parenteral administration. The parenteral administration may be systemic administration such as intravenous administration, or local administration such as intramuscular administration, transdermal administration, or transmucosal administration. The antisense nucleic acid contained as the active ingredient in the pharmaceutical composition of the present invention can be administered in the form of a non-viral or viral vector. Alternatively, the administration can be performed by, for example, a method using liposomes to introduce an antisense nucleic acid (the liposome method, the HVJ-liposome method, the cationic liposome method, the lipofection method, the lipofectamine method, etc.), microinjection, a method using a gene gun to introduce an antisense nucleic acid and a carrier (metal particles), or a method using a combination of sonophoresis and other techniques.

The pharmaceutical composition of the present invention may be administered in the form of an adeno-associated viral vector. Adeno-associated viruses are highly safe, unlikely to cause immune response against transfected host cells, capable of inducing long-term gene expression in non-proliferating cells. For these reasons, adeno-associated viruses can preferably be used as viral vectors for gene therapy. In addition, adeno-associated viral vectors have been practically used in clinical cases of hemophilia, muscular dystrophy, age-related macular degeneration, etc. and proven safe in humans. Therefore, an adeno-associated viral vector is one of the preferable forms for the administration of the pharmaceutical composition of the present invention.

The dosage of the pharmaceutical composition of the present invention varies with the disease to be treated, the type of the antisense nucleic acid contained in the pharmaceutical composition, the dosage form, the administration route, and the age and body weight of the patient. In the case where the pharmaceutical composition of the present invention is administered in the form of an injection, the daily dosage can be about 0.01 mg to about 60 g, preferably about 0.1 mg to about 24 g, and more preferably about 0.1 mg to about 6 g. The administration can be performed one to several times daily, or at intervals of one day to two weeks.

In the case where the pharmaceutical composition of the present invention is used in combination with another or other therapeutic agents for the disease of interest, they may be simultaneously administered to a subject or separately administered to a subject at some interval. The term "used in combination" herein means that the period of treatment with one drug overlaps with the period(s) of treatment with another or other drugs, and the two or more drugs are not necessarily required to be simultaneously administered. The mode of combination of the drugs is not particularly limited, and the pharmaceutical composition of the present invention may be combined with another or other therapeutic agents for the disease of interest in any manner. The dosage(s) of another or other therapeutic agents for the disease of interest can be determined based on its or their clinical dosages, and the appropriate dosage(s) can be selected depending on the subject, the age and body weight of the subject, the symptoms, the administration time, the dosage form, the administration method, the combination of the therapeutic agents, etc.

The pharmaceutical composition of the present invention prevents complete inhibition of the functions of periostin and selectively inhibits the functions associated with a specific splice variant, more specifically, the functions associated with a region encoded by exon 17 of a periostin gene and/or a region encoded by exon 21 of a periostin gene. For this reason, the pharmaceutical composition of the present invention does not cause adverse effects, such as bone or tooth growth inhibition, and is very useful. More advantageously, the pharmaceutical composition of the present invention is capable of suppressing intracellular expression of a specific periostin unlike conventional antibody drugs.

The present invention further includes the following.
 (i) A method for treating a disease associated with upregulated periostin expression or periostin splice variant switching, the method comprising administering an effective amount of an antisense nucleic acid capable of inducing skipping of exon 17 in periostin gene transcription and/or an effective amount of an antisense nucleic acid capable of inducing skipping of exon 21 in periostin gene transcription to a patient with the disease.
 (ii) An antisense nucleic acid for use in treatment of a disease associated with upregulated periostin expression or periostin splice variant switching, the antisense nucleic acid being an antisense nucleic acid capable of inducing skipping of exon 17 in periostin gene transcription and/or an antisense nucleic acid capable of inducing skipping of exon 21 in periostin gene transcription.
 (iii) Use of an antisense nucleic acid for production of a therapeutic agent for a disease associated with upregulated periostin expression or periostin splice variant switching, the antisense nucleic acid being an antisense nucleic acid capable of inducing skipping of exon 17 in periostin gene transcription and/or an antisense nucleic acid capable of inducing skipping of exon 21 in periostin gene transcription.

Figure 19:
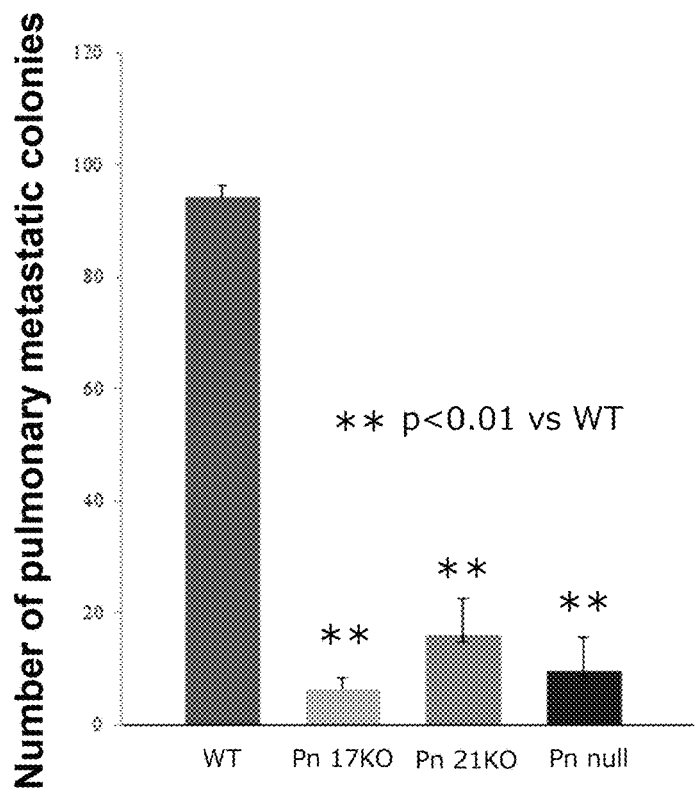
FIG. 19 shows the number of pulmonary metastatic colonies at 3 weeks after transplantation of mouse breast cancer cells (4T1) into the left paw in wild-type mice, periostin exon 17 knockout mice (Pn 17KO mice), periostin exon 21 knockout mice (Pn 21KO mice), and complete periostin knockout mice (Pn null mice).

The present inventors have confirmed tumor suppression (prevention of pulmonary metastasis of breast cancer cells) in complete periostin knockout mice generated using ES cells transfected with a targeting vector against exons 2 and 3 (see Reference Example 2), as well as in exon 17 knockout mice and in exon 21 knockout mice, as shown in Reference Example 5 (FIG. 19). These results support the hypothesis that a nucleic acid capable of inducing skipping of exon 2 in periostin gene transcription and/or a nucleic acid capable of inducing skipping of exon 3 in periostin gene transcription has a potential as an active ingredient of the pharmaceutical product of the present invention.

EXAMPLES

Hereinafter, the present invention will be described in detail by examples, but the present invention is not limited thereto.

Reference Example 1: Expression Analysis of Periostin Splice Variants in Various Organs of Normal Mice Experimental Methods
 The animals used were four 8-week-old male C57BL/6J mice (Oriental BioService, Inc.). The mice were laparotomized under anesthesia, and the organs were perfused via the heart with physiological saline. The perfused organs (heart, aorta, adrenal glands, lung, spleen, stomach, kidneys, skin, brain, liver, colon, testes) were excised. Each organ was homogenized by the usual method, and total RNA was extracted using RNeasy Plus Mini Kit (Qiagen). The total RNA was treated with DNase and subjected to reverse transcription using High-Capacity cDNA Reverse Transcriptase Kit (Applied Biosystems). The resulting cDNA was subjected to quantitative PCR. The copy number of the transcript in each sample was determined using plasmids each containing a known copy number of a different splice variant (Pn1, Pn2, Pn3, and Pn4, see FIG. 1). The quantitative PCR was performed using ViiA-7 Real-Time PCR System (Applied Biosystems, Foster City, CA, USA). Statistical analysis was performed by analysis of variance and Tukey-Kramer adjustment using the JMP statistical software package.

Results

Figure 2:
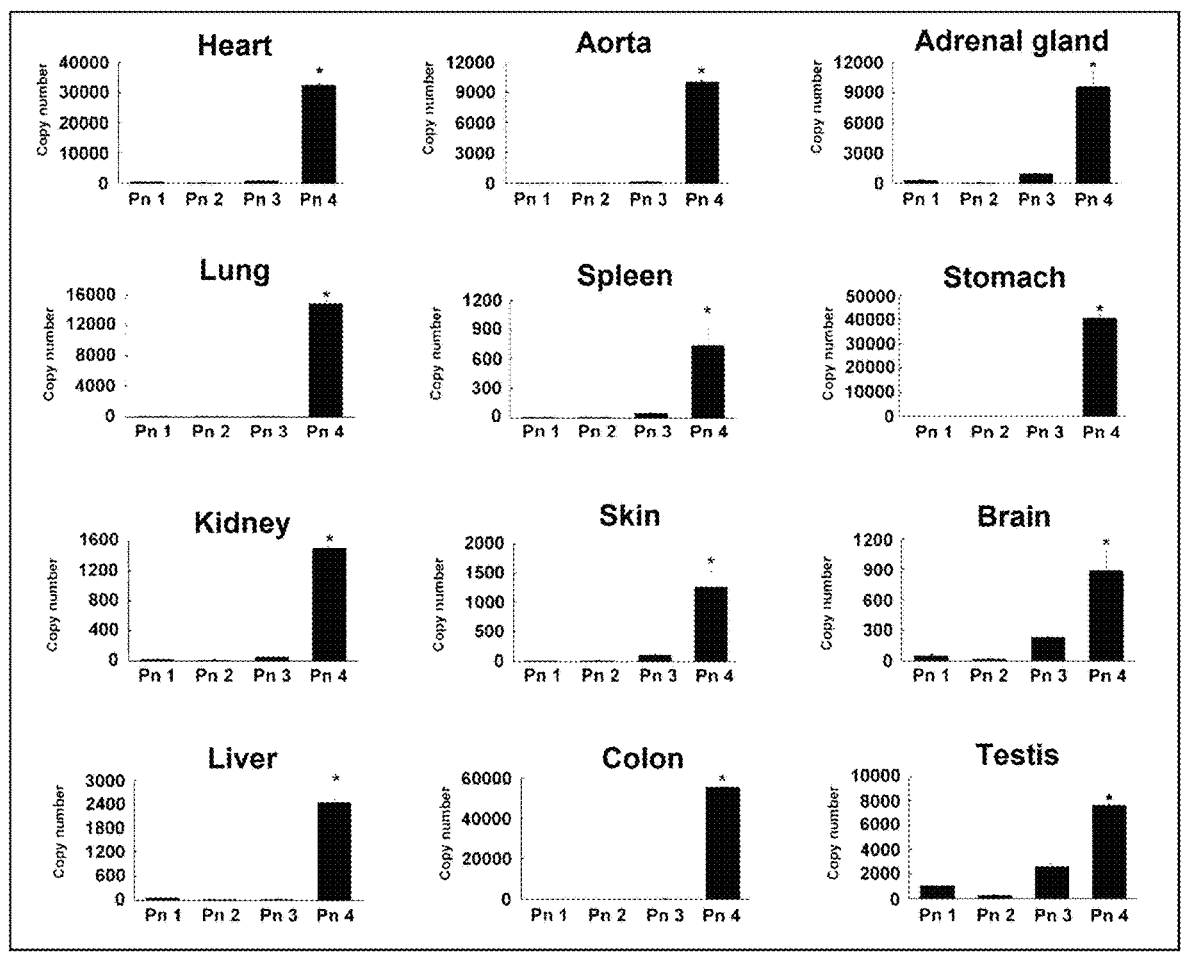
FIG. 2 shows the results of expression analysis of periostin splice variants in various organs of normal mice.

The results are shown in FIG. 2. In normal mice, the copy number of Pn4 (a splice variant lacking exons 17 and 21) in each of the examined organs was about 100 to 10000 times higher than that of any of the other splice variants (Pn1, Pn2, Pn3).

Reference Example 2: Characteristics of Periostin Knockout Mice

Experimental Methods
(1) Generation of Knockout Mice

Exon 17 knockout mice (Pn 17KO mice), exon 21 knockout mice (Pn 21KO mice), and complete periostin knockout mice (Pn null mice) were generated. The specific procedure was as follows. A targeting vector against exon 2 and exon 3, a targeting vector against exon 17, and a targeting vector against exon 21 were constructed for the generation of the Pn null mice, the Pn 17KO mice, and the Pn21 KO mice, respectively. These targeting vectors were separately introduced into ES cells, and successfully targeted ES cells were used to generate chimeric mice. The chimeric mice were mated with wild-type mice to generate heterozygous mice. The heterozygous mice were interbred to generate knockout mice (homozygous mice). The generation of the knockout mice was outsourced to RIKEN.
(2) Tooth Observation The teeth of the wild-type (C57BL/6J, male, n=5), Pn 17KO (male, n=10), Pn 21KO (male, n=10), and Pn null (male, n=10) mice were observed at the age of 8 weeks, and a representative image for each group was taken.
(3) Measurement of Body Weight and Tail Length The body weights and tail lengths of the wild-type (C57BL/6J, male, n=5), Pn 17KO (male, n=10), Pn 21KO (male, n=10), and Pn null (male, n=10) mice were measured every two weeks at the ages of 6 to 16 weeks. Statistical analysis was performed by analysis of variance and Tukey-Kramer adjustment using the JMP statistical software package.

Results

Figure 3:
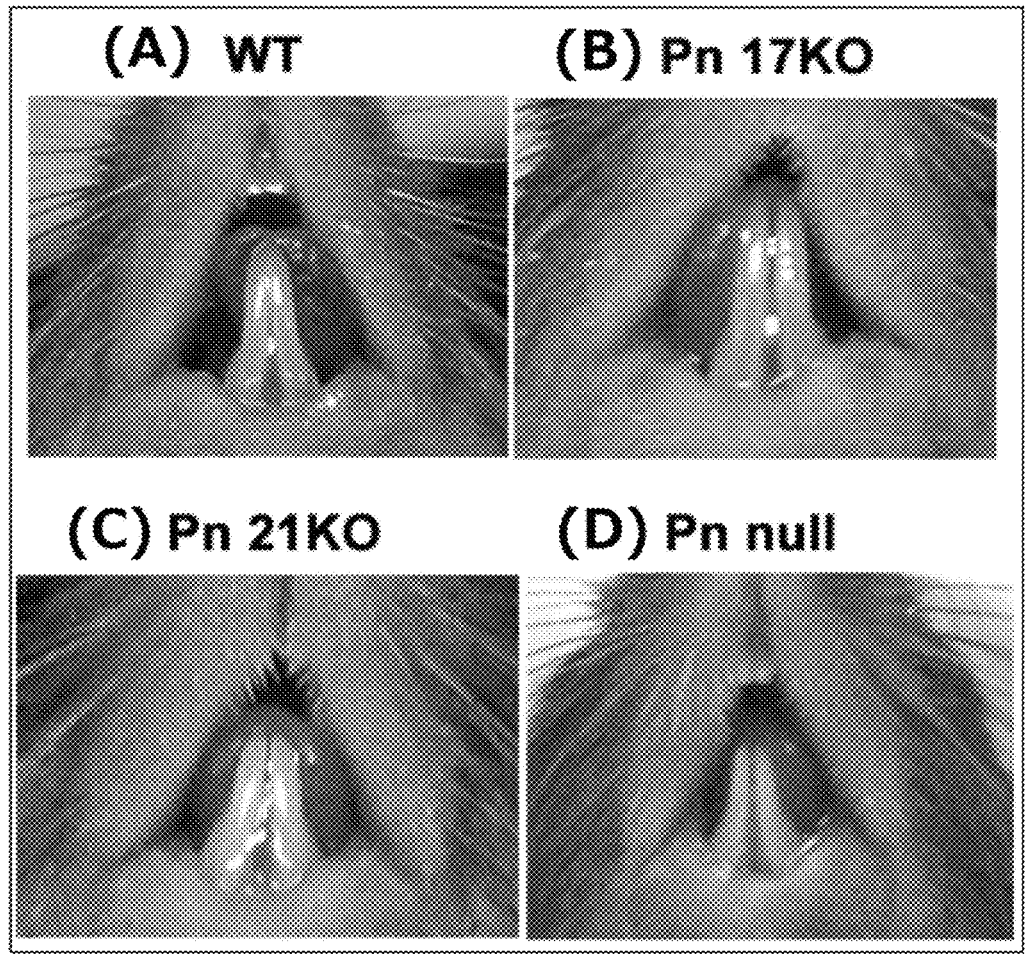
FIG. 3 shows the results of tooth observation in (A) wild-type mice, (B) periostin exon 17 knockout mice (Pn 17KO mice), (C) periostin exon 21 knockout mice (Pn 21KO mice), and (D) complete periostin knockout mice (Pn null mice).

The results of the tooth observation in each group (representative image for each group) are shown in FIG. 3. The Pn null mice had smaller teeth than those of the wild-type (WT), Pn 17KO, and Pn 21KO mice, indicating that dental hypoplasia had occurred in the Pn null mice.

Figure 4:
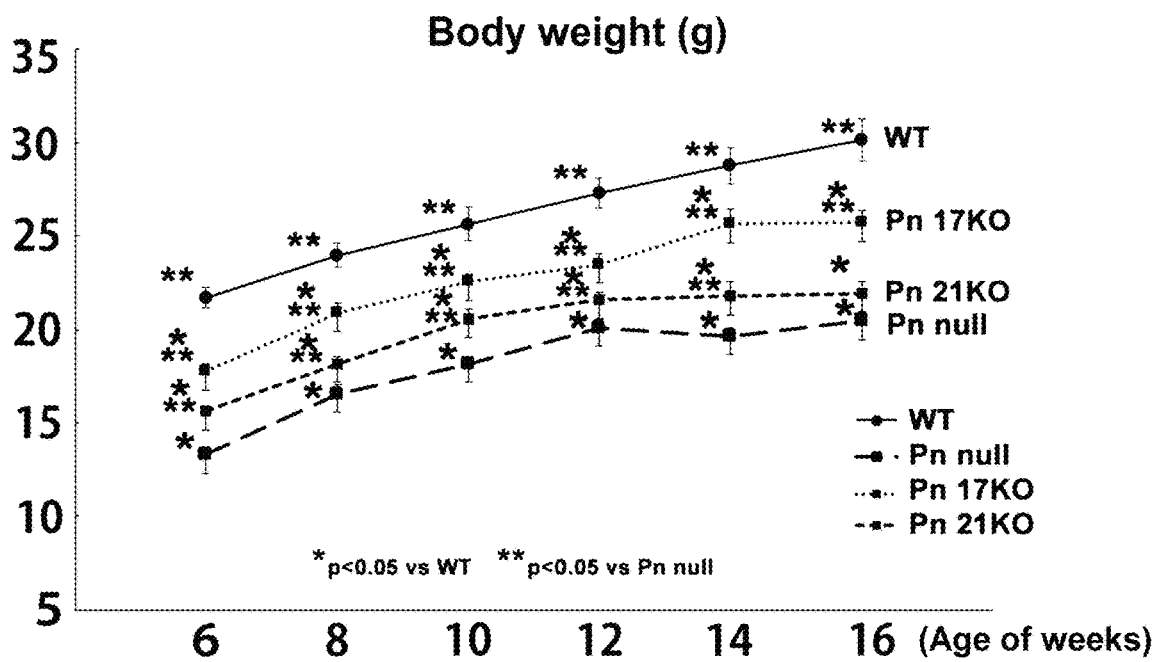
FIG. 4 shows the results of body weight measurement in wild-type mice, periostin exon 17 knockout mice (Pn 17KO mice), periostin exon 21 knockout mice (Pn 21KO mice), and complete periostin knockout mice (Pn null mice).
Figure 5:
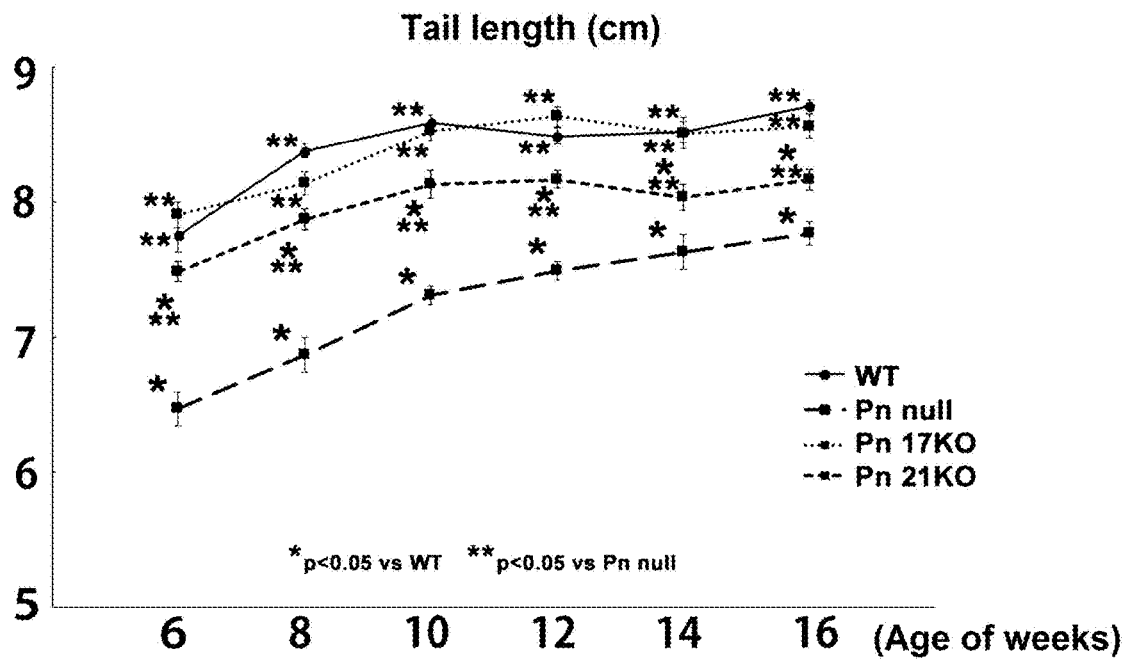
FIG. 5 shows the results of tail length measurement in wild-type mice, periostin exon 17 knockout mice (Pn 17KO mice), periostin exon 21 knockout mice (Pn 21KO mice), and complete periostin knockout mice (Pn null mice).

The results of the body weight measurement are shown in FIG. 4, and the results of the tail length measurement are shown in FIG. 5. The Pn null mice had a lower body weight and a shorter tail length as compared with the WT, Pn17KO, and Pn 21KO mice.

Reference Example 3: Unilateral Ureteral Obstruction Model Induced in Wild-Type Mice Experimental Methods The animals used were wild-type mice (C57BL/6J, male, 8 weeks old). The mice were laparotomized under anesthesia, and the ureter on one side was ligated with a 4-0 silk suture to induce a unilateral ureteral obstruction (UUO) model. The UUO model is known to develop acute renal failure and subsequent fibrosis leading to chronic renal failure (Kidney Int. 2009, June; 75(11):1145-52). The unilateral obstructed kidneys were excised from 6 mice per time-point before the UUO operation (day 0) and on day 3, 7, 14, 21, 28, 42 and 49 after the UUO operation. Total RNA was extracted from each kidney and subjected to cDNA synthesis as described in Reference Example 1. The resulting cDNA was subjected to quantitative PCR to measure the expression level of each periostin splice variant (Pn1l, Pn2, Pn3, and Pn4, see FIG. 1) using a specific primer set for each splice variant (shown below). Statistical analysis was performed by analysis of variance and Tukey-Kramer adjustment using the JMP statistical software package.

```
                                        (SEQ ID NO: 7)
Mouse Pn1-F: 5'-ATAACCAAAGTCGTGGAACC-3'

(SEQ ID NO: 8)
Mouse Pn1-R: 5'-TGTCTCCCTGAAGCAGTCTT-3'

(SEQ ID NO: 9)
Mouse Pn2-F: 5'-CCATGACTGTCTATAGACCTG-3'

(SEQ ID NO: 10)
Mouse Pn2-R: 5'-TGTCTCCCTGAAGCAGTCTT-3'

(SEQ ID NO: 11)
Mouse Pn3-F: 5'-ATAACCAAAGTCGTGGAACC-3'

(SEQ ID NO: 12)
Mouse Pn3-R: 5'-TTTGCAGGTGTGTCTTTTTG-3'

(SEQ ID NO: 13)
Mouse Pn4-F: 5'-CCCCATGACTGTCTATAGACC-3'

(SEQ ID NO: 14)
Mouse Pn4-R: 5'-TTCTTTGCAGGTGTGTCTTTT-3'
```

The kidneys excised on day 0, 21, and 28 were fixed with formalin, and 4-μm-thick paraffin-embedded sections were prepared from each kidney. The sections were subjected to immunostaining using an anti-exon 17 antibody and an anti-αSMA (smooth muscle actin) antibody according to the usual method. In addition, 10-μm-thick paraffin-embedded sections were prepared from the kidneys excised on day 21 and subjected to in situ hybridization using a riboprobe prepared from the mouse periostin cDNA.

Results

Figure 6:
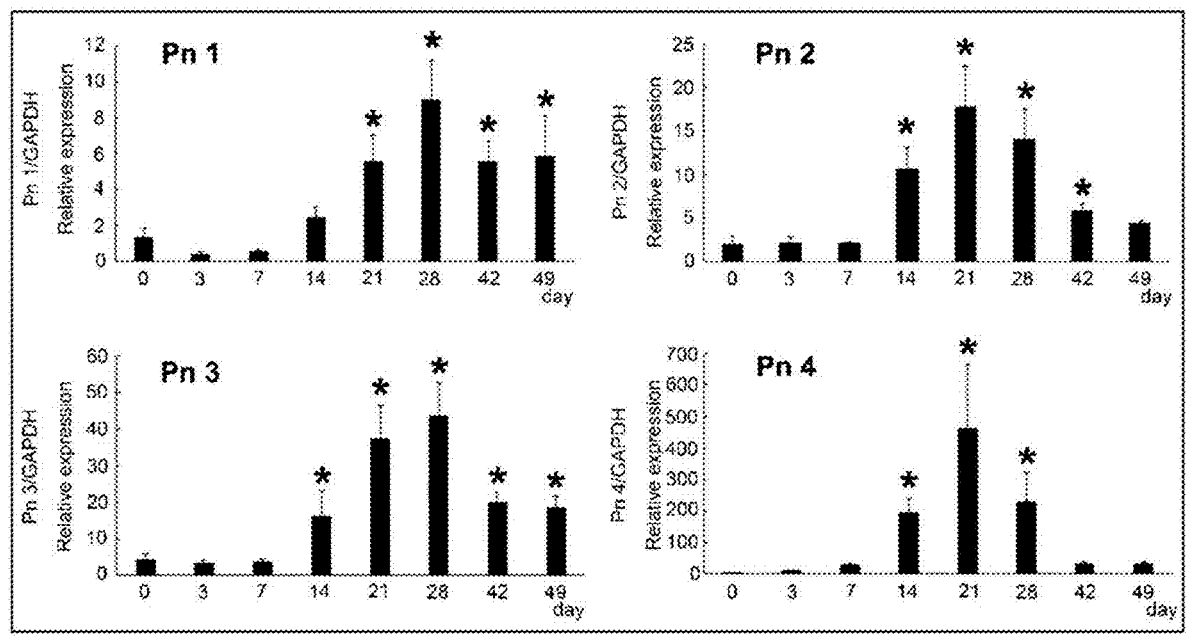
FIG. 6 shows the expression of periostin splice variants measured in the UUO model induced in wild-type mice.

The expression of each periostin splice variant measured in the UUO model induced in wild-type mice is shown in FIG. 6. In each graph, * indicates a significant difference from day 0 (P<0.05). The expression of each splice variant in the unilateral obstructed kidney greatly increased and peaked around on postoperative days 21 to 28. Pn2 mRNA and Pn4 mRNA decreased to almost the baseline levels on days 42 to 49, but Pn1 mRNA and Pn3 mRNA remained at high levels on day 42 or thereafter.

Figure 7:
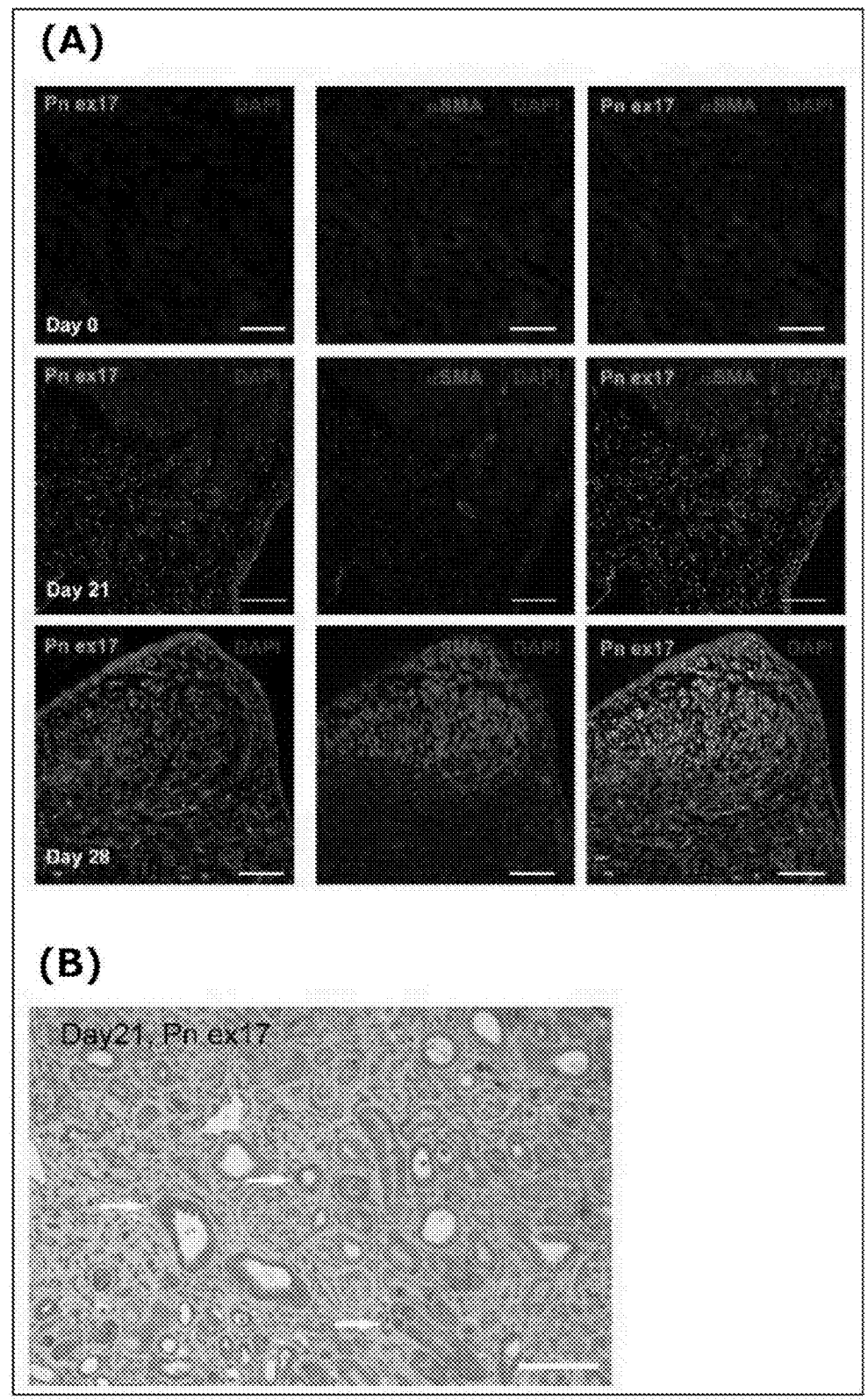
FIG. 7 shows the results of immunostaining with an anti-exon 17 antibody performed on paraffin-embedded sections of the kidneys excised on day 0, 21, and 28 in the UUO model induced in wild-type mice.

The results of the immunostaining are shown in FIG. 7. FIG. 7A show the results of immunofluorescence staining with the anti-exon 17 antibody and the anti-αSMA antibody, and FIG. 7B shows the results of immunostaining with the anti-exon 17 antibody. In each panel, the scale bar marks 100 µm. As shown in FIG. 7A, periostin exon 17 was highly expressed in αSMA-positive cells (myofibroblasts) on postoperative days 21 and 28. As shown in FIG. 7B, the expression of periostin exon 17 was observed in renal tubular epithelial cells on postoperative day 21 (arrows in the panel).

Figure 8:
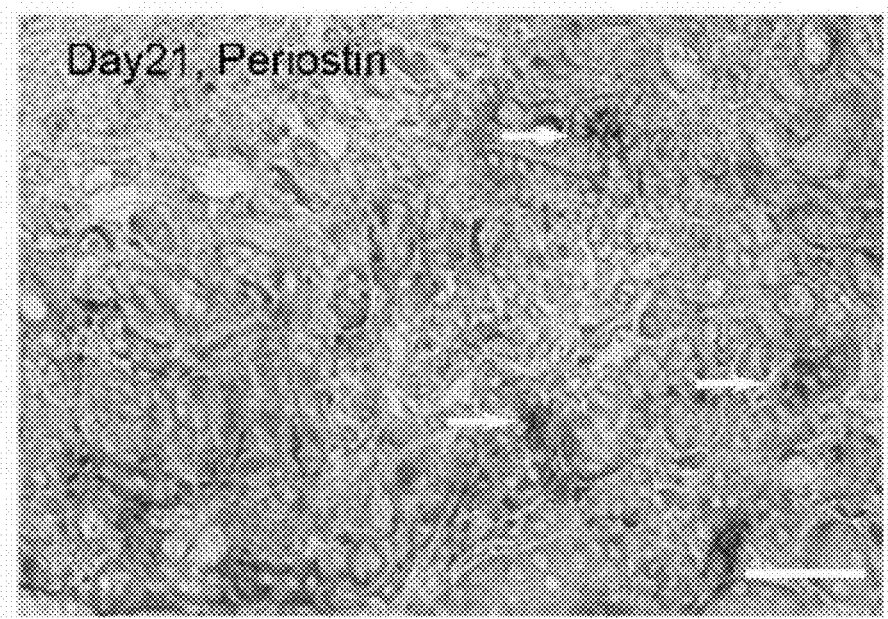
FIG. 8 shows the results of situ hybridization with a riboprobe (prepared from the mouse periostin cDNA) performed on paraffin-embedded sections of the kidney excised on day 21 in the UUO model induced in wild-type mice.

The results of the in situ hybridization are shown in FIG. 8. The scale bar marks 100 µm. As shown in FIG. 8, DIG-positive signals were observed in renal tubular epithelial cells on postoperative day 21 (arrows in the panel). DIG-positive signals were observed also in αSMA-positive cells (myofibroblasts). The above results show that renal tubular epithelial cells and myofibroblasts produce periostin, in particular, periostin variants containing exon 17 (Pn1 and Pn3).

Reference Example 4: UUO Model Induced in Periostin Knockout Mice

Experimental Methods

A UUO model was induced in wild-type C57BL/6J, Pn 17KO, and Pn null mice (male, 8 weeks old) as described in Reference Example 3. The unilateral obstructed kidneys were excised on postoperative day 21, and 4-µm-thick paraffin-embedded sections were prepared from each kidney as described in Reference Example 3. The sections were subjected to Masson's trichrome staining using a Masson's trichrome staining kit (Gene Copoeia) (n=5 per kidney). The Masson's trichrome-positive area (fibrotic area) was measured using IMARIS software (Zurich, Switzerland) and BZ-II analyzer (Keyence, Osaka, Japan).

In addition, total RNA was extracted from kidneys before the UUO operation (day 0) and on postoperative day 21 and subjected to cDNA synthesis (see Reference Example 1). The resulting cDNA was subjected to quantitative PCR using the primers shown below to measure the mRNA expression levels of fibrosis markers (αSMA, type I collagen), inflammatory markers (TNFα, IL-1β), and TGF-β signaling-related molecules (TGF-β1, Snail 1, c-myc, CTGF (connective tissue growth factor)) (n=4 per group and timepoint). Statistical analysis was performed by analysis of variance and Tukey-Kramer adjustment using the JMP statistical software package.

```
                                            (SEQ ID NO: 15)
Mouse Collagen 1-F: 5'-TTCTCCTGGCAAAGACGGAC-3'

(SEQ ID NO: 16)
Mouse Collagen 1-R: 5'-CGGCCACCATCTTGAGACTT-3'

(SEQ ID NO: 17)
Mouse αSMA-F: 5'-CCCTGGAGAAGAGCTACGAAC-3'

(SEQ ID NO: 18)
Mouse αSMA-R: 5'-TACCCCCTGACAGGACGTTG-3'

(SEQ ID NO: 19)
Mouse TNFα-F: 5'-ACGGCATGGATCTCAAAGAC-3'

(SEQ ID NO: 20)
Mouse TNFα-R: 5'-AGATAGCAAATCGGCTGACG-3'

(SEQ ID NO: 21)
Mouse IL-1β-F: 5'-CAAGCAATACCCAAAGAAGA-3'

(SEQ ID NO: 22)
Mouse IL-1β-R: 5'-GAACAGTCCAGCCCATAC-3'

(SEQ ID NO: 23)
Mouse TGF-β1-F: 5'-TGCGCTTGCAGAGATTAAAA-3'

(SEQ ID NO: 24)
Mouse TGF-β1-R: 5'-CGTCAAAAGACAGCCACTCA-3'

(SEQ ID NO: 25)
Mouse Snail 1-F: 5'-AGCCCAACTATAGCGAGCTG-3'

(SEQ ID NO: 26)
Mouse Snail 1-R: 5'-GGGTACCAGGAGAGAGTCCC-3'

(SEQ ID NO: 27)
Mouse c-myc-F: 5'-TCCATCCTATGTTGCGGTCG-3'

(SEQ ID NO: 28)
Mouse c-myc-R: 5'-AACCGCTCCACATACAGTCC-3'

(SEQ ID NO: 29)
Mouse CTGF-F: 5'-AGGGCCTCTTCTGCGATTTC-3'

(SEQ ID NO: 30)
Mouse CTGF-R: 5'-CTTTGGAAGGACTCACCGCT-3'
```

Furthermore, to observe the nuclear localization of β-catenin, which is downstream of the TGF-β signaling pathway, the unilateral obstructed kidneys were excised on postoperative day 21, and 4-µm-thick paraffin-embedded sections were prepared from each kidney. The sections were subjected to immunofluorescence staining with an anti-β-catenin antibody (BD Bioscience). The nuclei were stained with DAPI, and the fluorescence intensity of intranuclear β-catenin was measured using IMARIS software (Zurich, Switzerland) and BZ-II analyzer (Keyence, Osaka, Japan) (n=4 per kidney). Statistical analysis was performed by analysis of variance and Tukey-Kramer adjustment using the JMP statistical software package.

Results

Figure 9:
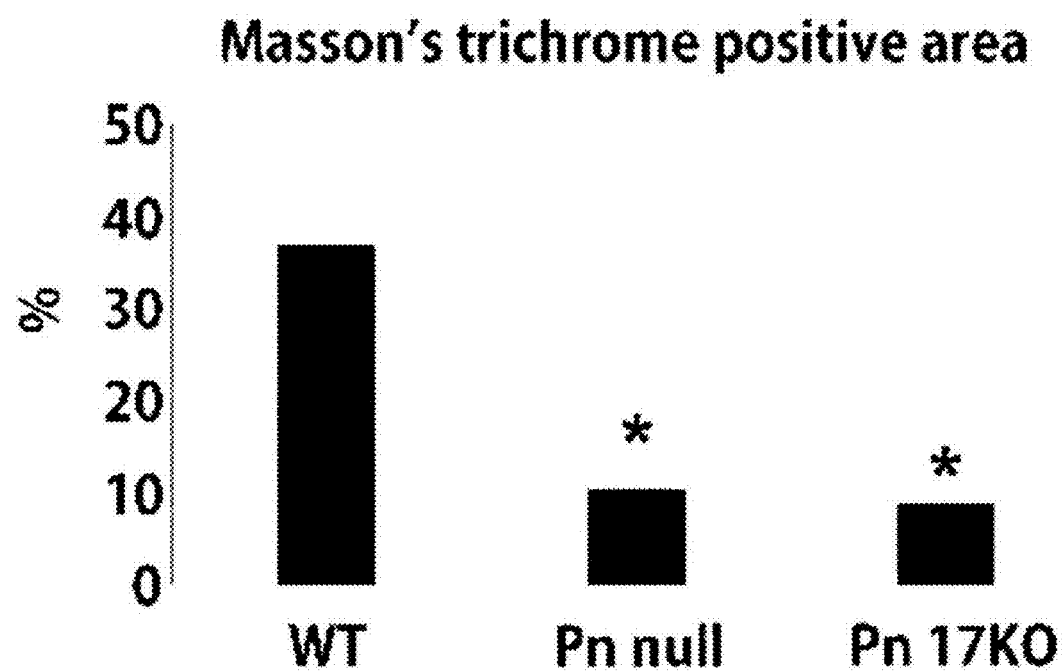
FIG. 9 shows the Masson's trichrome-positive area (fibrotic area) measured after the Masson's trichrome staining on paraffin-embedded sections of the kidney excised on day 21 in the UUO model induced in wild-type mice, periostin exon 17 knockout mice (Pn 17KO mice), and complete periostin knockout mice (Pn null mice).

The measurement results of the Masson's trichrome-positive area (fibrotic area) are shown in FIG. 9 and expressed as the percentage (%) of the fibrotic area in the kidney area. In the graph, * indicates a significant difference from WT ($P<0.05$). The Masson's trichrome-positive area was significantly smaller in the Pn null and Pn 17KO mice than in the wild-type mice.

Figure 10:
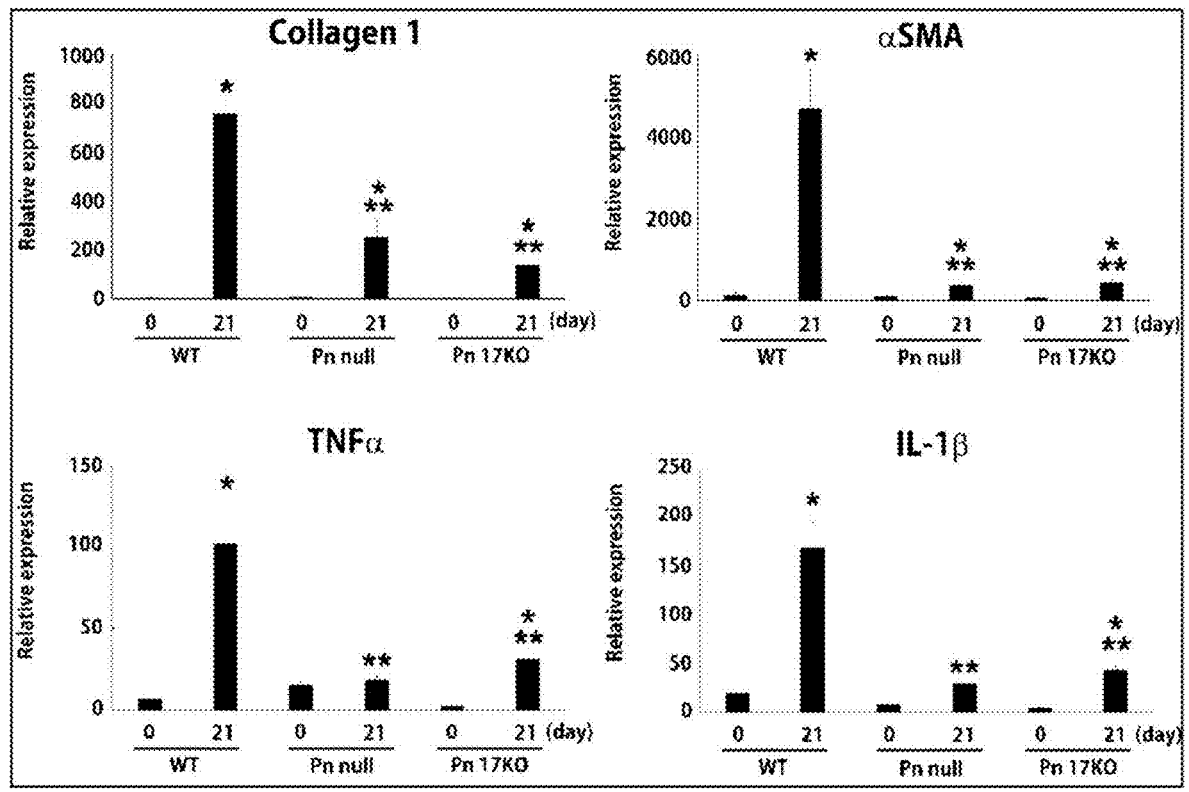
FIG. 10 shows the results of quantitative PCR for measurement of the mRNA expression levels of fibrosis markers (αSMA, type I collagen) and inflammatory markers (TNFα, IL-1β) in the kidneys excised on days 0 and 21 in the UUO model induced in wild-type mice, periostin exon 17 knockout mice (Pn 17KO mice), and complete periostin knockout mice (Pn null mice).

The measured mRNA expression levels of the fibrosis markers (αSMA, type I collagen) and the inflammatory markers (TNFα, IL-1β) are shown in FIG. 10. In each graph, * indicates a significant difference from day 0 ($P<0.05$), and ** indicates a significant difference from WT on day 21 ($P<0.05$). The expression level of each marker on postoperative day 21 was significantly lower in the Pn null and Pn 17KO mice than in the wild-type mice. The above results show that periostin, in particular, a periostin variant containing exon 17, is involved in renal fibrosis after ureteral obstruction.

Figure 11:
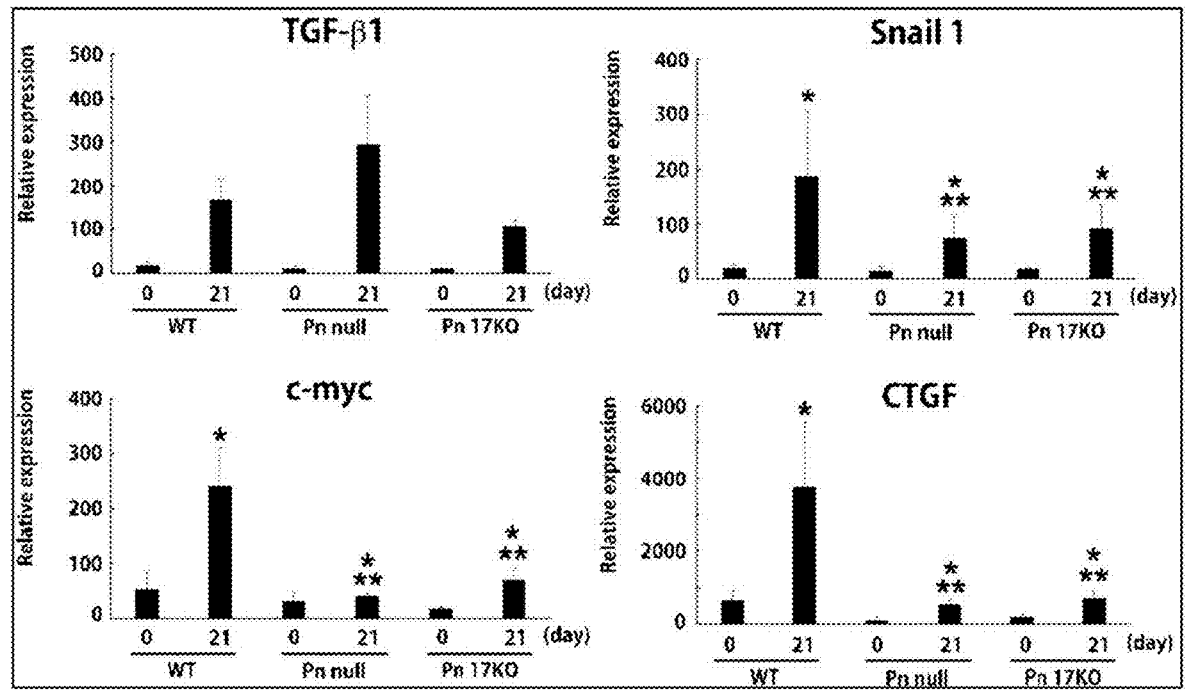
FIG. 11 shows the results of quantitative PCR for measurement of the mRNA expression levels of TGF-β signaling-related molecules (TGF-β, Snail 1, c-myc, CTGF) in the kidneys excised on days 0 and 21 in the UUO model induced in wild-type mice, periostin exon 17 knockout mice (Pn 17KO mice), and complete periostin knockout mice (Pn null mice).

The measured mRNA expression levels of the TGF-β signaling-related molecules (TGF-β1, Snail 1, c-myc, CTGF) are shown in FIG. 11. In each graph, * indicates a significant difference from day 0 ($P<0.05$), and ** indicates a significant difference from WT on day 21 ($P<0.05$). There was no intergroup difference in TGF-β1 expression on postoperative day 21. The expression levels of Snail 1, c-myc, and CTGF, which are transcripts involved in the TGF-β signaling pathway, on postoperative day 21 were significantly lower in the Pn null and Pn 17KO mice than in the wild-type mice.

Figure 12:
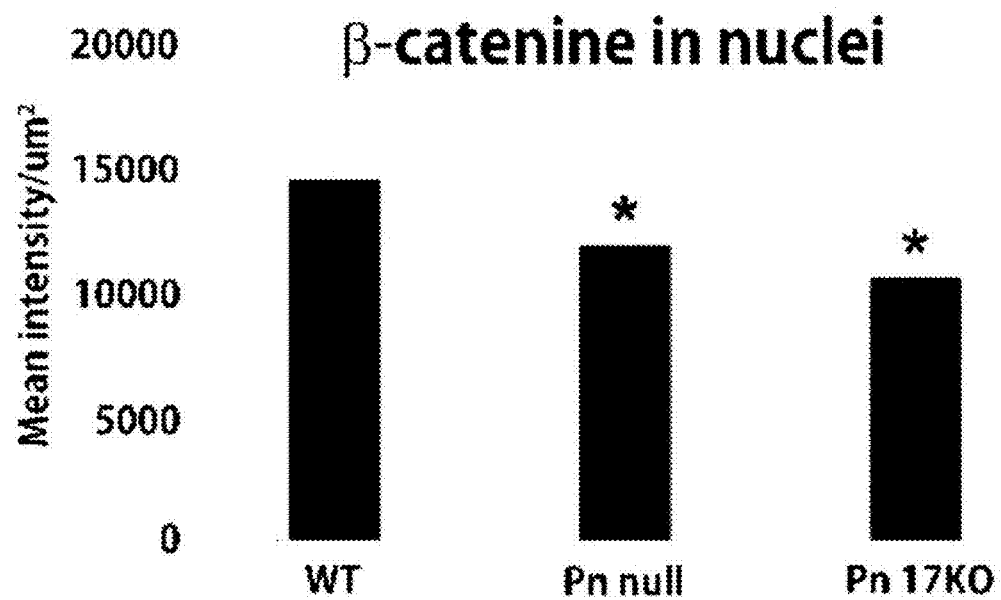
FIG. 12 shows the nuclear localized β-catenin level measured after fluorescence staining with an anti-β-catenin antibody and nuclear staining with DAPI performed on paraffin-embedded sections of the kidney excised on day 21 in the UUO model induced in wild-type mice, periostin exon 17 knockout mice (Pn 17KO mice), and complete periostin knockout mice (Pn null mice).

The measurement results of the nuclear localized β-catenin level are shown in FIG. 12 and expressed as fluorescence intensity per unit area ($\mu m^2$). In the graph, * indicates a significant difference from WT (P<0.05). The nuclear localized β-catenin level on postoperative day 21 was significantly lower in the Pn null and Pn 17KO mice than in the wild-type mice.

The above results show that a periostin variant containing exon 17 is involved in TGF-β signaling and accelerates fibrosis, but blockade of periostin exon 17 prevents fibrosis.

Example 1: Selective Skipping of Exons 17 and 21 Using Antisense Oligonucleotides The findings from Reference Examples 1 to 4 demonstrate that the inhibition of the whole periostin protein prevents renal fibrosis in the UUO model but may cause body size reduction and dental hypoplasia. Based on these findings, we hypothesized that selective blockade of periostin exon 17 would be a safer treatment option. The same would be true on selective blockade of periostin exon 21. We investigated the use of an antisense nucleic acid designed to induce the formation of an mRNA lacking exon 17 or exon 21 for selective blockade of periostin exon 17 or 21.

Experimental Methods (1) Antisense Nucleic Acids

Morpholino antisense oligonucleotides designed to induce skipping of exon 17 or 21 of a human periostin gene were purchased from Funakoshi Co., Ltd. The nucleotide sequences of the antisense nucleic acids are as follows.

```
Human exon 17-skipping antisense oligonucleotide:
                                     (SEQ ID NO: 3)
5'-CCATGTATAACATTGATTTTTACCTTCAGT-3'

Human exon 21-skipping antisense oligonucleotide:
                                     (SEQ ID NO: 4)
5'-TTGTTGTCCTTTTACTAACCTCCCT-3'

Control antisense oligonucleotide:
                                     (SEQ ID NO: 6)
5'-CCTCTTACCTCAGTTACAATTTATA-3'
```

The human exon 17-skipping antisense oligonucleotide targets the region of positions 24267 to 24296 of SEQ ID NO: 1. The human exon 21-skipping antisense oligonucleotide targets the region of positions 29540 to 29564 of SEQ ID NO: 1.

(2) Cells

The cells used were human cardiac fibroblasts (COSMO BIO, Catalog #6300) and human breast cancer MDA-MB-231 cells (ATCC No. HTB-26). The human cardiac fibroblasts and the human breast cancer MDA-MB-231 cells were cultured in DMEM with 10% fetal bovine serum (FBS) and 1% penicillin/streptomycin. These cells were transfected with the human exon 17-skipping antisense oligonucleotide or the human exon 21-skipping antisense oligonucleotide using the transfection reagent "Endo-Porter (Gene Tools)". The final concentration of the antisense nucleic acid in medium was 10 μM. At 48 hours after transfection, total RNA was extracted from the cells and subjected to cDNA synthesis (see Reference Example 1). The resulting cDNA was subjected to RT-PCR. The presence or absence of the PCR products of interest was examined by agarose gel electrophoresis.

For the detection of exon 17 skipping, the following primers were used.

```
Forward primers (3 types)
Human periostin exon 17 primer:
                                     (SEQ ID NO: 31)
5'-AACCAAAGTTGTGGAACCA-3'

Human periostin exon 16/18 primer:
                                     (SEQ ID NO: 32)
5'-ATCCCCGTGACTGTCTATAGACCCA-3'

Human periostin exon 16/19 primer:
                                     (SEQ ID NO: 33)
5'-ATCCCCGTGACTGTCTATAAGCCAA-3'

Reverse primer (1 type)
Human periostin exon 20 primer:
                                     (SEQ ID NO: 34)
5'-GACCATCACCACCTTCAATG-3'
```

For the detection of exon 21 skipping, the following primers were used.

```
Forward primers (2 types)
Human periostin exon 21 primer:
                                     (SEQ ID NO: 35)
5'-GGTCACCAAGGTCACCAAATTC-3'

Human periostin exon 20/22 primer:
                                     (SEQ ID NO: 36)
5'-GTTACAAGAAGACACACCCGTG-3'

Reverse primer (1 type)
Human periostin exon 23 primer:
                                     (SEQ ID NO: 37)
5'-CCTGAAGTCAACTTGGCTCTCAC-3'
```

Results

Figure 13:
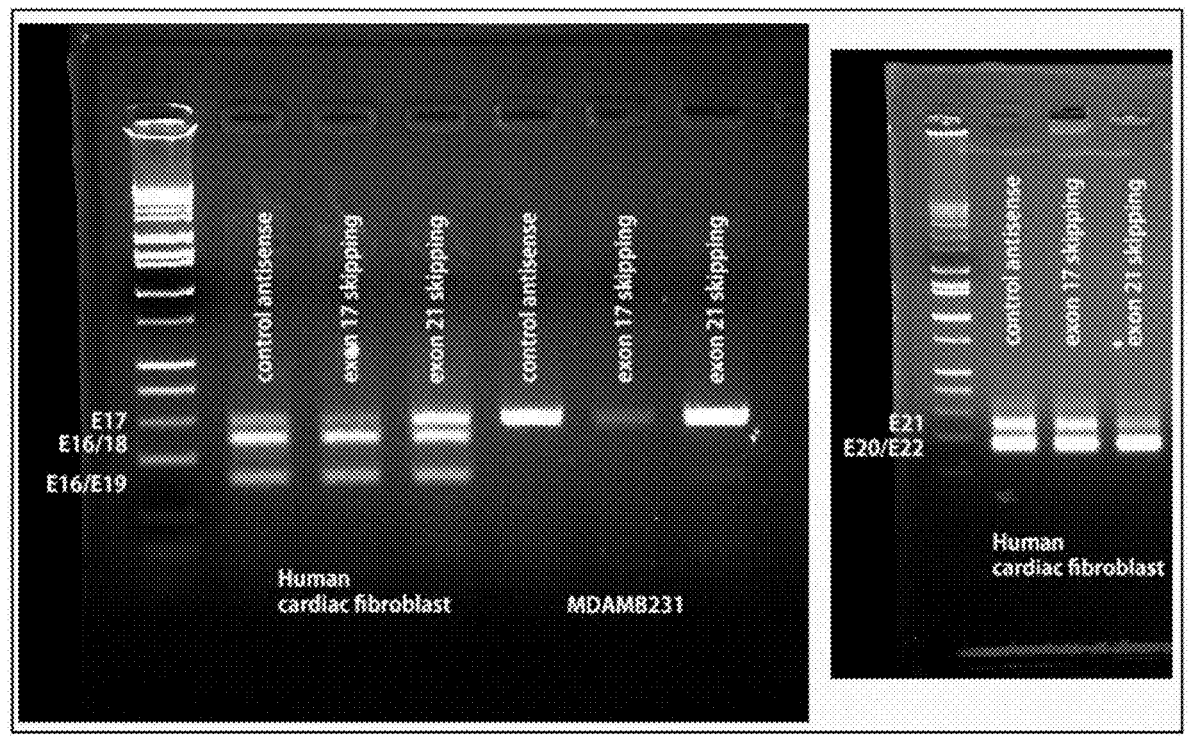
FIG. 13 shows the results of RT-PCR using a primer set for detection of exon 17 skipping or exon 21 skipping in the extracted RNA from human cardiac fibroblasts and human breast cancer cells subjected to transfection with a morpholino antisense oligonucleotide designed to induce skipping of exon 17 or 21 of a human periostin gene and subsequent 48-hour culture.

The results are shown in FIG. 13. As is clear from FIG. 13, the transfection of the specific antisense nucleic acid reduced the corresponding splice variant.

Example 2: Effect of Exon 17-Skipping Antisense Oligonucleotide on TGF-β Signaling Experimental Methods Human renal proximal tubular epithelial cells (hRPTEC, ATCC No. PCS-400-010) were cultured in a renal epithelial cell basal medium (REBM, Cambrex Bio Science Inc.) with 10% fetal bovine serum (FBS) and 1% penicillin/streptomycin. The cells were transfected with the human exon 17-skipping antisense oligonucleotide (Pn exon 17 AS) or the control antisense oligonucleotide (Control AS) as described in Example 1. At 24 hours after transfection, the medium was replaced by a serum-free medium. At 24 hours thereafter, human TGF-β1 (PeproTech) was added to the medium, and culture was continued for additional 24 hours. After cell culture, total RNA was extracted from the cells and subjected to cDNA synthesis (see Reference Example 1). The resulting cDNA was subjected to quantitative PCR using the primers shown below to measure the expression level of the splice variant Pn1 (containing exons 17 and 21, see FIG. 1) (n=3 per group) and the mRNA expression levels of the downstream molecules of TGF-β-induced signaling (αSMA, Snail 1, TNFα, CTGF, vimentin) (n=4 per group). Statistical analysis was performed by analysis of variance and Tukey-Kramer adjustment using the JMP statistical software package.

```
Human periostin exon 17 (Pn1)-F:
                                 (SEQ ID NO: 38)
5'-AGCCTATTATCAAAACTGAAGG-3'

Human periostin exon 17 (Pn1)-R:
                                 (SEQ ID NO: 39)
5'-GTCTCCCTGAAGCAGTCTTTT-3'

Human αSMA-F:
                                 (SEQ ID NO: 40)
5'-CAATGAGCTTCGTGTTGCCC-3'

Human αSMA-R:
                                 (SEQ ID NO: 41)
5'-CATAGAGAGACAGCACCGCC-3'

Human Snail 1-F:
                                 (SEQ ID NO: 42)
5'-GCTGACCTCCCTGTCAGATG-3'

Human Snail 1-R:
                                 (SEQ ID NO: 43)
5'-GCACCCAGGCTGAGGTATTC-3'

Human TNFα-F:
                                 (SEQ ID NO: 44)
5'-ATGAGCACTGAAAGCATGATCC-3'

Human TNFα-R:
                                 (SEQ ID NO: 45)
5'-GAGGGCTGATTAGAGAGAGGTC-3'

Human CTGF-F:
                                 (SEQ ID NO: 46)
5'-AGTGCATCCGTACTCCCAAA-3'

Human CTGF-R:
                                 (SEQ ID NO: 47)
5'-TCTTCTTCATGACCTCGCCG-3'

Human Vimentin-F:
                                 (SEQ ID NO: 48)
5'-GGACCAGCTAACCAACGACA-3'

Human Vimentin-R:
                                 (SEQ ID NO: 49)
5'-AAGGTCAAGACGTGCCAGAG-3'
```

Results

Figure 14:
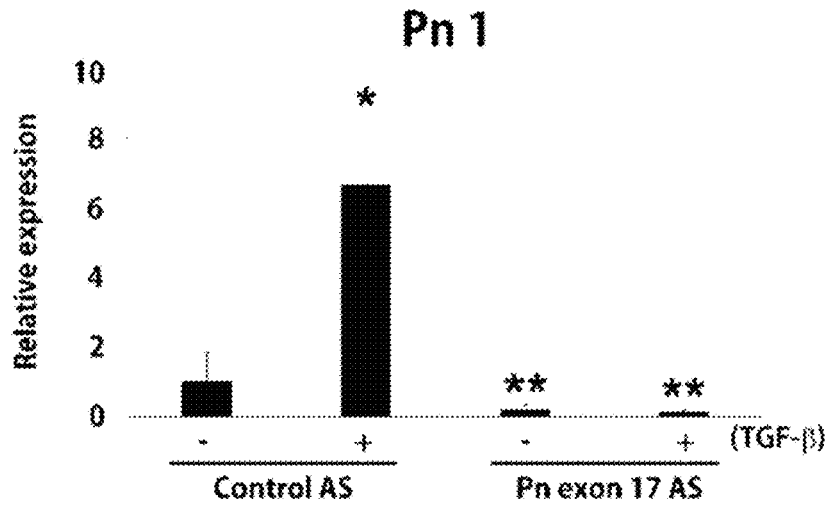
FIG. 14 shows the results of quantitative PCR for measurement of the expression level of splice variant Pn1 (see FIG. 1) in the extracted RNA from human renal proximal tubular epithelial cells subjected to transfection with a morpholino antisense oligonucleotide designed to induce skipping of exon 17 of a human periostin gene, subsequent 24-hour culture, and additional 24-hour culture in a TGF-β-containing medium.
Figure 15:
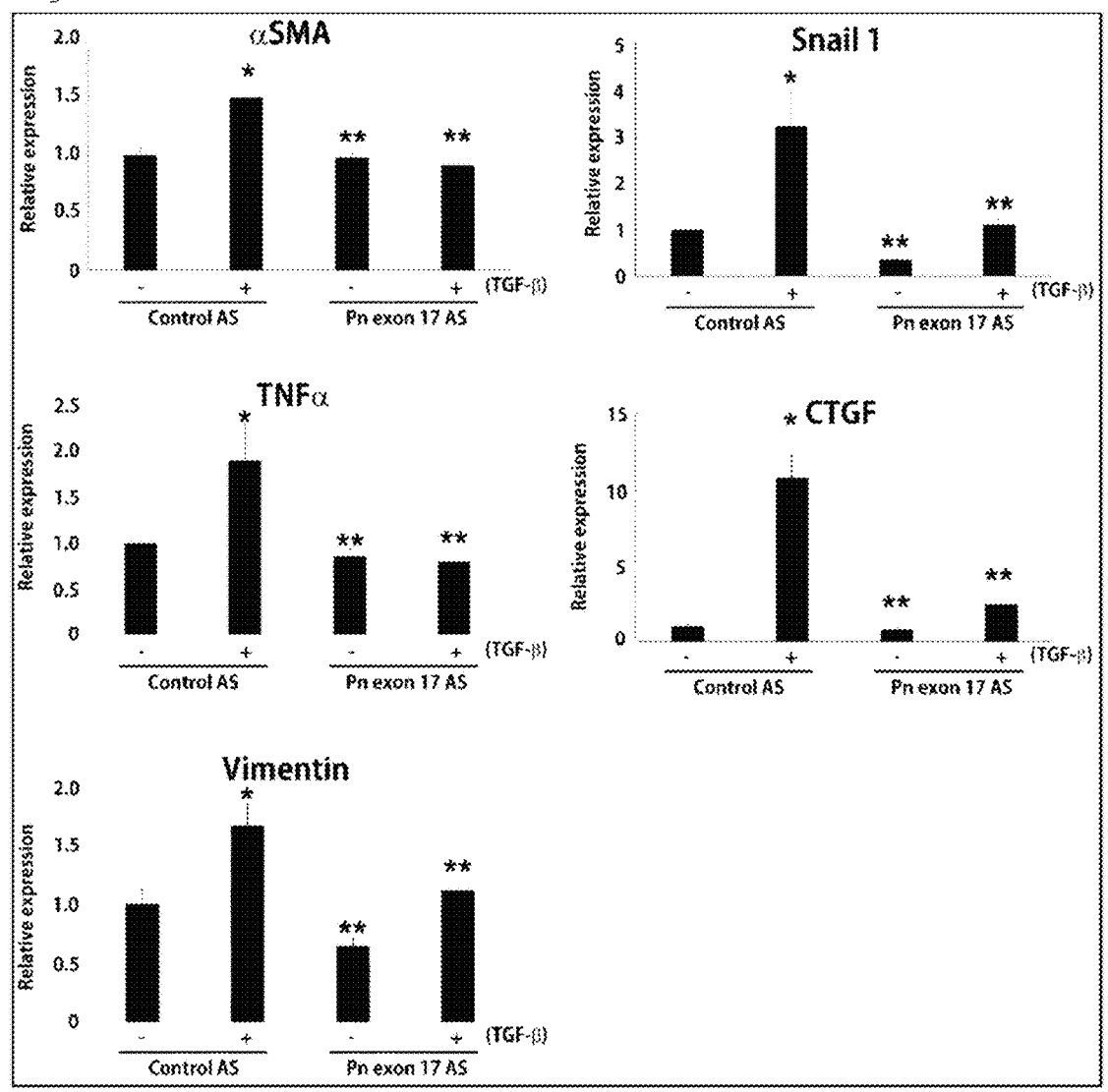
FIG. 15 shows the results of quantitative PCR for measurement of the mRNA expression levels of downstream molecules of TGF-β-induced signaling (αSMA, Snail 1, TNFα, CTGF, vimentin) in the extracted RNA from human renal proximal tubular epithelial cells subjected to transfection with a morpholino antisense oligonucleotide designed to induce skipping of exon 17 of a human periostin gene, subsequent 24-hour culture, and additional 24-hour culture in a TGF-β-containing medium.

The expression level of the splice variant Pn1 is shown in FIG. 14. The mRNA expression levels of the downstream molecules of TGF-β-induced signaling are shown in FIG. 15. In FIGS. 14 and 15, * indicates a significant difference from TGF-β (−) Control AS (P<0.05), and ** indicates a significant difference from TGF-β (+) Control AS (P<0.05). As shown in FIG. 14, the expression level of the splice variant Pn1 was significantly higher in the TGF-β (+) Control AS group. As shown in FIG. 15, the expressions of αSMA, Snail 1, TNFα, CTGF, and Vimentin, which are downstream molecules of TGF-β-induced signaling, were induced to significantly higher levels in the TGF-β (+) Control AS group, but the induction was significantly suppressed in TGF-β (+) Pn exon 17 AS group. These results show that the antisense nucleic acid designed to induce selective skipping of periostin exon 17 is effective for preventing fibrosis mediated by TGF-β signaling.

Example 3: Examination of Effect of Exon 17-Skipping Antisense Oligonucleotide on TGF-β Signaling Experimental Methods Luciferase-expressing mouse breast cancer (4T1-Luc) cells were cultured in DMEM with 10% FBS and 1% penicillin/streptomycin. A morpholino antisense oligonucleotide designed to induce skipping of exon 17 of a mouse periostin gene was purchased from Funakoshi Co., Ltd. The nucleotide sequence of the antisense oligonucleotide is as follows.

```
Mouse exon 17-skipping antisense oligonucleotide:
                                 (SEQ ID NO: 5)
5'-TGCTGAAAACATAGAAAGTGGAGCA-3'
```

The mouse exon 17-skipping antisense oligonucleotide targets the region of positions 21118 to 21142 of the mouse periostin gene represented by SEQ ID NO: 2.

The 4T1-Luc cells were transfected with the mouse exon 17-skipping antisense oligonucleotide or the control antisense oligonucleotide (SEQ ID NO: 6) as described in Example 1. After 2 days of culture, the cells were detached, and cell suspension was prepared. The cell suspension (containing $5 \times 10^5$ 4T1-Luc cells per mouse) was injected via the tail vein to nude mice (BALB/c-nu, female, 8 to 10 weeks old) (n=3 per group). At 5 days after injection, the lung was excised from each mouse under anesthesia and homogenized. The homogenate was subjected to the measurement of luciferase activity using the Dual-Luciferase Reporter Assay System (Promega, #E1910). The Mann Whitney test (MWU) was used for comparison between the two groups.

Results

Figure 16:
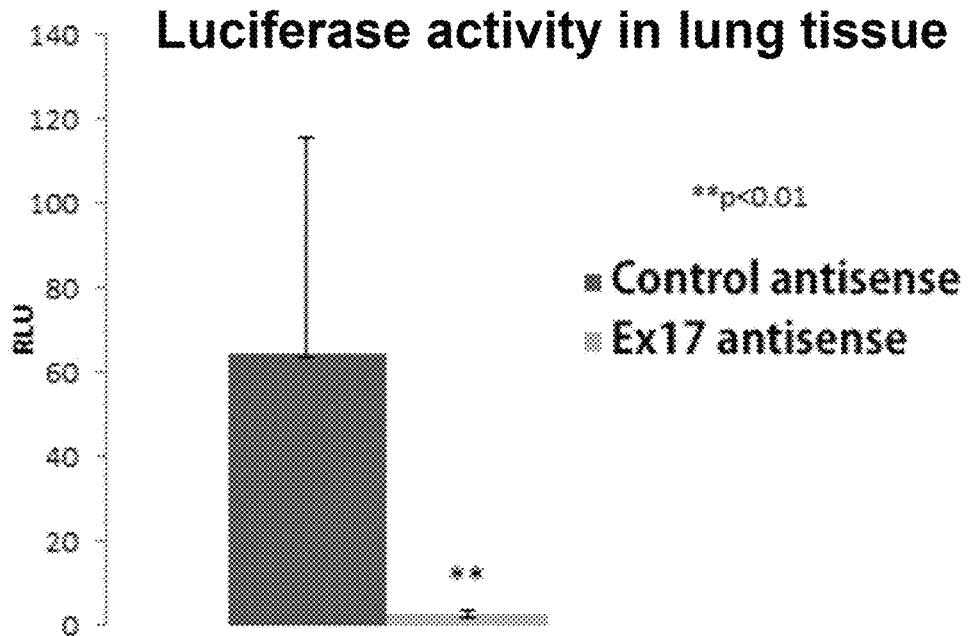
FIG. 16 shows the luciferase activity as a measure of pulmonary metastasis in nude mice at 5 days after tail vein injection of a cell suspension of luciferase-expressing mouse breast cancer cells (4T1-Luc) subjected to transfection with a morpholino antisense oligonucleotide designed to induce skipping of exon 17 of a mouse periostin gene and subsequent 2-day culture.

The results are shown in FIG. 16. The mice injected with the 4T1-Luc cells transfected with the control antisense oligonucleotide showed a higher luciferase activity, indicating pulmonary metastasis of the 4T1-Luc cells. In contrast, the mice injected with the 4T1-Luc cells transfected with the exon 17-skipping antisense oligonucleotide showed a very low luciferase activity, indicating little pulmonary metastasis of the 4T1-Luc cells. These results show that the antisense nucleic acid designed to induce selective skipping of periostin exon 17 prevents pulmonary metastasis of breast cancer cells.

Example 4: Enhancement of Effect of Paclitaxel by Exon 17 Skipping or Exon 21 Skipping in Periostin-Highly-Expressing Breast Cancer Cell Line BT549

Experimental Methods

Periostin-highly-expressing human breast cancer cell line BT549 was cultured in RPMI 1640 with 10% FBS and 1% penicillin/streptomycin. The BT549 cells are a triple-negative breast cancer cell line, which is negative for estrogen receptor, progesterone receptor, and human epidermal growth factor receptor 2 (HER2).

The BT549 cells were transfected with the human exon 17-skipping antisense oligonucleotide or the human exon 21-skipping antisense oligonucleotide as described in Example 1. The cells were subsequently seeded in an amount of $5 \times 10^3$ cells/well on a 96-well plate. Similarly, the BT549 cells were transfected with the control antisense oligonucleotide and seeded on a 96-well plate as the control group. On the day after seeding, paclitaxel was added at a final concentration of 10 nM to the wells. After 72 hours of culture, cell proliferation (number of viable cells) and ATP-producing capacity (ATP quantification) were evaluated. The number of viable cells was measured using the CellTiter 96 AQueous One Solution Cell Proliferation Assay (trade name, Promega, #G3582) (MTS assay). The amount of ATP was measured using the CellTiter-Glo Luminescent Cell Viability Assay (trade name, Promega, #G7570) (ATP assay). The Tukey-Kramer test was used for intergroup comparison.

Results

Figure 17:
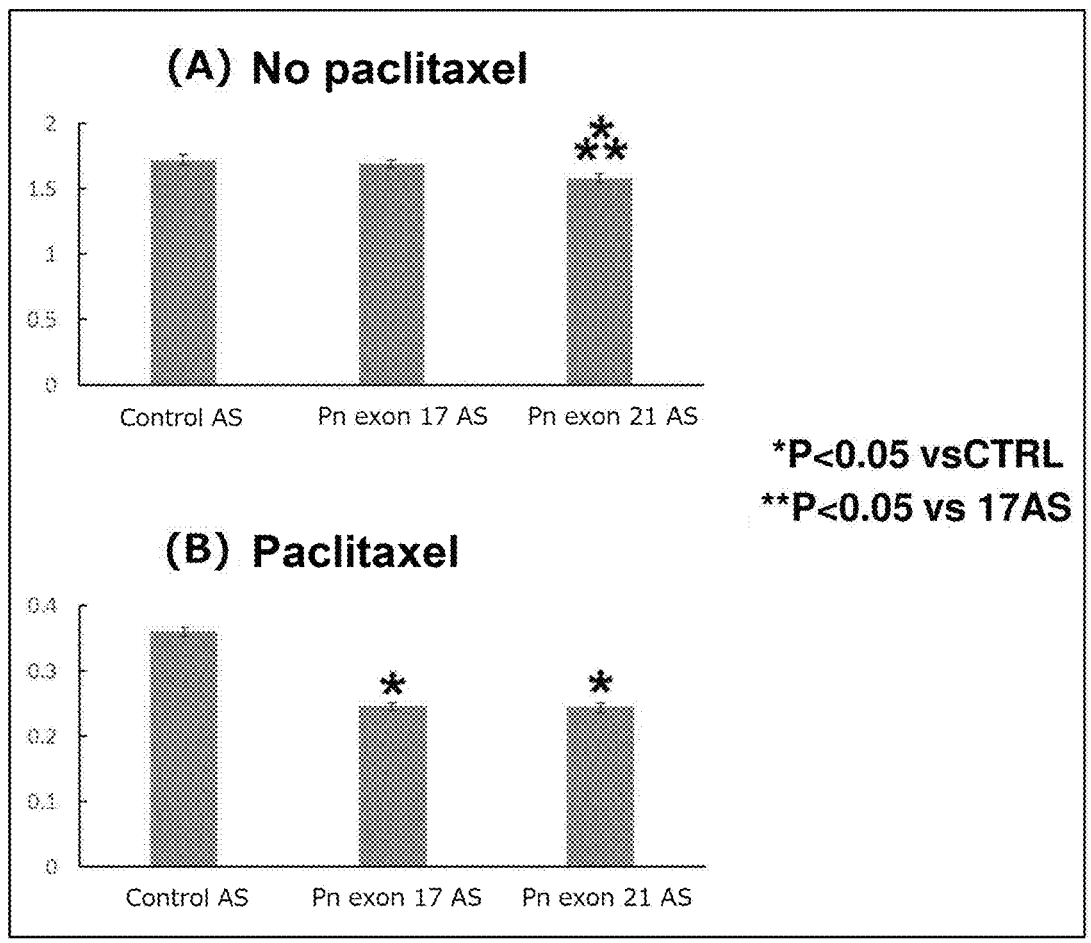
FIG. 17 shows the number of viable cells measured at 72 hours after treatment or non-treatment with anticancer paclitaxel in human breast cancer cells (BT549) subjected to transfection with a morpholino antisense oligonucleotide designed to induce skipping of exon 17 of a human periostin gene or a morpholino antisense oligonucleotide designed to induce skipping of exon 21 of a human periostin gene.

The results of the MTS assay are shown in FIG. 17. The BT549 cells transfected with the exon 21-skipping antisense oligonucleotide showed a significant reduction in cell proliferation as compared with the BT549 cells transfected with the exon 17-skipping antisense oligonucleotide and the BT549 cells transfected with the control antisense oligonucleotide (FIG. 17A). In the case of paclitaxel treatment of the BT549 cells transfected with the exon 17-skipping antisense oligonucleotide, the BT549 cells transfected with the exon 21-skipping antisense oligonucleotide, and the BT549 cells transfected with the control antisense oligonucleotide, both the BT549 cells transfected with the exon 17-skipping antisense oligonucleotide and the BT549 cells transfected with the exon 21-skipping antisense oligonucleotide showed a significant reduction in cell proliferation as compared with the BT549 cells transfected with the control antisense oligonucleotide (FIG. 17B).

Figure 18:
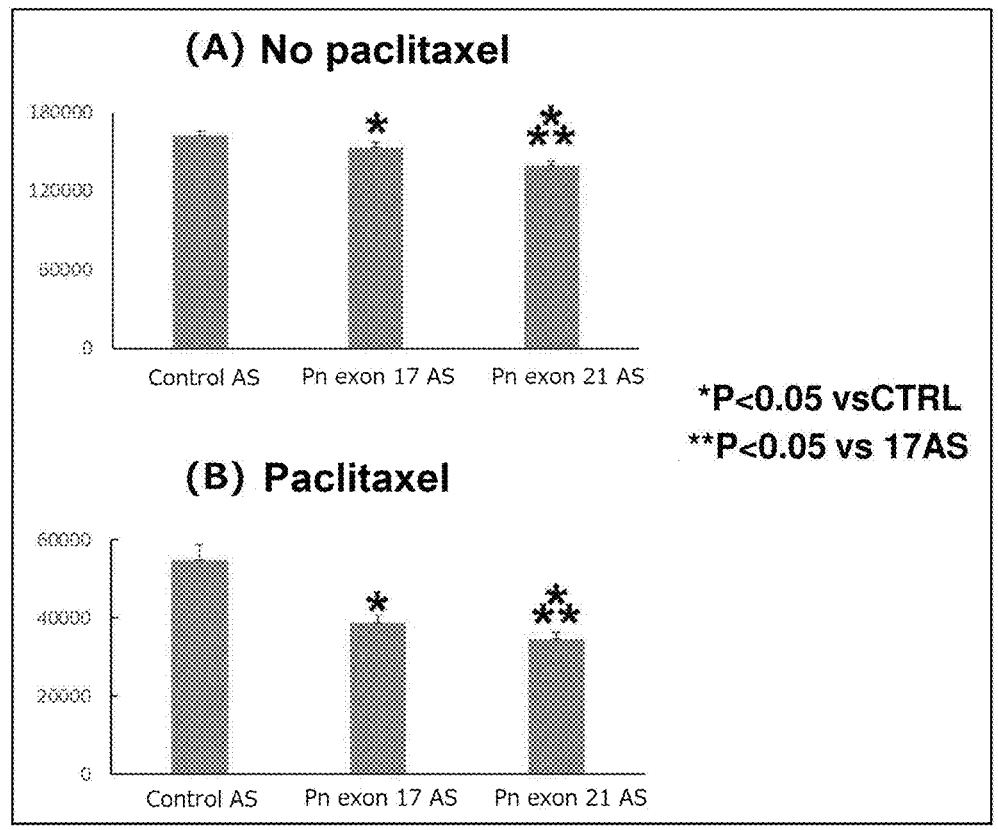
FIG. 18 shows the amount of ATP production measured at 72 hours after treatment or non-treatment with anticancer paclitaxel in human breast cancer cells (BT549) subjected to transfection with a morpholino antisense oligonucleotide designed to induce skipping of exon 17 of a human periostin gene or a morpholino antisense oligonucleotide designed to induce skipping of exon 21 of a human periostin gene.

The results of the ATP assay are shown in FIG. 18. Both the BT549 cells transfected with the exon 17-skipping antisense oligonucleotide and the BT549 cells transfected with the exon 21-skipping antisense oligonucleotide showed a significant reduction in ATP production as compared with the BT549 cells transfected with the control antisense oligonucleotide (FIG. 18A). In the comparison between the BT549 cells transfected with the exon 17-skipping antisense oligonucleotide and the BT549 cells transfected with the exon 21-skipping antisense oligonucleotide, the BT549 cells transfected with the exon 21-skipping antisense oligonucleotide showed a significant reduction in ATP production as compared with the BT549 cells transfected with the exon 17-skipping antisense oligonucleotide (FIG. 18A). In the case of paclitaxel treatment of the BT549 cells transfected with the exon 17-skipping antisense oligonucleotide, the BT549 cells transfected with the exon 21-skipping antisense oligonucleotide, and the BT549 cells transfected with the control antisense oligonucleotide, both the BT549 cells transfected with the exon 17-skipping antisense oligonucleotide and the BT549 cells transfected with the exon 21-skipping antisense oligonucleotide showed a significant reduction in ATP production as compared with the BT549 cells transfected with the control antisense oligonucleotide (FIG. 18B). When the BT549 cells transfected with the exon 17-skipping antisense oligonucleotide and the BT549 cells transfected with the exon 21-skipping antisense oligonucleotide were compared in the presence of paclitaxel, the BT549 cells transfected with the exon 21-skipping antisense oligonucleotide showed a significant reduction in ATP production as compared with the BT549 cells transfected with the exon 17-skipping antisense oligonucleotide (FIG. 18B).

These results show that the antisense nucleic acid designed to induce selective skipping of periostin exon 17 and the antisense nucleic acid designed to induce selective skipping of periostin exon 21 enhance the anticancer drug sensitivity of breast cancer cells.

Reference Example 5: Examination of Pulmonary Metastasis of Breast Cancer Cells in Periostin Knockout Mice Animals Used The knockout animals generated in Reference Example 2, namely, exon 17 knockout mice (Pn 17KO mice, n=6), exon 21 knockout mice (Pn 21KO mice, n=6), and complete periostin knockout mice (Pn null mice, n=6) were used. Wild-type mice (BALB/c, n=6) were used as the control group. All animals were 8-week-old female mice.

Experimental Methods

Mouse breast cancer cell line 4T1 was cultured in DMEM with 10% FBS and 1% penicillin/streptomycin. Cell suspension was prepared and transplanted in an amount of $1\times10^3$ cells into the left paw of each mouse. At 3 weeks after transplantation, each mouse was euthanized, the lung was excised and subjected to staining with Bouin's fixative, and pulmonary metastatic colonies were visually counted. The Tukey-Kramer test was used for intergroup comparison.

Results

The results are shown in FIG. 19. A large number of pulmonary metastatic colonies were observed in the wild-type mice (WT). In contrast, the exon 17 knockout mice (Pn 17KO mice), the exon 21 knockout mice (Pn 21KO mice), and the complete periostin knockout mice (Pn null mice) showed a significant reduction in the number of pulmonary metastatic colonies as compared with the wild-type mice.

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A method for treating a disease in a patient, characterized by upregulated expression of periostin splice variant containing exon 17 or exon 21 after the onset of the disease, the method comprising:
   administering to the patient, an effective amount of a nucleic acid that induces skipping of exon 17 of periostin gene or an effective amount of a nucleic acid that induces skipping of exon 21 of periostin gene, wherein the disease is selected from the group consisting of heart failure, renal failure, breast cancer, pancreatic cancer, malignant melanoma, bronchial asthma, diabetic retinopathy, knee osteoarthritis, idiopathic interstitial pneumonia, and age-related macular degeneration;
   wherein the nucleic acid is an antisense nucleic acid;
   wherein the antisense nucleic acid that induces skipping of exon 17 is one or more antisense nucleic acids of 14 to 50 bases in length, which target the region of positions 24143 to 24323; and
   wherein the antisense nucleic acid that induces skipping of exon 21 is one or more antisense nucleic acids of 14 to 50 bases, which target the region of positions 29412 to 29595, of the nucleotide sequence represented by SEQ ID NO: 1.

2. The method according to claim 1, wherein the antisense nucleic acid that induces skipping of exon 17 targets at least one of the regions of positions 24191 to 24193, positions 24215 to 24220, positions 24247 to 24254, positions 24249 to 24258, positions 24252 to 24255, or positions 24273 to 24275 of the nucleotide sequence represented by SEQ ID NO: 1.

3. The method according to claim 1, wherein the antisense nucleic acid that induces skipping of exon 21 targets at least one of the regions of positions 29460 to 29462, positions 29468 to 29474, positions 29472 to 29479, positions 29509 to 29515, positions 29525 to 29531, positions 29530 to 29536, positions 29531 to 29538, positions 29534 to 29539, positions 29534 to 29541, positions 29536 to 29542, or positions 29545 to 29547 of the nucleotide sequence represented by SEQ ID NO: 1.

4. The method according to claim 1, wherein the antisense nucleic acids are provided in an adeno-associated viral vector and the adeno-associated viral vector expresses the antisense nucleic acid that induces skipping of exon 17 or the antisense nucleic acid that induces skipping of exon 21.

5. The method according to claim 1, further comprising providing an additional therapeutic agent for treating the disease.

* * * * *